United States Patent
Macoviak et al.

(10) Patent No.: US 6,508,777 B1
(45) Date of Patent: Jan. 21, 2003

(54) CIRCULATORY SUPPORT SYSTEM AND METHOD OF USE FOR ISOLATED SEGMENTAL PERFUSION

(75) Inventors: John Macoviak, La Jolla, CA (US); Wilfred J. Samson, Saratoga, CA (US); Steve Baker, Sunnyvale, CA (US); James J. Leary, Sunnyvale, CA (US)

(73) Assignee: Cardeon Corporation, Cupertino, CA (US)

( * ) Notice: Subject to any disclaimer, the term of this patent is extended or adjusted under 35 U.S.C. 154(b) by 0 days.

(21) Appl. No.: 09/306,555

(22) Filed: May 6, 1999

Related U.S. Application Data

(60) Provisional application No. 60/084,835, filed on May 8, 1998.

(51) Int. Cl.[7] .................. A61M 37/00; A61M 5/00; A61M 29/00; A61N 1/30
(52) U.S. Cl. ............... 604/4.01; 604/6.11; 604/6.16; 604/8; 604/9; 604/19; 604/96.01; 604/101.01
(58) Field of Search ............... 604/4.01, 8, 9, 604/10, 101.01, 101.03–101.05, 6.11, 6.14, 6.16, 19, 28, 506–510, 96.01; 422/44

(56) References Cited

U.S. PATENT DOCUMENTS

| | | | |
|---|---|---|---|
| 3,991,767 A | 11/1976 | Miller, Jr. et al. | 604/8 |
| 3,995,617 A | 12/1976 | Watkins et al. | 128/1 D |
| 3,996,938 A | 12/1976 | Clark, III | 128/348 |
| 4,192,302 A | 3/1980 | Boddie | 128/214 R |

(List continued on next page.)

FOREIGN PATENT DOCUMENTS

| | | | | |
|---|---|---|---|---|
| DE | 35 35 641 A | 4/1987 | ......... | A61M/25/00 |
| EP | 0 218 275 A1 | 4/1987 | ......... | A61M/25/00 |
| WO | WO 97/17100 | 5/1997 | ......... | A61M/29/00 |
| WO | WO 97/42879 | 11/1997 | ......... | A61B/17/00 |
| WO | WO 98/02084 | 1/1998 | | |
| WO | WO 99/04848 | 2/1999 | ......... | A61M/29/00 |

OTHER PUBLICATIONS

Barbut et al., "Determination or Size of Aortic Emboli and Embolic Load During Coronary Artery Bypass Grafting," Ann Thorac Surg; 63:1262–7 (1997).

(List continued on next page.)

*Primary Examiner*—Angela D. Sykes
*Assistant Examiner*—Leslie R. Deak
(74) *Attorney, Agent, or Firm*—Fulwider Patton Lee & Utecht

(57) ABSTRACT

A circulatory support system and method for circulatory support are described for performing cardiopulmonary bypass using differential perfusion and/or isolated segmental perfusion of the circulatory system. The circulatory support system includes one or more venous cannulae for draining blood from the venous side of the patient's circulatory system, one or more arterial cannulae for perfusing the arterial side of the patient's circulatory system, and one or more blood circulation pumps connected between the venous cannulae and the arterial cannulae. The arterial cannulae and the venous cannulae of the circulatory support system may take one of several possible configurations. The circulatory support system is configured to segment a patient's circulatory system into one or more isolated circulatory loops. The circulatory loops may be isolated from one another and/or from the remainder of the patient's circulatory system on the venous side, as well as on the arterial side, for isolated closed loop circulatory support of separate organ systems. The circulatory support system is suitable for use in minimally-invasive cardiac surgery, using thoracoscopic, port-access or minithoracotomy techniques, or for standard open-chest cardiac surgery.

46 Claims, 21 Drawing Sheets

U.S. PATENT DOCUMENTS

| | | | |
|---|---|---|---|
| 4,494,531 A | 1/1985 | Gianturco | 128/1 R |
| 4,592,340 A | 6/1986 | Boyles | 128/1 |
| 4,705,507 A | 11/1987 | Boyles | 604/101 |
| 4,723,549 A | 2/1988 | Wholey et al. | 128/344 |
| 4,793,348 A | 12/1988 | Palmaz | 128/325 |
| 4,817,600 A | 4/1989 | Herms et al. | 128/303 |
| 4,873,978 A | 10/1989 | Ginsburg | 128/345 |
| 4,926,858 A | 5/1990 | Gifford et al. | 606/159 |
| 4,950,226 A | 8/1990 | Barron | 604/8 |
| 4,968,306 A | 11/1990 | Huss et al. | 604/264 |
| 4,969,891 A | 11/1990 | Gewertz | 606/200 |
| 5,059,205 A | 10/1991 | El-Nounou et al. | 606/200 |
| 5,090,960 A * | 2/1992 | Don Michael | 604/101 |
| 5,108,418 A | 4/1992 | Lefebvre | 606/200 |
| 5,108,419 A | 4/1992 | Reger et al. | 606/200 |
| 5,129,883 A | 7/1992 | Black | 604/101 |
| 5,135,474 A | 8/1992 | Swan | 604/8 |
| 5,152,777 A | 10/1992 | Goldberg et al. | 606/200 |
| 5,163,905 A | 11/1992 | Don Michael | 604/101 |
| 5,167,628 A | 12/1992 | Boyles | 604/101 |
| 5,176,638 A | 1/1993 | Don Michael | 604/101 |
| 5,195,955 A | 3/1993 | Don Michael | 604/102 |
| 5,216,032 A | 6/1993 | Manning | 514/718 |
| 5,222,941 A | 6/1993 | Don Michael | 604/101 |
| 5,306,249 A | 4/1994 | Don Michel | 604/101 |
| 5,308,320 A | 5/1994 | Safar et al. | 604/4 |
| 5,312,344 A * | 5/1994 | Grinfield et al. | 604/101 |
| 5,314,409 A * | 5/1994 | Sarosiek et al. | 604/101 |
| 5,324,304 A | 6/1994 | Rasmussen | 606/200 |
| 5,330,433 A | 7/1994 | Fonger et al. | 604/164 |
| 5,334,142 A | 8/1994 | Paradis | 604/53 |
| 5,342,306 A | 8/1994 | Don Michael | 604/101 |
| 5,354,288 A | 10/1994 | Cosgrove | 604/264 |
| 5,368,555 A | 11/1994 | Sussman et al. | |
| 5,375,612 A | 12/1994 | Cottenceau et al. | 128/899 |
| 5,380,284 A | 1/1995 | Don Michel | 601/101 |
| 5,383,854 A * | 1/1995 | Safar et al. | 604/98 |
| 5,413,558 A | 5/1995 | Paradis | 604/101 |
| 5,415,630 A | 5/1995 | Gory et al. | 604/53 |
| 5,433,700 A | 7/1995 | Peters | 604/4 |
| 5,437,633 A | 8/1995 | Manning | 604/53 |
| 5,451,207 A | 9/1995 | Yock | 604/53 |
| 5,458,574 A | 10/1995 | Machold et al. | 604/101 |
| 5,478,309 A | 12/1995 | Sweezer et al. | 604/4 |
| 5,484,412 A * | 1/1996 | Pierpont | 604/101 |
| 5,496,277 A | 3/1996 | Termin et al. | 604/104 |
| 5,531,776 A | 7/1996 | Ward et al. | 607/105 |
| 5,549,626 A | 8/1996 | Miller et al. | 606/200 |
| 5,584,803 A | 12/1996 | Stevens et al. | 604/4 |
| 5,599,329 A | 2/1997 | Gabbay | 604/284 |
| 5,616,137 A | 4/1997 | Lindsay | 604/264 |
| 5,662,671 A | 9/1997 | Barbut et al. | 606/170 |
| 5,678,570 A | 10/1997 | Manning | 128/897 |
| 5,685,865 A | 11/1997 | Cosgrove et al. | 604/239 |
| 5,695,457 A | 12/1997 | St. Goar et al. | 604/4 |
| 5,697,905 A | 12/1997 | d'Ambrosio | 604/96 |
| 5,702,368 A | 12/1997 | Stevens et al. | 604/171 |
| 5,716,318 A | 2/1998 | Manning | 600/16 |
| 5,725,496 A | 3/1998 | Peters | 604/49 |
| 5,738,649 A | 4/1998 | Macoviak | 604/43 |
| 5,755,687 A | 5/1998 | Donlon et al. | 604/53 |
| 5,755,784 A | 5/1998 | Jarvik | 623/3 |
| 5,762,624 A * | 6/1998 | Peters | 604/4 |
| 5,769,870 A | 6/1998 | Salahieh et al. | 606/198 |
| 5,792,094 A | 8/1998 | Stevens et al. | 604/4 |
| 5,795,325 A | 8/1998 | Valley et al. | 604/53 |
| 5,797,933 A | 8/1998 | Snow et al. | 606/151 |
| 5,800,375 A | 9/1998 | Sweezer et al. | 604/4 |
| 5,807,318 A * | 9/1998 | St. Goar et al. | 604/53 |
| 5,810,757 A | 9/1998 | Sweezer, Jr. et al. | 604/4 |
| 5,814,016 A | 9/1998 | Valley et al. | 604/96 |
| 5,817,113 A | 10/1998 | Gifford et al. | 606/153 |
| 5,820,593 A | 10/1998 | Safar et al. | 604/96 |
| 5,827,237 A | 10/1998 | Macoviak et al. | 604/246 |
| 5,833,671 A | 11/1998 | Macoviak et al. | 604/247 |
| 5,846,260 A | 12/1998 | Maahs | 606/200 |
| 5,879,316 A | 3/1999 | Safar et al. | 604/4 |
| 5,893,841 A | 4/1999 | Glickman | 604/101 |
| 5,904,697 A | 5/1999 | Gifford et al. | 606/155 |
| 5,906,588 A * | 5/1999 | Safar et al. | 604/64 |
| 6,083,198 A * | 7/2000 | Afzal | 640/101.01 |
| 6,190,357 B1 * | 2/2001 | Ferrari et al. | 604/102.01 |
| 6,248,086 B1 * | 6/2001 | Sweezer et al. | 604/4.01 |

OTHER PUBLICATIONS

Barbut et al., "Aortic Atheromatosis and Risks of Cerebral Embolization," *J Card & Vasc Anesth*; vol. 10, No. 1,: pp 24–30 (1996).

Barbut et al., "Aortic Atheroma is Related to Outcome but not Numbers of Emboli During Coronary Bypass," *Ann Thorac Surg*; 64:454–9 (1997).

Roach et al., "Adverse Cerebral Outcomes After Coronary Artery Bypass Surgery," *N Engl J Med*, vol. 335, No. 25; pp. 1857–1863 (1996).

Aberg, "Signs of Brain Cell Injury During Open Heart Operations: Past and Present," *Ann Thorac Surg*; 59:1312–5 (1995).

Murkin, "The Role of CPB Management in Neurobehavioral Outcomes After Cardiac Surgery," *Ann Thorac Surg*; 59:1308–11 (1995).

Mills, "Risk Factors for Cerebral Injury and Cardiac Surgery," *Ann Thorac Surg* 1995, 59:1296–9.

Murkin et al., "Statement of Consensus on Assessment of Neurobehavioral Outcomes After Cardiac Surgery," *Ann Thorac Surg*; 59:1289–95 (1995).

Sherman et al., "Heart–Brain Interactions: Neurocardiology Comes of Age," *Mayo Clin Proc*; 62:1158–1160 (1987).

van der Linden, "Cerebral Hemodynamics After Low–Flow Versus No–Flow Procedures," *Ann Thorac Surg*; 59:1321–5 (1995).

Newman et al., "Predictors of Cognitive Decline After Cardiac Operation," *Ann Thorac Surg*; 59:1326–30 (1995).

Venn et al., "Cardiopulmonary Bypass: Perioperative Cerebral Blood Flow and Postoperative Cognitive Deficit," *Ann Thorac Surg*; 59:1331–5 (1995).

Blauth, "Macroemboli and Microemboli During Cardiopulmonary Bypass," *Ann Thorac Surg*; 59:1300–3 (1995).

Rogers AT, Neurological Effects of Cardiopulmonary Bypass; Cardiopulmonary Bypass Principles and Practice; Gravlee GP, 21:542.

Erath et al., "Balloon Catheter Occlusion of the Ascending Aorta," *Ann Thorac Surg*; 35:560–1 (1983).

Cosgrove DM, "Management of the Calcified Aorta: and Alternative Method of Occlussion," *Ann Thor Surg*; 36:718–719 (1983).

Baxter Research Medical, RMI Dispersion™ Aortic Cannula, Advertisement (1998).

Braekken et al. "Cerebral Microembolic Signals During Cardipulmonary Bypass Surgery. Frequency, Time of Occurrence, and Association with Patient and Surgical Characteristics." *Stroke*; 1988–92. (1997).

Okiya et al "Utilization of Triple Lumen Balloon Catheter for Occlusion of The Ascending Aorta During Distal Aortic Arch Surgery With Hypothermic Retrograde Cerebral Circulation Technique Through Left Thorocotomy." *J Card Surg*; 10:699–702 (1995).

Rubenstein et al. "Percutaneous Aortic Balloon Occlusion." *Surg Gynecol Obstet*; 164:561–563 (1987).

Muehrcke et al. "Flow Characteristics of Aortic Cannulae." *J Card Surg*; 10:514–519 (1995).

Robicsek, "Administration of Hypothermic Cardioplegia in the Presence of Aortic Regurgitation." *Ann Thorac Surg.* Feb; 39(2):192–3 (1985).

\* cited by examiner

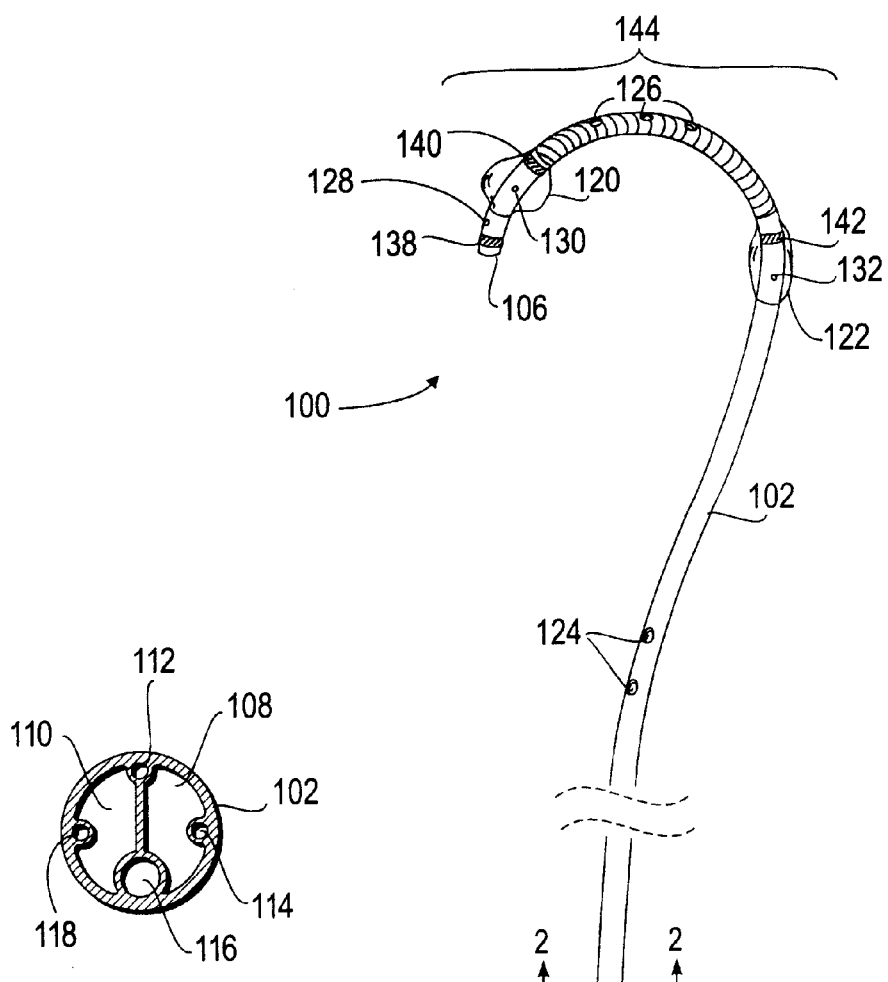
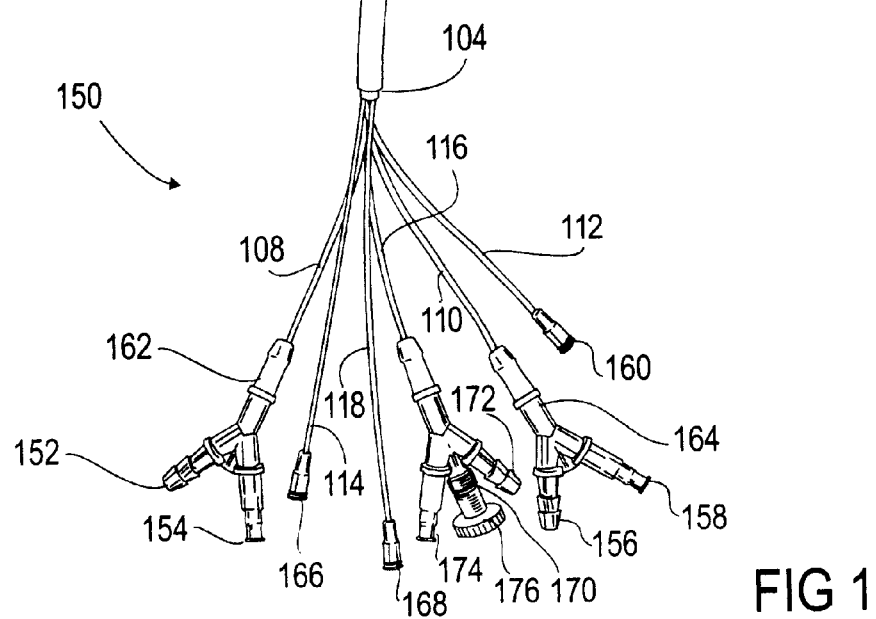
FIG 2
FIG 1

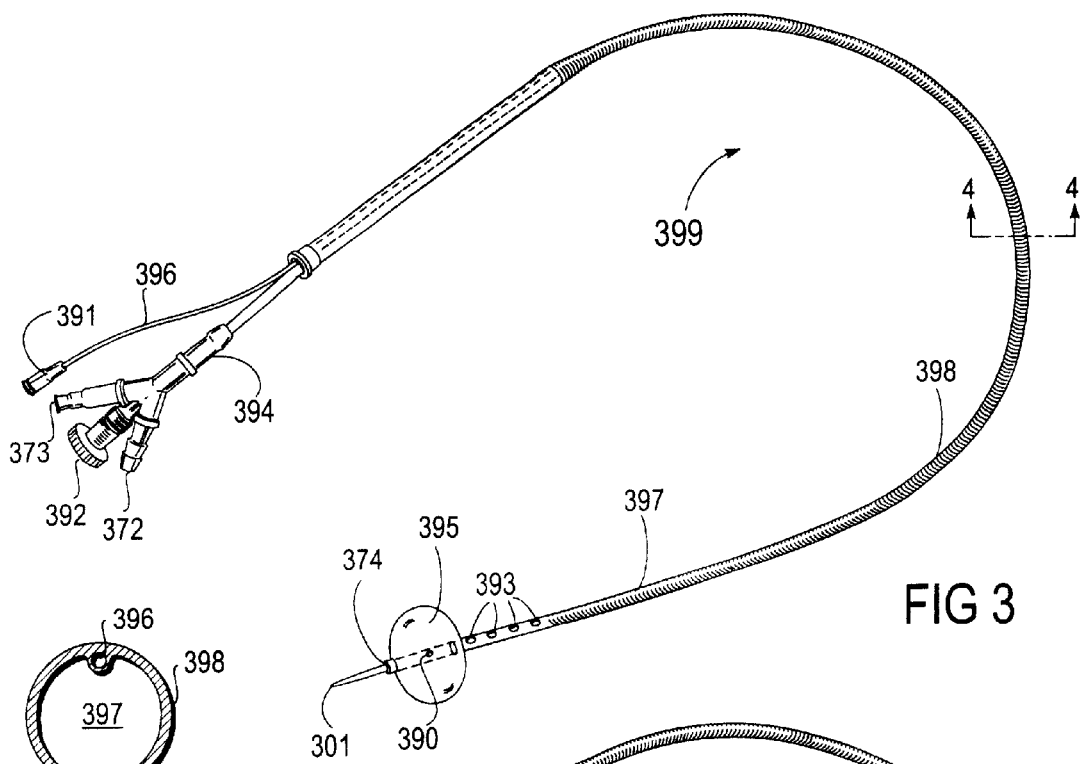
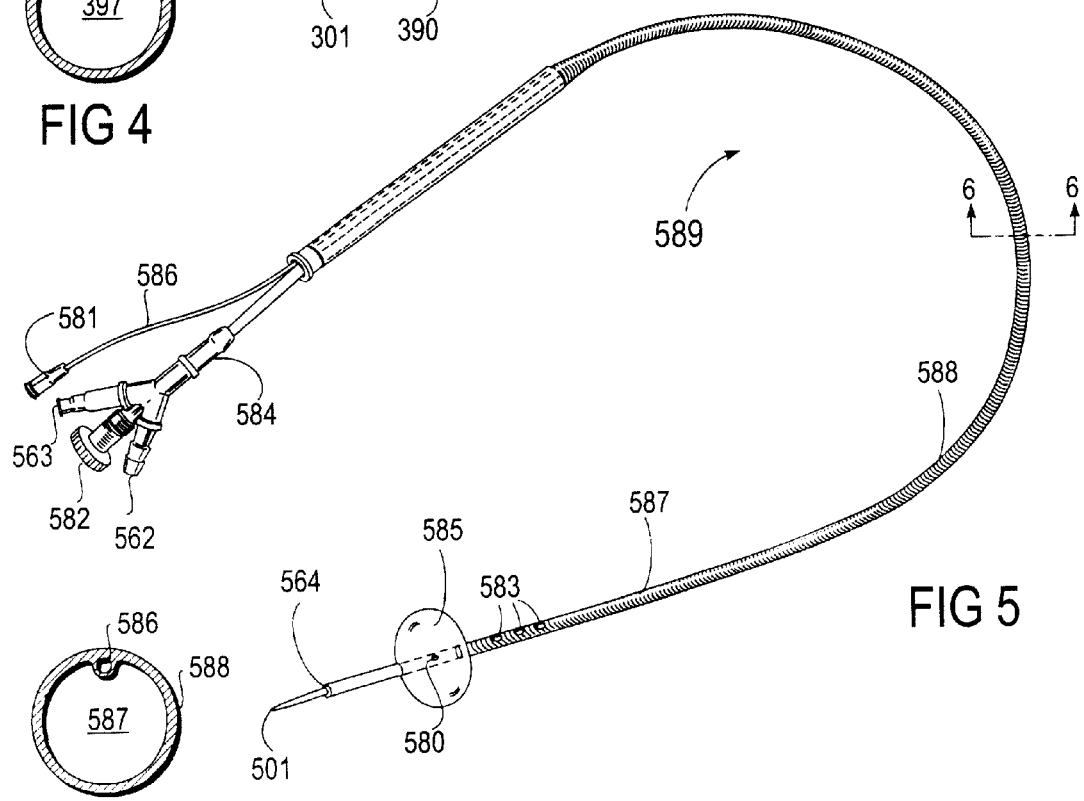

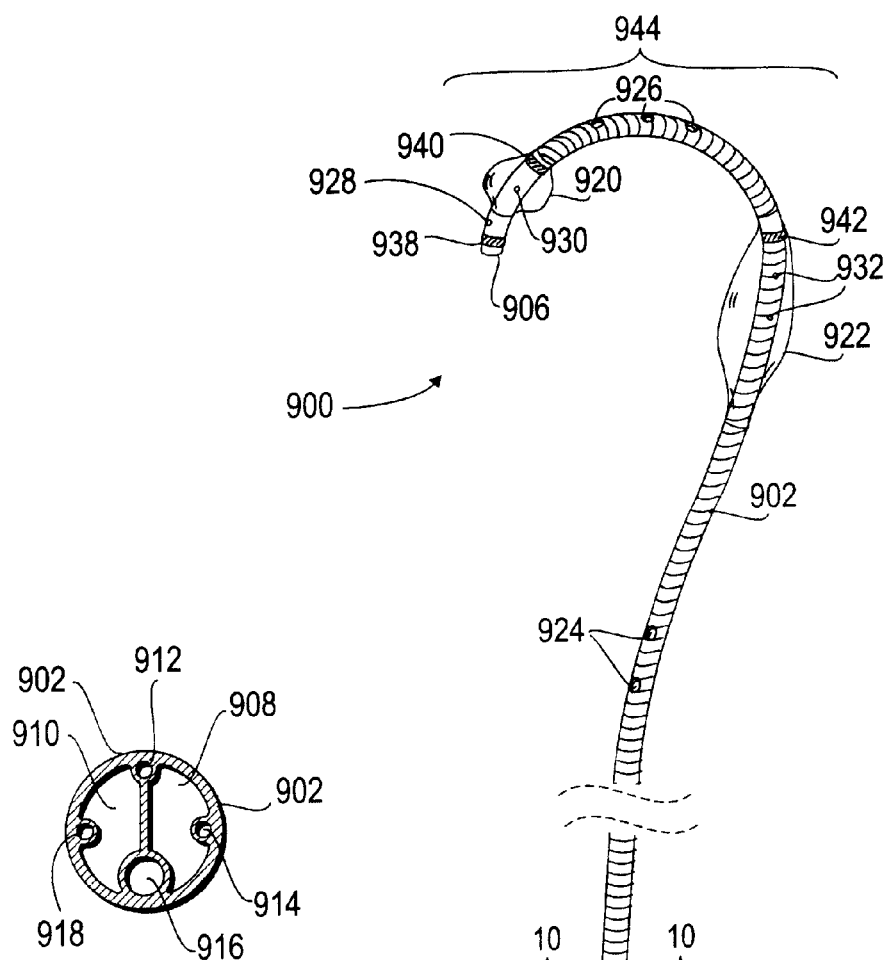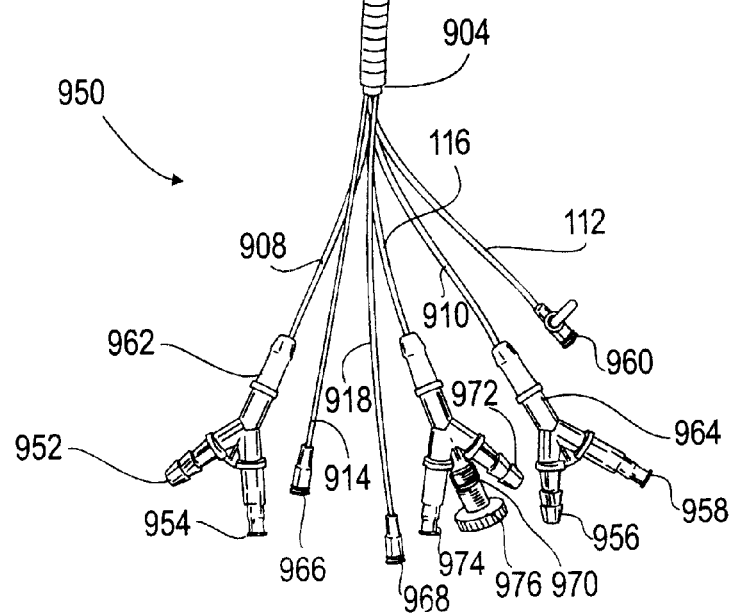
FIG 10
FIG 9

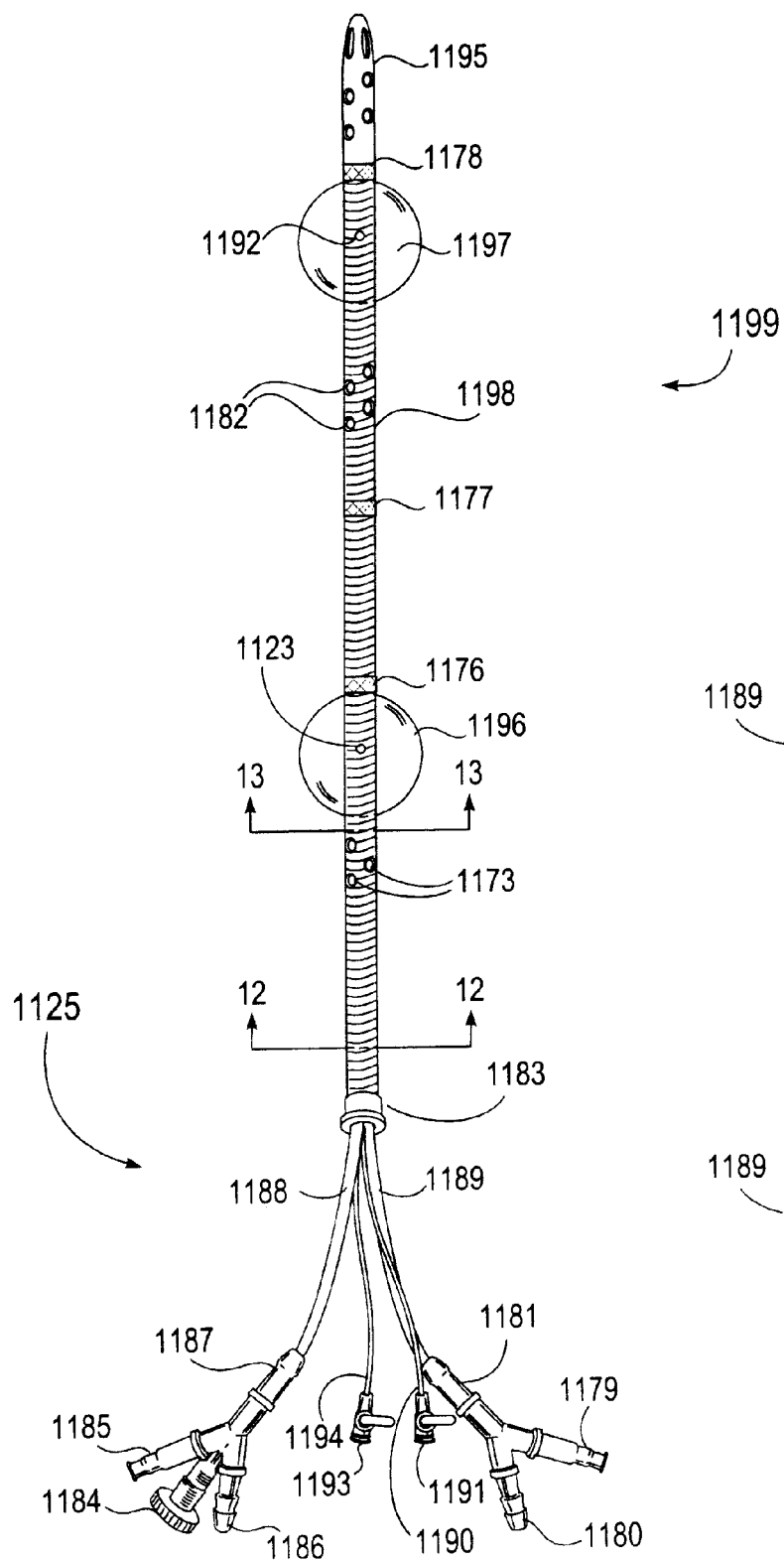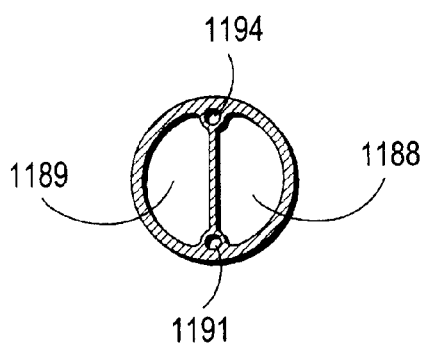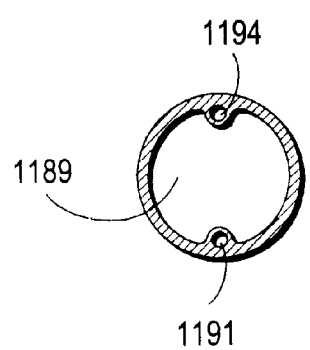
FIG 11
FIG 12
FIG 13

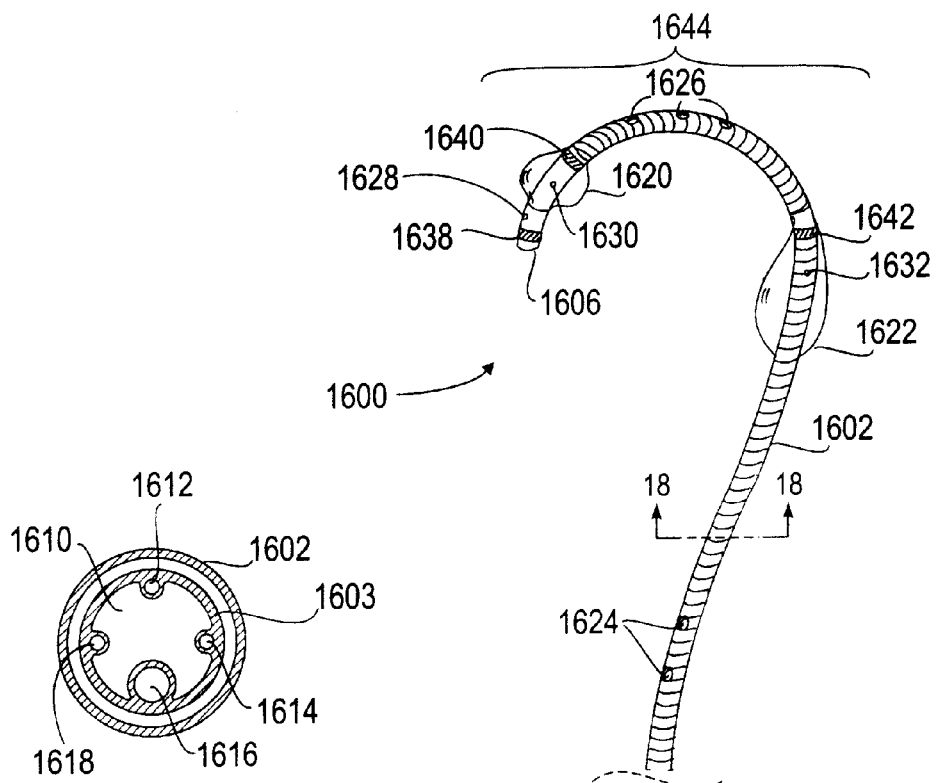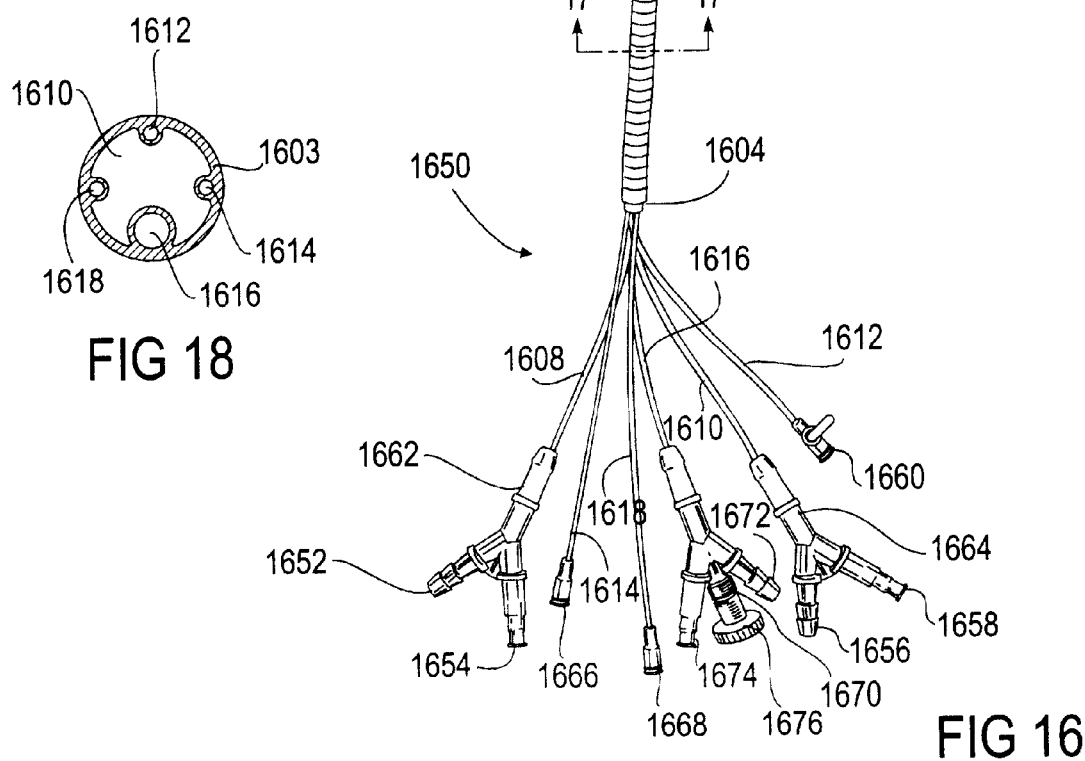
FIG 17
FIG 18
FIG 16

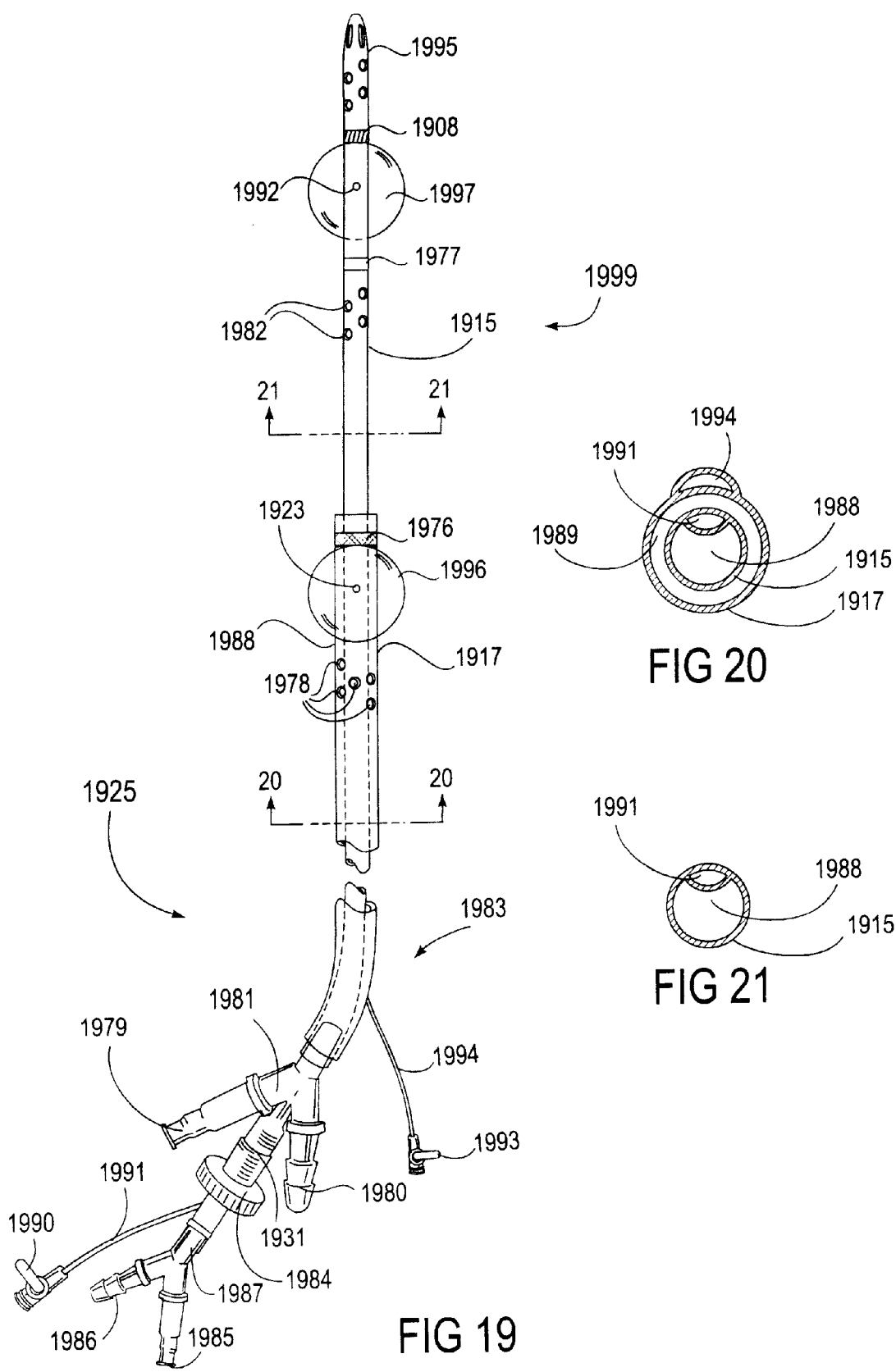

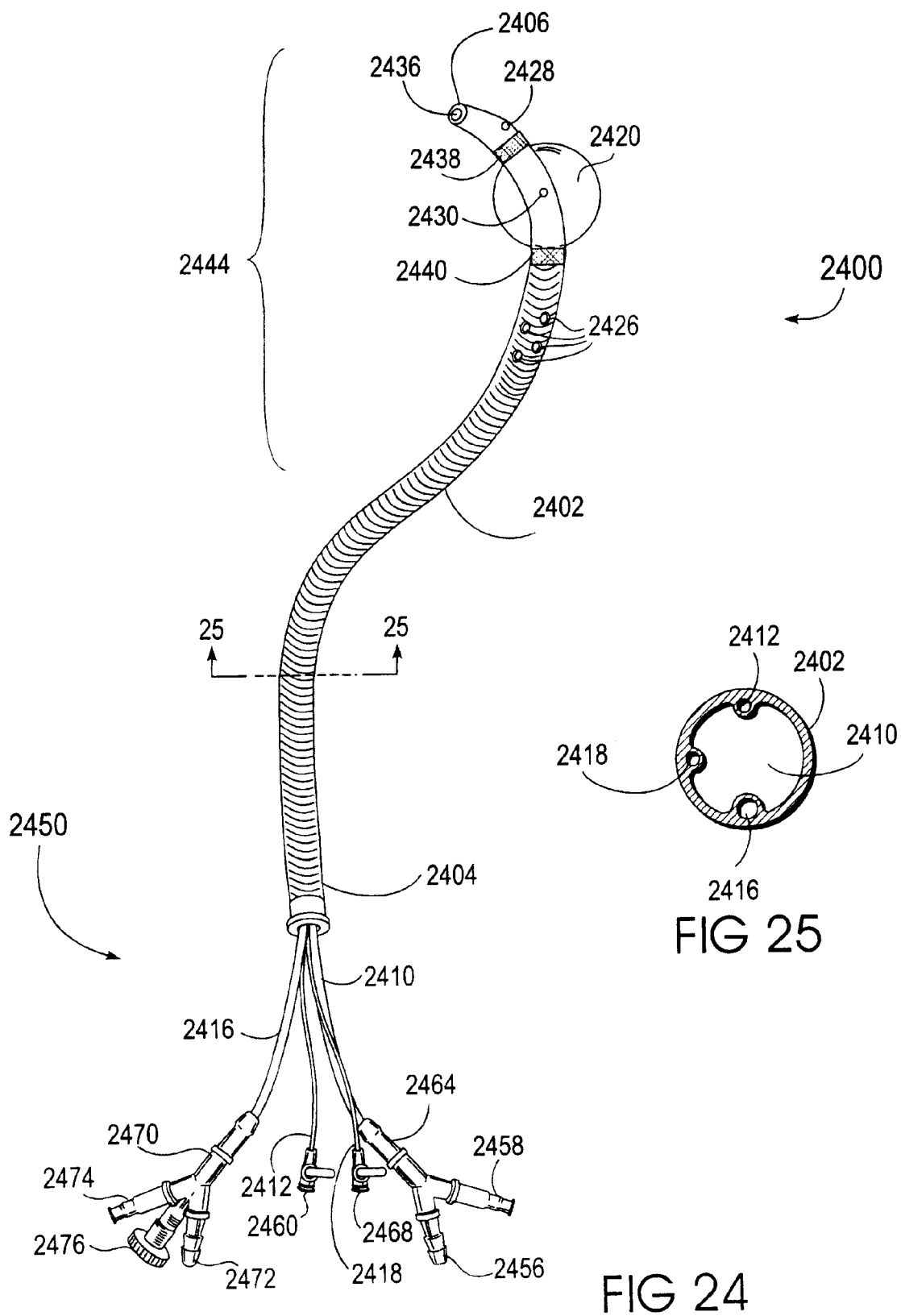

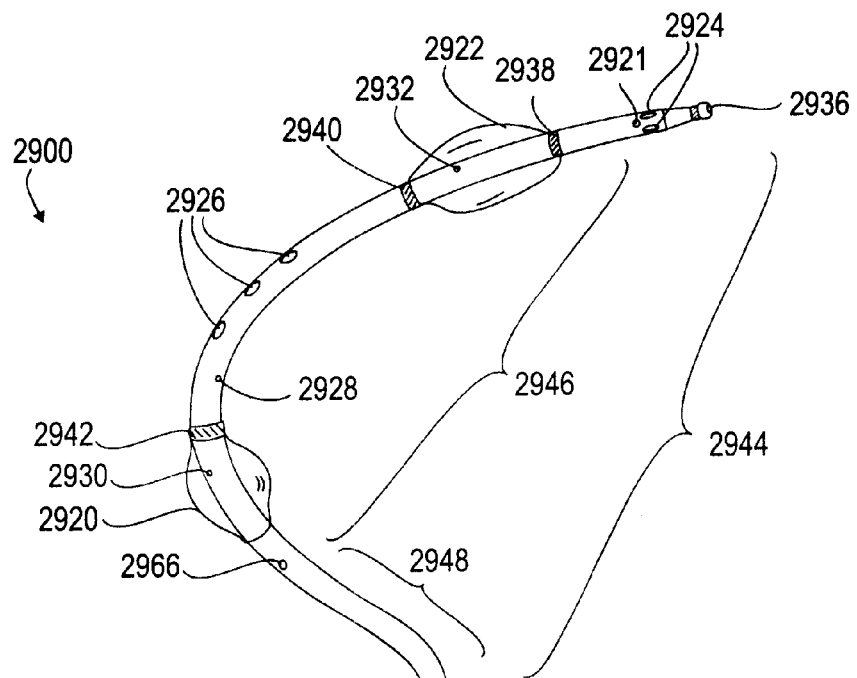
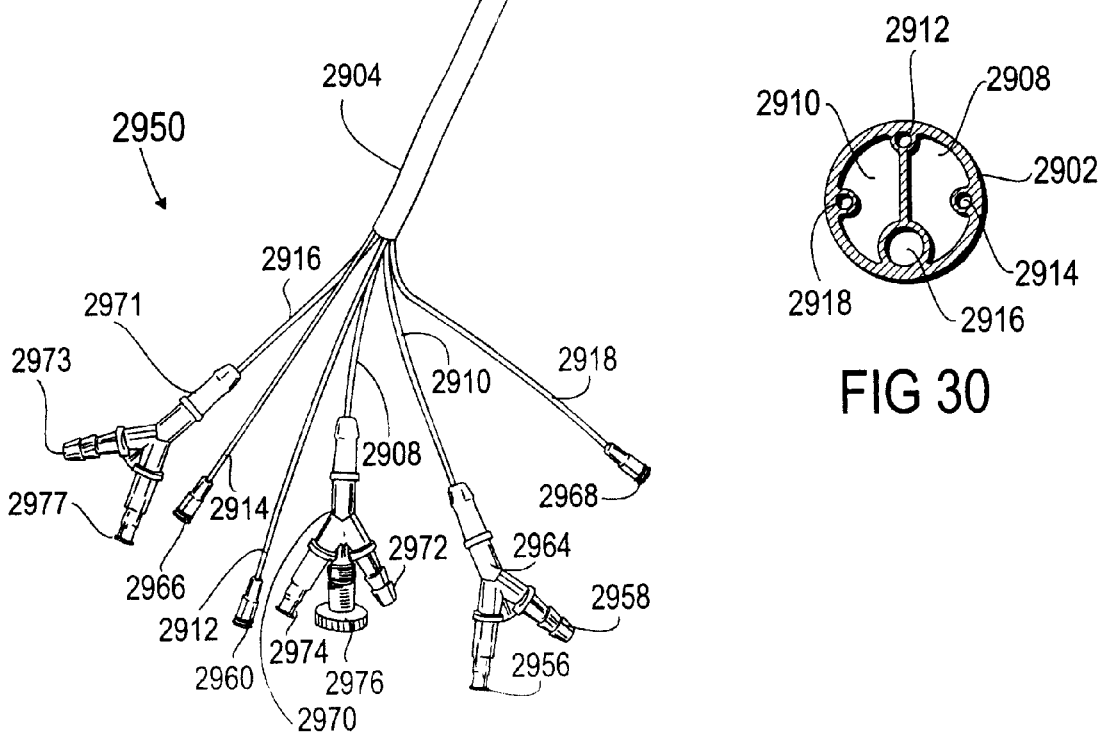
FIG 29
FIG 30

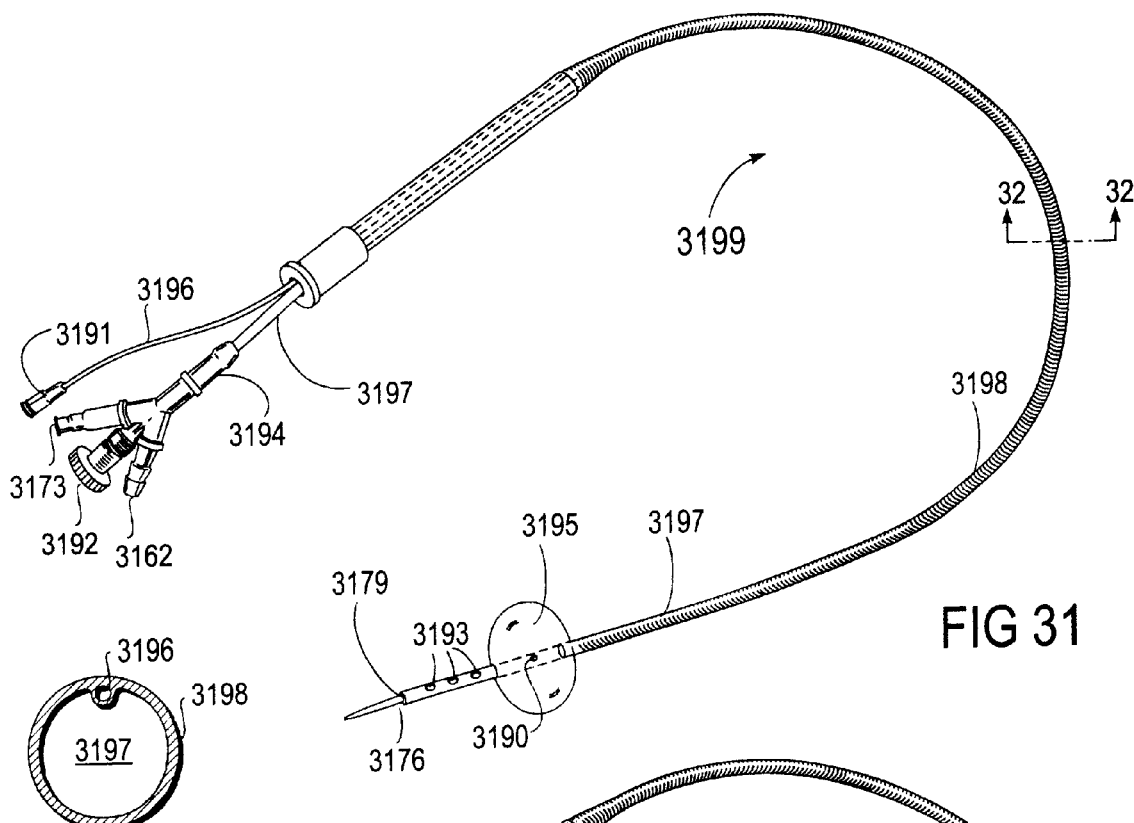
FIG 31
FIG 32
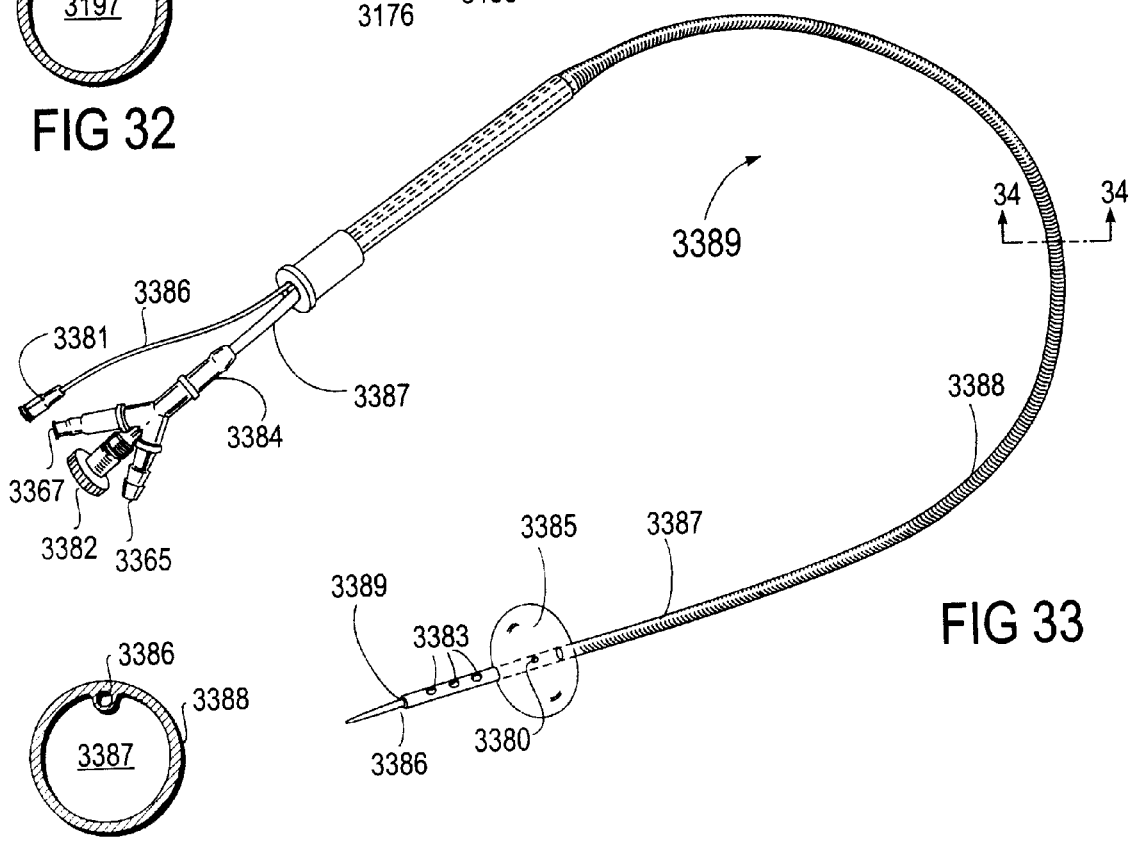
FIG 33
FIG 34

CIRCULATORY SUPPORT SYSTEM AND METHOD OF USE FOR ISOLATED SEGMENTAL PERFUSION

This application claims the benefit of Provisional Application No. 60/084,835 filed May 8, 1998.

FIELD OF THE INVENTION

The present invention relates generally to circulatory support systems and cardiopulmonary bypass systems. More particularly, it relates to a circulatory support system and method of use for isolating organ systems for separate closed loop perfusion.

BACKGROUND OF THE INVENTION

Circulatory support systems are used in many different medical settings to supplement or to replace the pumping function of a patient's heart. Applications of circulatory support systems and methods include, inter alia, augmenting cardiac output in patients with a failing heart, resuscitating victims of severe trauma or injury, and supporting a patient's circulatory functions during surgery.

One particular type of circulatory support system, known as a cardiopulmonary bypass (CPB) system, is used to temporarily replace the functions of the heart and the lungs by supplying a flow of oxygenated blood to the patient's circulatory system. The CPB system drains deoxygenated blood from the patient's venous system, passes it through a blood oxygenator, and pumps the oxygenated blood back into the patient's arterial system. CPB systems may be configured for direct cannulation of the inferior and superior vena cava or the right atrium and the aorta, or they may be configured for peripheral cannulation through the femoral vein or jugular vein and the femoral artery. The cardiopulmonary bypass system allows the patient's heart to be temporarily stopped, for example by cardioplegic arrest, hypothermic arrest or fibrillation, for performing a variety of cardiothoracic surgical procedures.

Previous CPB systems have generally been configured to provide a single circulatory loop for supplying the entire body with oxygenated blood from a single CPB pump. Thus, all organ systems of the body receive oxygenated blood at the same pressure and temperature and with the same blood composition. This single-loop configuration has significant limitations in many medical circumstances. It has been found, for instance, that the optimal perfusion temperature for organ preservation during prolonged circulatory support is different for different organs of the body. Likewise, different chemical compositions of the blood are beneficial for preservation of different organ systems. For optimal preservation of all the organ systems within the body, it would be desirable to be able to selectively perfuse different organ systems with different perfusates, which have been optimized for each of the organ systems.

U.S. Pat. Nos. 5,308,320, 5,383,854, 5,820,593 and 5,879,316 by Peter Safar, S. William Stezoski and Miroslav Klain, describe a cardiopulmonary bypass system capable of segmenting a patient's aorta and for selectively perfusing the different segments of the aorta with perfusates of different temperatures or chemical compositions. Other U.S. patents that address the concept of selective aortic perfusion include commonly owned, copending patent applications; 08/909,293, filed Aug. 11, 1997; 08/909,380, filed Aug. 11, 1997, and 09/152,589 filed Aug. 11, 1998 by Safar et al.; and U.S. Pat. No. 5,738,649 and commonly owned copending patent application 09/060,412 filed Apr. 14, 1998 by John A. Macoviak; and U.S. Pat. Nos. 5,827,237 and 5,833,671 by John A. Macoviak and Michael Ross and commonly owned copending patent application 08/665,636, filed Jun. 17, 1996; filed Jun. 18, 1996, by John A. Macoviak and Michael Ross; and 60/067,945, filed Dec. 8, 1997, by Bresnahan et al. These patent applications and all other patents referred to herein are hereby incorporated by reference in their entirety. The balloon catheter of Safar et al. may be introduced into the patient's aorta from a peripheral entry point, such as the femoral artery or the subclavian artery, or it may be introduced by a direct puncture in the patient's aorta during open chest surgery.

The previously described system, however, does not isolate the segments of the circulatory system from one another on the venous side of the circulatory system because the blood from each of the segments mingles together. Thus, any organ preserving temperature gradients, chemicals or therapeutic agents introduced into one of the segments will eventually mix with and be diluted into the entire systemic blood supply. In many circumstances it would be desirable to at least partially segment blood flow on the venous side of the circulatory system. For example, when administering anesthesia to a patient during surgery, it may be desirable to limit the flow of the anesthetic to the cerebral circulation only and to avoid dilution of the anesthetic in the systemic blood supply, and even to recirculate the anesthetic to the cerebral circulation. As another example, when administering a therapeutic agent that is very costly or which has systemic, central or specific organ toxicity or other undesirable effects, it may be desirable to limit the flow of the therapeutic agent to the target organs as much as possible without it entering the systemic blood supply such as gene therapy, viral vectors protein plasmids and angiogenic genes. As a third example, when performing segmented selective perfusion combined with hypothermic organ preservation, it would be desirable to isolate the segments of the circulatory system on the venous side to allow more precise and efficient temperature control within each circulatory loop. It would be desirable, therefore, to provide a circulatory support system or cardiopulmonary bypass system that allows segmentation of the circulatory system on the venous side, as well as on the arterial side, for isolated closed loop circulatory support of separate organ systems. Such a closed loop circulatory support system may be used to supply the entire body; with blood or other fluids through a plurality of isolated circulatory loops when the heart is not pumping. Alternatively, the closed loop circulatory support system may be used to create a single circulatory loop for supplying a single segment or organ system of the body with blood or other fluids while the beating heart supplies blood to the remainder of the body.

A plethora of known and newly discovered organ preserving chemicals and therapeutic agents are suitable for use with the circulatory support system of the present invention. Among these are natural and artificial blood substitutes or oxygen carriers, such as free hemoglobin, PERFLUBRON, and perfluorocarbons, and hemoglobin modifiers, such as RSR-13 (Allos Therapeutics), that increase oxygen delivery from blood to tissues. Also among these are neuroprotective agents, which have been the subject of intensive research in recent years. Promising neuroprotective agents include $Na^+$ blockers, glutamate inhibitors, nitric oxide inhibitors and radical scavengers. A thorough treatment of this subject can be found in the book *Neuroprotective Agents*, published by the New York Academy of Sciences. Possible therapeutic agents include, inter alia, thrombolytic agents, such as tPA, streptokinase and urokinase as well as gene therapy including angiogenic genes.

SUMMARY OF THE INVENTION

The circulatory support system of the present invention generally includes one or more venous cannulae for draining blood from the venous side of the patient's circulatory system, one or more arterial cannulae for perfusing the arterial side of the patient's circulatory system, and one or more blood circulation pumps connected between the venous cannulae and the arterial cannulae. The arterial cannulae and the venous cannulae of the circulatory support system may take one of several possible configurations. The circulatory support system is configured to segment a patient's circulatory system into one or more isolated circulatory loops. The circulatory loops may be isolated from one another and/or from the remainder of the patient's circulatory system on the venous side, as well as on the arterial side, for isolated closed loop circulatory support of separate organ systems. The circulatory support system of the present invention is suitable for use in minimally-invasive cardiac surgery, using thoracoscopic, port-access or minithoracotomy techniques, or for standard open-chest cardiac surgery.

Also disclosed is a method for circulatory support and for cardiopulmonary bypass using differential perfusion and/or isolated segmental perfusion of the circulatory system. According to the method, a patient's circulatory system is segmented into two or more regions that are perfused with perfusate at different temperatures and/or different chemical compositions and/or different flow rates and/or different pressures. The regions may be isolated from one another and/or from the remainder of the patient's circulatory system on the venous side, as well as on the arterial side, for isolated closed loop circulatory support of separate organ systems.

In one variant of the method, a cerebral loop, a cardiac loop and a corporeal loop are created. A first fluid, preferably containing oxygenated blood, is circulated to the cerebral loop at a relatively low temperature of approximately 32° C. or lower for deep protective hypothermia of the brain. Neuroprotective agents may be added to the first fluid to enhance the protection. A second fluid, which may include a cardioplegic agent, is circulated to the cardiac loop at a moderate temperature between 32° C. and 37° C. for mild hypoihermia of the heart to protect the myocardium, while avoiding arrhythmias that can be caused by deep hypothermia. A third fluid, preferably containing oxygenated blood, is circulated to the corporeal loop at approximately 37° C. for normothermic support of the remainder of the body. The venous side of the circulatory system may likewise be divided three ways so that the cerebral loop, cardiac loop and corporeal loop which are at least partially isolated from one another. Alternatively, the venous side of the circulatory system may be divided two ways so that the cardiac loop combines with either the cerebral loop or corporeal loop on the venous side, or the flow from all three loops may be allowed to commingle on the venous side of the circulatory system.

The use of differential perfusion according to this method provides several other clinical advantages in addition to those discussed above. The use of differing degrees of hypothermia allows optimal protection of the brain and of the heart during cardiopulmonary support, while decreasing the likelihood of complications. This method reduces the thermal mass of the tissue that must be cooled and rewarmed during the procedure. In addition, normothermic corporeal circulation provides a large reservoir of stored thermal energy for assisting in rewarming the heart and the brain at the end of the procedure. Both of these factors will result in decreasing the procedure time for surgery requiring cardiopulmonary bypass.

Still other clinical advantages exist with a closed loop circulatory system of the present invention. By isolating the cerebral, myocardial and corporeal circulation on the venous side (outputs) as well as the arterial side (inputs), isolated measurements in the aortic arch, aortic root, and corporeal circulation can be monitored in relation to the superior vena cava, right atrium and inferior vena cava respectively. This relationship will enable the clinician to determine oxygen saturation in the cerebral loop and in the corporeal loop to better manage the patient during the surgical procedure.

BRIEF DESCRIPTION OF THE DRAWINGS

FIG. 1 illustrates a side view of an aortic catheter according to the present invention with a catheter shaft configured for retrograde deployment via femoral artery access.

FIG. 2 is a magnified lateral cross section of the aortic catheter of FIG. 1 taken along line 2—2 showing the multi-lumen arrangement of the catheter shaft.

FIG. 3 illustrates a side view of a superior vena cava cannula according to the present invention with a tubular shaft configured for introduction into a patient's venous system through the jugular vein or other peripheral artery.

FIG. 4 is a magnified lateral cross sectional of the superior vena cava cannula of FIG. 3 taken along line 4—4 in FIG. 3.

FIG. 5 illustrates a side view of an inferior vena cava cannula according to the present invention with a tubular shaft configured for introduction into a patient's venous system through the femoral vein or other peripheral artery.

FIG. 6 is a magnified lateral cross sectional of the inferior vena cava cannula of FIG. 5 taken along line 6—6 in FIG. 5.

FIG. 9 illustrates a side view of an aortic catheter according to the present invention with a catheter shaft configured for retrograde deployment via femoral artery access.

FIG. 10 is a magnified lateral cross section of the aortic catheter of FIG. 9 taken along line 10—10 showing the multi-lumen arrangement of the catheter shaft.

FIG. 11 illustrates a side view of a dual lumen venous drainage cannula of the present invention configured for introduction through the patient's inferior vena cava via the femoral vein or other suitable venous access point in the lower extremities.

FIG. 12 is a magnified lateral cross section of the venous drainage cannula taken along line 12—12 of FIG. 11.

FIG. 13 is a magnified lateral cross section of the venous drainage cannula taken along line 13—13 of FIG. 11.

FIG. 16 illustrates a side view of an aortic catheter according to the present invention with a coaxial catheter shaft configured for retrograde deployment via femoral artery access.

FIG. 17 is a magnified lateral cross section of the aortic catheter of FIG. 16 taken along line 17—17 showing the multi-lumen coaxial arrangement of the catheter shaft.

FIG. 18 is a magnified lateral cross-section of the aortic catheter of FIG. 16 taken along line 18—18 showing the multi-lumen arrangement of the catheter shaft.

FIG. 19 illustrates a side view of a coaxial dual lumen venous drainage cannula of the present invention configured for introduction through the patient's inferior vena cava via the femoral vein or other suitable venous access point in the lower extremities.

FIG. 20 is a magnified lateral cross section of the coaxial dual lumen venous drainage cannula taken along line 20—20 of FIG. 19.

FIG. 21 is a magnified lateral cross section of the coaxial dual lumen venous drainage cannula taken along line 21—21 of FIG. 19.

FIG. 24 illustrates an aortic arch perfusion cannula of the present invention configured for introduction into the aortic arch through peripheral arterial access in one of the upper extremities, such as the left or right subclavian artery, axillary artery or brachial artery.

FIG. 25 is a magnified lateral cross section of the aortic arch perfusion cannula of FIG. 24 taken along line 25—25 of FIG. 24 showing the multi-lumen arrangement of the catheter shaft.

FIG. 29 illustrates a side view of a dual-balloon, selective, central arterial perfusion cannula configured for antegrade introduction into the patient's aortic arch via a direct puncture or incision in the ascending aorta.

FIG. 30 is a magnified lateral cross section of the aortic catheter of FIG. 29 taken along line 30—30 in FIG. 29 illustrating the multi-lumen arrangement of the aortic catheter.

FIG. 31 illustrates a side view of the central superior vena cava cannula of the present invention configured for introduction into the patient's superior vena cava via an incision in the right atrium.

FIG. 32 is a magnified lateral cross-section of the central superior vena cava cannula taken along line 32—32 of FIG. 31.

FIG. 33 illustrates a side view of the central inferior vena cava cannula of the present invention configured for introduction into the patient's inferior vena cava through the same or another incision in the right atrium.

FIG. 34 is a magnified lateral cross-section of the central superior vena cava cannula taken along line 33—33 of FIG. 33.

DETAILED DESCRIPTION OF THE INVENTION

Figure 7:
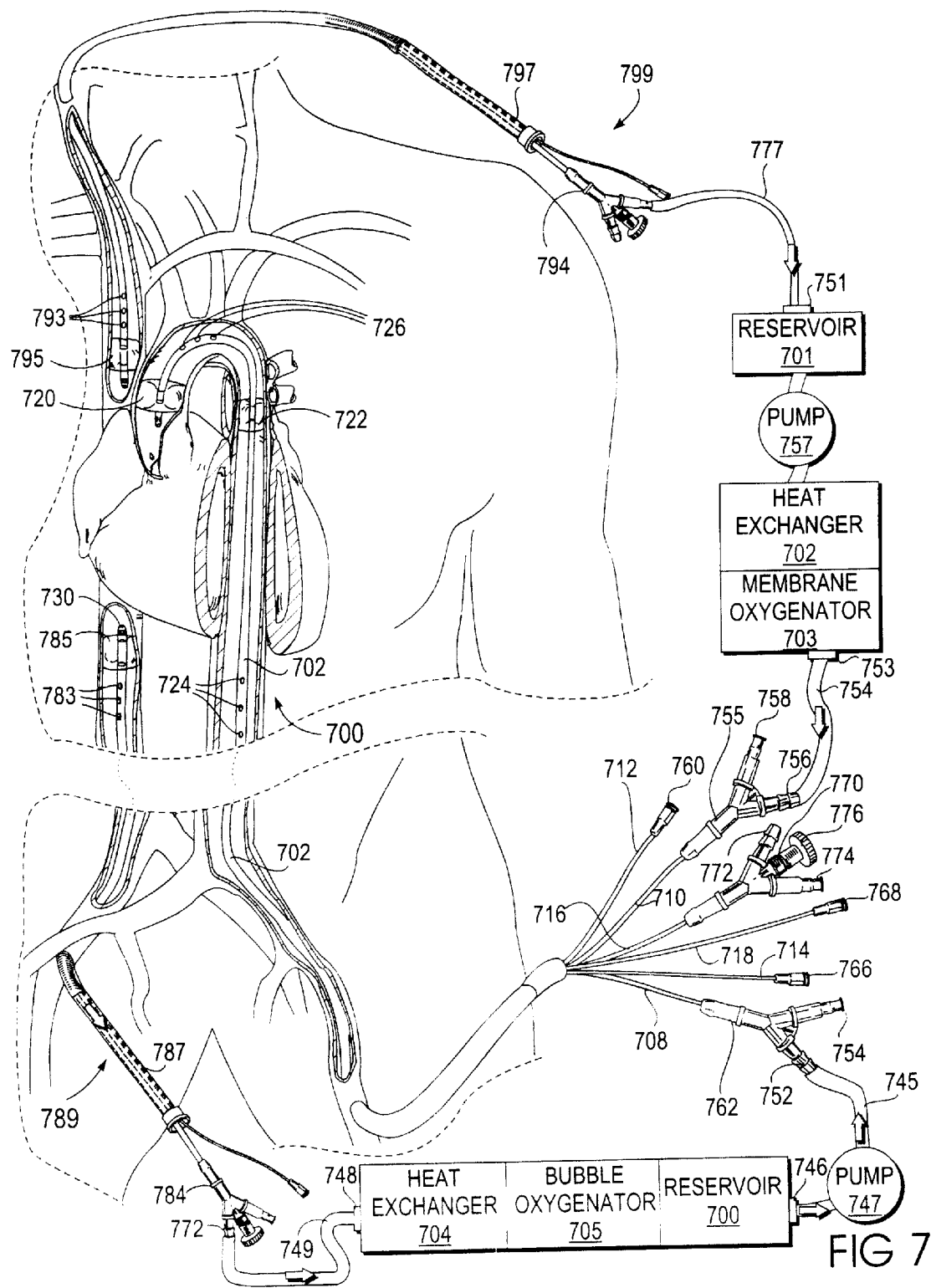
FIG. 7 is a schematic illustration depicting a first embodiment of the present invention configured for selective, isolated, dual-loop perfusion of a patient's circulatory system.

The circulatory support system of the present invention generally comprises one or more arterial cannulae to enable the segmented perfusion of the patient's circulatory system. On the arterial side, one or more venous cannulae for enable segmented draining of the patient's circulatory system on the venous side, and one or more blood circulation pumps connect between the venous cannulae and the arterial cannulae. Preferably, the circulatory support system will also include one or more blood oxygenators and one or more heat exchangers for conditioning the patient's blood. The circulatory support system is configured to segment a patient's circulatory system into one or more isolated circulatory loops. The circulatory loops are isolated from one another and/or from the remainder of the patient's circulatory system on the venous side, as well as on the arterial side, for isolated closed loop circulatory support of separate organ systems.

FIGS. 1 through 7 illustrate a first embodiment of the present invention. FIG. 1 illustrates a side view of the aortic catheter 100 according to the present invention with a catheter shaft 102 configured for retrograde deployment via femoral artery access. In order to facilitate placement of the aortic catheter 100 and to improve the stability of the catheter 100 in the proper position in the patient's aorta, a distal region 144 of the catheter shaft 102 may be preshaped with a curve to match the internal curvature of the patient's aortic arch. The curved distal region 144 represents a J-shaped curve of approximately 180 degrees of arc with a radius of curvature of approximately 2 to 4 cm to match the typical curvature of the aortic arch in an adult human patient. In addition, the distal end 106 of the catheter may be skewed slightly up out of the plane of the curve to accommodate the forward angulation of the patient's ascending aorta. Additionally, the catheter shaft 102 may be reinforced, particularly in the curved distal region 144, for example with braided or coiled wire, to further improve the stability of the catheter 100 in the proper position in the patient's aorta.

Illustrated in FIG. 2, is a magnified lateral cross section of the aortic catheter 100 of FIG. 1 taken along line 2—2 showing the multi-lumen arrangement of the catheter shaft 102. The catheter shaft 102 has six lumens: a corporeal perfusion lumen 108, an arch perfusion lumen 110, a first balloon inflation lumen 112, a second balloon inflation lumen 114, a guide wire and cardioplegia lumen 116 and a root pressure lumen 118.

Referring to FIG. 1 the elongated catheter shaft 102 is preferably formed of a flexible thermoplastic material, a thermoplastic elastomer or a thermoset elastomer. The catheter shaft 102 may be fabricated separately by known extrusion methods and joined together end-to-end, for example by heat welding or by adhesive bonding. Alternatively, the catheter shaft 102 may be fabricated by dipping or by composite construction techniques and joined together or the entire catheter shaft 102 may be fabricated integrally. Suitable materials for the elongated catheter shaft 102 include, but are not limited to, polyvinylchloride, polyurethane, polyethylene, polypropylene, polyamides (nylons), polyesters, silicone, latex, and alloys or copolymers thereof, as well as braided, coiled or counterwound wire or filament reinforced composites.

An upstream occlusion member 120 is mounted on the catheter shaft 102 near the distal end 106 of the catheter 100. The upstream occlusion member 120 in this embodiment is in the form of an expandable, inflatable balloon bonded to the catheter shaft 102 by heat welding or with an adhesive. Alternatively, the upstream occlusion member 120 may be in the form of a selectively deployable external catheter valve. For a discussion of other suitable upstream occlusion members as well as the material components thereof, reference is made to commonly owned U.S. Pat. Nos. 5,827,237, and 5,833,671 which have previously been incorporated by reference herein in their entirety and commonly owned copending patent application 09/205,753 filed Dec. 4, 1998, which is herein incorporated by reference. These occlusion members discussed therein are suitable for all embodiments discussed herein in any combination. Suitable materials for the upstream occlusion member 120 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the outer surface of the upstream occlusion member 120 may include a friction increasing coating or texture to increase friction with the aortic wall when deployed. The upstream occlusion member 120 has a deflated state, in which the diameter of the occlusion member 120 is preferably not much larger than the diameter of the catheter shaft 102, and an inflated state, in which the occlusion member 120 expands to a diameter sufficient to occlude blood flow in the ascending aorta of the patient. For use in adult human patients, the inflatable balloon upstream occlusion member 120 preferably has an inflated outer diameter of approximately 1.5 cm to 5.0 cm. Preferably, the inflatable occlusion member 120 has an inflated length that is not significantly longer than its inflated diameter, or more preferably, is shorter than its inflated diameter. This shortened inflated profile allows the upstream occlusion member 120 to be easily placed within the ascending aorta between the coronary arteries and the brachiocephalic artery without any danger of inadvertently occluding either.

A downstream occlusion member 122 is mounted on the catheter shaft 102 at a position proximal to and spaced apart from the upstream occlusion member 120. The downstream anchoring member may be made of the same materials as the upstream anchoring member of different materials and of the same size or a different size. For a complete discussion on the potential sizes and characteristics of the downstream occlusion member, reference is made to commonly owned copending patent application 09/205,753 filed Dec. 4, 1998 which has previously been incorporated by reference. The downstream anchoring members discussed therein are suitable for all embodiments discussed herein in any combination. The distance between the upstream occlusion member 120 and the downstream occlusion member 122 is preferably between 3 and 20 cm, more preferably between 8 and 15 cm, and is chosen so that when the aortic catheter 100 is deployed and the upstream occlusion member 120 is positioned within the ascending aorta between the coronary arteries and the brachiocephalic artery, the downstream occlusion member 122 will be positioned in the descending aorta downstream of the left subclavian artery. The downstream occlusion member 122 in this embodiment is in the form of an expandable, inflatable balloon bonded to the catheter shaft 102 by heat welding or with an adhesive. The downstream occlusion member 122 is more elongate than the upstream occlusion member 120. Suitable materials for the inflatable balloon downstream anchoring member 122 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the outer surface of the downstream anchoring member 122 may include a friction increasing coating or texture to increase friction with the aortic wall when deployed. Alternatively, the downstream occlusion member 122 may be in the form of a selectively deployable valve.

The inflatable downstream occlusion member 122 has a deflated state, in which the diameter of the occlusion member 122 is preferably not much larger than the diameter of the catheter shaft 102, and an inflated state, in which the occlusion member 122 expands to a diameter sufficient to occlude blood flow in the descending aorta of the patient. For use in adult human patients, the downstream occlusion member 122 preferably has an inflated outer diameter of approximately 1.5 cm to 5.0 cm and a length of approximately 1.0 cm to 7.5 cm. The more elongated the occlusion member 122 the greater the anchoring friction against the wall of the descending aorta when the downstream occlusion member 122 is inflated in order to prevent migration of the aortic catheter 100 due to pressure gradients within the aorta during perfusion.

The corporeal perfusion lumen 108 extends through the catheter shaft 102 from the proximal end 104 to one or more corporeal perfusion ports 124 on the exterior of the catheter shaft 102 proximal of the downstream occlusion member 122. The arch perfusion lumen 110 extends through the catheter shaft 102 from the proximal end 104 to one or more arch perfusion ports 126 on the exterior of the catheter shaft 102 between the upstream occlusion member 120 and the downstream occlusion member 122. The first inflation lumen 112 extends through the catheter shaft 102 from the proximal end 104 to a first balloon inflation port 132 residing in the interior of the downstream occlusion member 122. The second balloon inflation lumen 114 extends through the catheter shaft 102 from the proximal end 104 to balloon inflation port 130 residing in the interior of the upstream occlusion member 120. Alternatively, a common balloon inflation lumen can serve to simultaneously inflate and deflate both the upstream occlusion member 120 and the downstream occlusion member 122. When a common inflation lumen is implemented an arch monitoring lumen (not shown) may be incorporated having an arch monitoring port residing between the upstream occlusion member 120 and the downstream occlusion member 122 to monitor the pressure in the aortic arch.

The root pressure lumen 118 extends through the catheter shaft 102 from the proximal end 104 to a root pressure port 128 near the distal end 106 of the catheter shaft 102 to monitor pressure in the aortic root. The guide wire and cardioplegia lumen 116 extends from the proximal end 104 of the catheter shaft 102 to a guide wire/cardioplegia port 136 at the distal end 106 of the catheter shaft 102, distal to the upstream occlusion member 120. Preferably, the distal end 106 of the catheter shaft 102 is smoothly tapered or rounded for easy introduction and to avoid trauma or injury to the aortic wall during insertion or withdrawal of the aortic catheter 100.

Preferably, the aortic catheter 100 includes one or more markers, which may include radiopaque markers and/or sonoreflective markers, to enhance imaging of the aortic catheter 100 using fluoroscopy or ultrasound, such as transesophageal echocardiography (TEE). In this illustrative embodiment, the aortic catheter 100 includes a distal radiopaque marker 138 positioned near the distal end 106 of the catheter shaft 102, an intermediate radiopaque marker 140 positioned near the proximal edge of the upstream occlusion member 120, and a proximal radiopaque marker 142 positioned near the distal edge of the downstream anchoring member 122. Each of the radiopaque markers 138, 140, 142 may be made of a ring of dense radiopaque metal, such as gold, platinum, tantalum, tungsten or alloys thereof, or a ring of a polymer or adhesive material heavily loaded with a radiopaque filler material.

The proximal end 104 of the catheter shaft 102 is connected to a manifold 150 with fittings for each of the catheter lumens. The corporeal perfusion lumen 108 is connected to a Y-fitting 162 that has a barb connector 152 for connection to a perfusion pump or the like and a luer connector 154, which may be used for monitoring perfusion pressure, for withdrawing fluid samples or for injecting medications or other fluids. Likewise, the arch perfusion lumen 110 is connected to a Y-fitting 164 that has a barb connector 156 for connection to a perfusion pump and a luer connector 158. The balloon inflation lumens 112 and 114 are connected to luer connectors 160 and 166 respectively or other fittings suitable for connection to a syringe or balloon inflation device. The guide wire and cardioplegia lumen 116 is connected to a three-way Y-fitting 170 that has a barb connector 172 for connection to a cardioplegia infusion pump, a luer connector 174 and a guide wire port 176 with a Touhy-Borst adapter or other hemostasis valve. The root pressure lumen 118 is connected to a luer connector 168 or other fitting suitable for connection to a pressure monitor.

FIG. 3 illustrates a side view of a superior vena cava cannula 399 according to the present invention with a tubular shaft 398 configured for introduction into a patient's venous system through the jugular vein or other peripheral artery. FIG. 4 is a magnified lateral cross sectional of the superior vena cava cannula 399 of FIG. 3 taken along line 4—4 in FIG. 3.

Referring now to FIGS. 3 and 4 collectively, the superior vena cava cannula 399 has a tubular shaft 398 that includes a venous drainage lumen 397 and a balloon inflation lumen 396. The tubular shaft 398 preferably has a length of approximately 15 cm to 60 cm and a diameter of approximately 10 to 32 French (3.3 mm to 10.7 mm diameter). An occlusion balloon 395 or other expandable occlusion member is mounted on the tubular shaft 398 near the distal end of the cannula 399. The occlusion balloon 395 or other expandable occlusion member preferably has an expanded diameter of approximately 5 mm to 40 mm. The venous drainage lumen 397 extends through the tubular shaft 398 from a venous drainage fitting 394 to one or more venous drainage ports 393 on the tubular shaft 398 proximal to the occlusion balloon 395. The venous drainage fitting has a luer connector 373 which may be used for monitoring pressure, temperature, chemical compositions and for withdrawing fluid samples or for injecting medications or other fluids, a barb connector 372 or other suitable fitting for being connected to a CPB machine and a guide wire entry connector 392 in the form of a Thouy-Borst fitting or other suitable hemostasis valve for creating a fluid tight seal when using a guide wire. When a guide wire is used the venous drainage lumen 397 serves as an additional guide wire lumen capable of receiving a guide wire 301 which is guided to a guide wire port 374 on the end of the tubular shaft 398 distal to the occlusion balloon 395. Alternatively, a separate lumen may be provided leading to a port distal to the occlusion balloon 395 wherein a separate monitoring device may be slidably or integrally disposed to give monitoring information inside or outside the cannula 399, and inside the superior vena cava. The balloon inflation lumen 396 extends through the tubular shaft 398 from a balloon inflation fitting 391 on the proximal end of the cannula 399 to one or more balloon inflation ports 390 within the occlusion member 395.

FIG. 5 illustrates a side view of an inferior vena cava cannula 589 according to the present invention with a tubular shaft 588 configured for introduction into a patient's venous system through the femoral or other peripheral artery. FIG. 6 is a magnified lateral cross sectional of the inferior vena cava cannula 589 of FIG. 5 taken along line 6—6 in FIG. 5.

Referring collectively to FIGS. 5 and 6, the inferior vena cava cannula 589 is configured for introduction into the patient's inferior vena cava via the femoral vein or other suitable venous access point in the lower extremities. The inferior vena cava cannula 589 has a tubular shaft 588 that includes a venous drainage lumen 587 and a balloon inflation lumen 586. The tubular shaft 588 preferably has a length of approximately 15 cm to 90 cm and a diameter of approximately 10 to 32 French (3.3 mm to 10.7 mm diameter). An occlusion balloon 585 or other expandable occlusion member is mounted on the tubular shaft 588 near the distal end of the cannula 589. The occlusion balloon 585 or other expandable occlusion member preferably has an expanded diameter of approximately 5 mm to 40 mm. The venous drainage lumen 587 extends through the tubular shaft 588 from a venous drainage fitting 584 on the proximal end of the cannula shaft 588 to one or more venous drainage ports 583 on the tubular shaft 588 proximal to the occlusion balloon 585. The venous drainage fitting 584 has a luer connector 563 which may be used for monitoring pressure, temperature, chemical compositions and for withdrawing fluid samples or for injecting medications or other fluids, a barb connector 562 or other suitable fitting for being connected to a CPB machine and a guide wire entry connector 582 in the form of a Thouy-Borst fitting or other suitable hemostasis valve for creating a fluid tight seal when using a guide wire. When a guide wire is used the venous drainage lumen 587 serves as an additional guide wire lumen configured for receiving a guide wire 501 which is guided to a guide wire port 564 on the end of the tubular shaft 588 distal to the occlusion balloon 585. Alternatively, a separate lumen may be provided leading to a port distal to the occlusion balloon 585 wherein a separate monitoring device integral or nonintegral is slideably disposed to give monitoring information inside or outside the cannula 589, and inside the inferior vena cava. The balloon inflation lumen 586 extends through the tubular shaft 588 from a balloon inflation fitting 581 on the proximal end of the cannula 589 to one or more balloon inflation ports 580 within the occlusion balloon 585.

Figure 8:
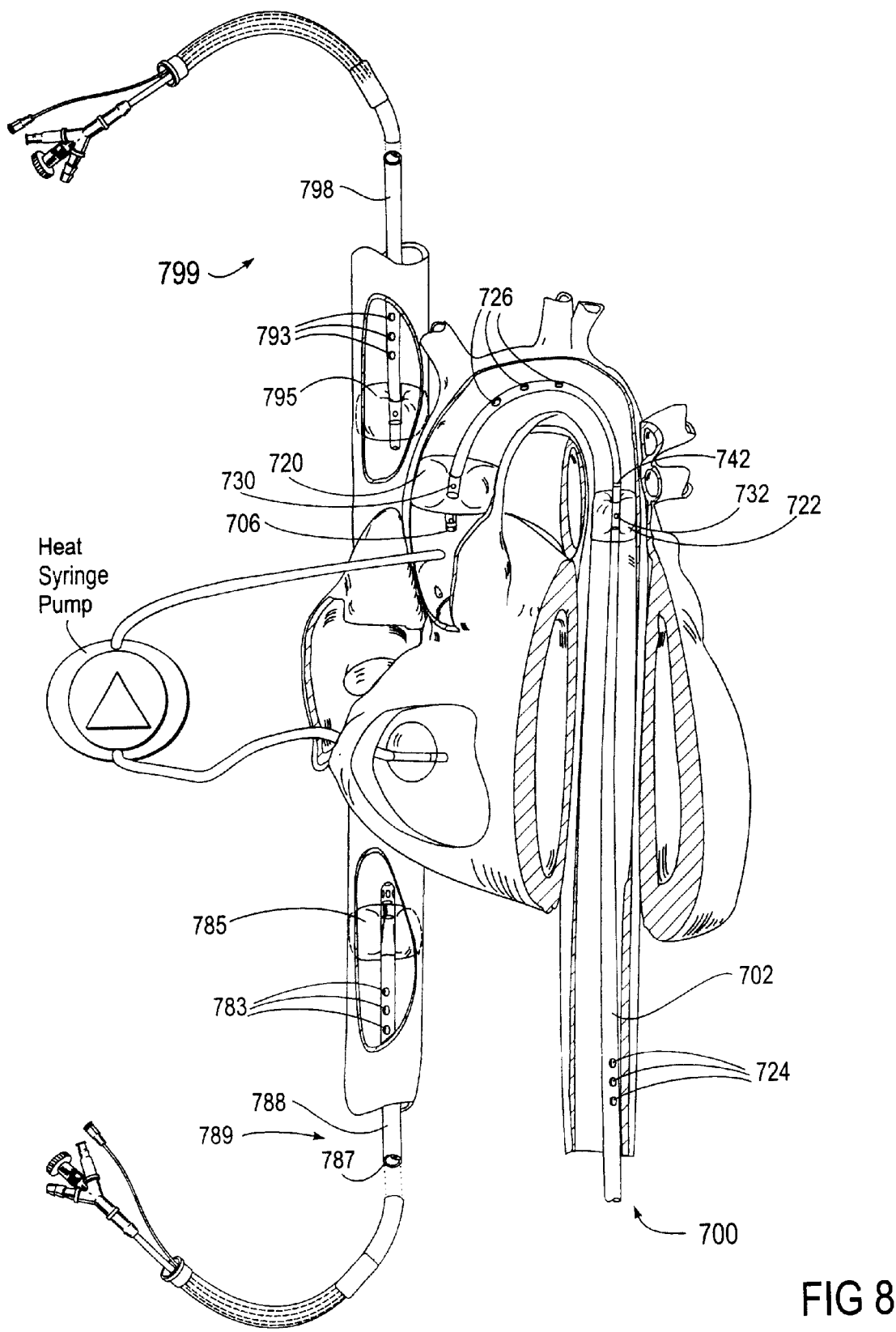
FIG. 8 is a cutaway close-up view of the cannula placement as shown in FIG. 7 with a portion of the patient's heart cut away to better show the descending aorta.

FIG. 7 is a schematic illustration depicting a first embodiment of the present invention configured for selective, isolated, dual-loop perfusion of a patient's circulatory system. The circulatory support system has a cerebral loop for perfusion of the patient's cerebral circulation and upper extremities and a separate corporeal loop for perfusion of the patient's viscera and lower extremities. Optionally, the patient's coronary circulation may be included in the cerebral loop or the corporeal loop or a third, isolated coronary loop may be created. In this embodiment of the circulatory support system, arterial cannulation is provided by a dualballoon, selective arterial perfusion cannula 700, and venous cannulation is provided by a superior vena cava cannula 799 and a separate inferior vena cava cannula 788. FIG. 8 is a cutaway close-up view of the cannula placement as shown in FIG. 7 with,a portion of the patient's heart cut away to better show the descending aorta.

Referring now to FIGS. 7 and 8, the cerebral closed loop circulation is created by having venous drainage port 793 proximal to the occlusion balloon 795 in fluid communication with the venous drainage lumen 797. Connected to the. venous drainage lumen 797 of the superior vena cava cannula 799 is a venous drainage fitting 794 which is connected to inflow tubing 777 in fluid communication with inflow port 751 of a first blood circulation pump 750. After the. blood is conditioned it is pumped through outflow port 753 which is coupled to outflow tubing 754 in fluid communication with barb connector 756 which is coupled to the arch perfusion lumen 710 of the arterial cannula 700. The first blood circulation pump 750 may be a peristaltic roller pump, a centrifugal blood pump or other suitable blood circulation pump. For illustrative purposes a membrane oxygenator system is provided for the cerebral circulation and a bubble oxygenator is provided for the corporeal circulation. It is understood by those skilled in the art that either oxygenator may be employed. In addition, a system may use two bubble oxygenators, two membrane oxygenators or a membrane oxygenator and a bubble oxygenator or any combination thereof. This illustrative embodiment and all others contained herein may be configured with any combination as so stated.

The cerebral loop of the circulatory support system includes a venous drainage cannula 799, which drains to a venous blood reservoir 701, the blood is pumped to a heat exchanger 702 and membrane oxygenator 703 in series with the first blood circulation pump. Optionally, vacuum assist (not shown) may be used to enhance venous drainage through the superior vena cava cannula 799. Venous blood from the head and upper extremities enters the patient's superior vena cava and is drained out through the venous drainage lumen 797 of the superior vena cava cannula 799. The blood is oxygenated, cooled and recirculated by the first blood circulation pump 757 to the head and upper extremities through the arch perfusion lumen 710 and out the arch perfusion ports 726 within the arterial cannula 700.

The corporeal loop of the circulatory support system includes a venous drainage cannula 789, which drains into a combined heat exchange bubble oxygenator to an arterial reservoir where it is pumped to arterial cannula 700. The venous drainage lumen 787 is fluid communication with drainage port 783 proximal to the occlusion balloon 785 in fluid communication with the venous drainage lumen 787. Alternatively there can be a venous drainage port 730 distal as well as proximal to the occlusion balloon 785. Connected to the venous drainage lumen 787 of the inferior vena cava cannula 789 has a venous drainage fitting 784 connected to corporeal inflow tubing 749 in fluid communication with inflow port 748 of the second blood circulation pump 747. After the blood is conditioned it is pumped through outflow port 746 which is coupled to outflow tubing 745 in fluid communication with barb connector 752 which is coupled to the corporeal perfusion lumen 708 of the arterial cannula 700. The second blood circulation pump 747 may be a peristaltic roller pump, a centrifugal blood pump or other suitable blood circulation pump. The corporeal loop of the circulatory support system includes a venous blood reservoir 706, a blood oxygenator 705 and heat exchanger 704 in series with the second blood circulation pump. Optionally, vacuum assist (not shown) may be used to enhance venous drainage through the inferior vena cava cannula 789. Venous blood from the viscera and lower extremities enters the patient's inferior vena cava and is drained out through the venous drainage lumen 787 of the inferior vena cava cannula 789. The blood is oxygenated, cooled and recirculated by the second blood circulation pump 747 to the viscera and lower extremities through the corporeal perfusion lumen 708 and out the corporeal perfusion ports 724 of the arterial cannula 700.

Optionally, either the superior vena cava cannula 799 or the inferior vena cava cannula 789 may be made without the occlusion balloon or with additional drainage ports distal to the balloon so that the cannula drains the patient's right atrium and the coronary sinus as part of the cerebral loop or the corporeal loop, respectively. Alternatively, either the superior vena cava cannula 799 or the inferior vena cava cannula 789 can be made with a separate, second drainage lumen connected to drainage ports positioned distal to the balloon for draining the patient's right atrium and the coronary sinus. A separate coronary perfusion loop can be created by connecting the second drainage lumen to the inflow of a third blood circulation pump and connecting the outflow of the pump to the cardioplegia lumen of the arterial cannula 700. The third blood circulation pump may be a peristaltic roller pump, a centrifugal blood pump or other suitable blood circulation pump. Preferably, the coronary loop also includes a venous blood reservoir, a blood oxygenator and heat exchanger in series with the third blood circulation pump.

As another alternative, the coronary circulation can be isolated by using a coronary sinus catheter for retrograde administration of cardioplegia into the patient's coronary arteries. This would eliminate the need for the occlusion balloon on either the superior vena cava cannula 799 or the inferior vena cava cannula 789 and the patient's right atrium could be drained as part of the cerebral loop or the corporeal loop. For example, a superior vena cava cannula 799 without an occlusion balloon (not shown) or with the balloon deflated (not shown) could be inserted into the superior vena cava and the right atrium via the jugular vein. An inferior vena cava cannula 789 would be inserted into the inferior vena cava via the femoral vein and the occlusion balloon 785 inflated to isolate the corporeal loop. A coronary sinus catheter can be inserted collaterally with the superior vena cava cannula 799 via the jugular vein to isolate the coronary circulation on the venous side and for antegrade or retrograde flow of blood, cardioplegia or other fluids. Suitable coronary sinus catheter for retrograde administration of cardioplegia can be found in U.S. Pat Nos. 5,738,652; 5,722,963; 5,720,726; 5,662,607; 5,653,690; 5,643,231; 5,620,418; 5,617,854; 5,597,377; 5,558,644; 5,549,581; 5,533,957; 5,505,698; 5,488,960; 5,487,730; 5,466,216; 5,423,772; 5,423,745; 5,401,244; 5,395,331; 5,385,548; 5,385,540; 5,324,260; 5,197,952; 5,024,668; 5,021,045; 4,943,277; 4,927,412; 4,753,637; 4,648,384; 4,459,977, which are hereby incorporated by reference in their entirety.

To complete the closed loop circulation system an arterial perfusion cannula 700 is provided. The dual-balloon, selective arterial perfusion cannula 700 is configured for retrograde introduction into the patient's aorta via a peripheral arterial access point, such as the femoral artery. The dual-balloon, selective arterial perfusion cannula 700 has a tubular shaft 702 that includes a corporeal perfusion lumen 708, an arch perfusion lumen 710, a guide wire cardioplegia lumen 716, two balloon inflation lumens 712 and 714 and, a root pressure lumen 718. An upstream occlusion balloon 720 or other expandable occlusion member is mounted on the tubular shaft 702 so that it is positioned in the ascending aorta between the coronary arteries and the right brachiocephalic artery. A downstream occlusion balloon 722 or other expandable occlusion member is mounted on the tubular shaft 702 so that it is positioned in the descending aorta downstream of the left subclavian artery. The corporeal perfusion lumen 708 extends through the tubular shaft 702 from a corporeal barb connector 752 to one or more corporeal perfusion ports 724 on the tubular shaft 702 proximal to the downstream occlusion balloon 722. The arch perfusion lumen 710 extends through thetubular shaft 702 from an arch barb connector 756 to one or more arch perfusion ports 726 on the tubular shaft 702 between the upstream occlusion balloon 720 and the downstream occlusion balloon 722. The guide wire cardioplegia lumen 716 extends through the tubular shaft 702 from a barb connector 772 to one or more cardioplegia ports 736 on the tubular shaft distal to the upstream occlusion balloon 720. The root pressure lumen 718 extends through the tubular shaft 702 from a pressure fitting 768 to a root pressure port 728 on the tubular shaft 702 distal to the upstream occlusion balloon 720. A first balloon inflation lumen 712 extends through the tubular shaft 702 a balloon inflation fitting 760 a balloon inflation port 732 within the downstream occlusion balloon 722. A second balloon inflation lumen 714 extends through the tubular shaft 702 to a balloon inflation fitting 766 to a balloon inflation port 730 within the upstream occlusion balloon 720. FIGS. 9 through 15 illustrate a second embodiment of the circulatory support system of the present invention, which is also configured for selective, isolated, dual-loop perfusion of a patient's circulatory system. The circulatory support system has a cerebral loop for perfusion of the patient's cerebral circulation and upper extremities and a separate corporeal loop for perfusion of the patient's viscera and lower extremities. As in the previously described embodiment, the patient's coronary circulation may optionally be included in the cerebral loop or the corporeal loop or a third, isolated coronary loop may be created. In this embodiment of the circulatory support system, arterial canrulation is provided by a dual-balloon, selective arterial perfusion cannula 900 similar to the one previously described in connection with FIG. 1 and venous cannulation is provided by a dual-lumen venous drainage cannula 1199.

FIG. 9 illustrates a side view of the aortic catheter 900 according,to the present invention with a catheter shaft 902 configured for retrograde deployment via femoral artery access. In order to facilitate placement of the aortic catheter 900 and to improve the stability of the catheter 900 in the proper position in the patient's aorta, a distal region 944 of the catheter shaft 902 may be preshaped with a curve to match the internal curvature of the patient's aortic arch. The curved distal region 944 represents a J-shaped curve of approximately 180 degrees of arc with a radius of curvature of approximately 2 to 4 cm to match the typical curvature of the aortic arch in an adult human patient. In addition, the distal end 906 of the catheter may be skewed slightly up out of the plane of the curve to accommodate the forward angulation of the patient's ascending aorta. Additionally, the catheter shaft 902 may be reinforced, particularly in the curved distal region 944, for example with braided or coiled wire, to further improve the stability of the catheter 900 in the proper position in the patient's aorta.

Illustrated in FIG. 10, is a magnified lateral cross section of the aortic catheter 900 of FIG. 9 taken along line 10—10 showing the multi-lumen arrangement of the catheter shaft 902. The catheter shaft 902 has six lumens: a corporeal perfusion lumen 908, an arch perfusion lumen 910, a common balloon inflation lumen 912, an arch monitoring lumen 914, a guide wire and cardioplegia lumen 916 and a root pressure lumen 918.

Referring to FIG. 9 the elongated catheter shaft 902 is preferably formed of a flexible thermoplastic material, a thermoplastic elastomer or a thermoset elastomer. The catheter shaft 902 may be fabricated separately by known extrusion methods and joined together end-to-end, for example by heat welding or by adhesive bonding. Alternatively, the catheter shaft 902 may be fabricated by dipping or by composite construction techniques and joined together or the entire catheter shaft 902 may be fabricated integrally. Suitable materials for the elongated catheter shaft 902 include, but are not limited to, polyvinylchloride, polyurethane, polyethylene, polypropylene, polyamides (nylons), polyesters, silicone, latex, and alloys or copolymers thereof, as well as braided, coiled or counterwound wire or filament reinforced composites.

An upstream occlusion member 920 is mounted on the catheter shaft 902 near the distal end 906 of the catheter 900. The upstream occlusion member 920 in this embodiment is in the form of an expandable, inflatable balloon bonded to the catheter shaft 902 by heat welding or with an adhesive. Suitable materials for the upstream occlusion member 920 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the outer surface of the upstream occlusion member 920 may include a friction increasing coating or texture to increase friction with the aortic wall when deployed. The upstream occlusion member 920 has a deflated state, in which the diameter of the occlusion member 920 is preferably not much larger than the diameter of the catheter shaft 902, and an inflated state, in which the occlusion member 920 expands to a diameter sufficient to occlude blood flow in the ascending aorta of the patient. For use in adult human patients, the inflatable balloon upstream occlusion member 920 preferably has an inflated outer diameter of approximately 1.5 cm to 5.0 cm. Preferably, the inflatable occlusion member 920 has an inflated length that is not significantly longer than its inflated diameter, or, more preferably, is shorter than its inflated diameter. This shortened inflated profile allows the upstream occlusion member 920 to be easily placed within the ascending aorta between the coronary arteries and the brachiocephalic artery without any danger of inadvertently occluding either.

A downstream occlusion member 922 is mounted on the catheter shaft 902 at a position proximal to and spaced apart from the upstream occlusion member 920. The distance between the upstream occlusion member 920 and the downstream occlusion member 922 is preferably between 3 and 20 cm, more preferably between 8 and 15 cm, and is chosen so that when the aortic catheter 900 is deployed and the upstream occlusion member 920 is positioned within the ascending aorta between the coronary arteries and the brachiocephalic artery, the downstream anchoring member 922 will be positioned in the descending aorta downstream of the left subclavian artery. The downstream occlusion member 922 in this embodiment is in the form of an expandable, inflatable balloon bonded to the catheter shaft 902 by heat welding or with an adhesive. The downstream occlusion member 922 is may be larger, that is to say, more elongated, than the upstream occlusion member 920 of the same size or smaller. Suitable materials for the inflatable balloon downstream anchoring member 922 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the outer surface of the downstream anchoring member 922 may include a friction increasing coating or texture to increase friction with the aortic wall when deployed.

The inflatable downstream occlusion member 922 has a deflated state, in which the diameter of the occlusion member 922 is preferably not much larger than the diameter of the catheter shaft 902, and an inflated state, in which the occlusion member 922 expands to a diameter sufficient to substantially prohibit blood flow in the descending aorta of the patient. For use in adult human patients, the downstream occlusion member 922 preferably has an inflated outer diameter of approximately 1.0 cm to 5.0 cm and a length of approximately 1.0 cm to 7.5 cm. The more elongated the occlusion member 922 the greater the anchoring friction against the wall of the descending aorta when the downstream occlusion member 922 is inflated in order to prevent migration of the aortic catheter 900 due to pressure gradients within the aorta during perfusion.

The corporeal perfusion lumen 908 extends through the catheter shaft 902 from the proximal end 904 to one or more corporeal perfusion ports 924 on the exterior of the catheter shaft 902 proximal of the downstream occlusion member 922. Alternatively, to simplify catheter design and to reduce overall catheter diameter a separate contralateral, or co-lateral peripheral access arterial cannula may be used to access either the same femoral artery or the other femoral artery. The arch perfusion lumen 910 extends through the catheter shaft 902 from the proximal end 904 to one or more arch perfusion ports 926 on the exterior of the catheter shaft 902 between the upstream occlusion member 920 and the downstream occlusion member 922. A common balloon inflation lumen 912 extends through the catheter shaft 902 from the proximal end 904 to balloon inflation ports 932 and 930 which reside in the interior of downstream occlusion balloon 922 and the upstream occlusion balloon 920 respectively. Alternatively, separate inflation lumens can be implemented to separately inflate the downstream occlusion member 922 and the upstream occlusion member 920.

The arch monitoring lumen 914 extends through the catheter shaft 902 from the proximal end 904 to an arch monitoring port 934 proximal to the upstream occlusion member 920 to monitor pressure in the aortic root. The root pressure lumen 918 extends through the catheter shaft 902 from the proximal end 904 to a root pressure port 928 near the distal end 906 of the catheter shaft 902 to monitor pressure in the aortic root. The guide wire and cardioplegia lumen 916 extends from the proximal end 904 of the catheter shalt 902 to a guide wire/cardioplegia port 936 at the distal end 906 of the catheter shaft 902, distal to the upstream occlusion member 920. Preferably, the distal end 906 of the catheter shaft 902 is smoothly tapered or rounded for easy introduction and to avoid trauma or injury to the aortic wall during insertion or withdrawal of the aortic catheter 900.

Preferably, the aortic catheter 900 includes one or more markers, which may include radiopaque markers and/or sonoreflective markers, to enhance imaging of the aortic catheter 900 using fluoroscopy or ultrasound, such as transesophageal echocardiography (TEE). In this illustrative embodiment, the aortic catheter 900 includes a distal radiopaque marker 938 positioned near the distal end 906 of the catheter shaft 902, an intermediate radiopaque marker 940 positioned near the proximal edge of the upstream occlusion member 920, and a proximal radiopaque marker 942 positioned near the distal edge of the downstream anchoring member 922. Each of the radiopaque markers 938, 940, 942 may be made of a ring of dense radiopaque metal, such as gold, platinum, tantalum, tungsten or alloys thereof, or a ring of a polymer or adhesive material heavily loaded with a radiopaque filler material.

The proximal end 904 of the catheter shaft 902 is connected to a manifold 950 with fittings for each of the catheter lumens. The corporeal perfusion lumen 908 is connected to a Y-fitting 962 that has a barb connector 952 for connection to a perfusion pump or the like and a luer connector 954, which may be used for monitoring perfusion pressure, temperature, chemical compositions and for withdrawing fluid samples or for injecting. medications or other fluids. Likewise, the arch perfusion lumen 910 is connected to a Y-fitting 964 that has a barb connector 956 for connection to a perfusion pump and a luer connector 958 which may be used for monitoring arch perfusion pressure, temperature, chemical compositions and for withdrawing fluid samples or for injecting medications or other fluids. The common balloon inflation lumen 912 is connected to a stopcock or luer connector 960 or other fitting suitable for connection to a syringe or balloon inflation device. In addition the inflation lumen 912 may be attached to a pressure monitoring device to give visible and or tactile feedback concerning the balloon inflation pressure. The guide wire and cardioplegia lumen 916 is connected to a three-way Y-fitting 970 that has a barb connector 972 for connection to a cardioplegia infusion pump, a luer connector 974 capable of monitoring root perfusion pressure, temperature and chemical compositions and a guide wire port 976 with a Touhy-Borst adapter or other hemostasis valve. The root pressure lumen 918 is connected to a luer connector 968 or other suitable fitting capable of monitoring arch perfusion pressure, temperature and chemical compositions or for withdrawing fluid samples. The arch monitoring lumen 914 is connected to a luer connector 966 or other suitable fitting capable of monitoring arch perfusion pressure, temperature, and chemical compositions or for withdrawing fluid samples. Alternatively, sensors may be placed on the catheter shaft or inside the catheter shaft to measure chemical compositions in the aortic arch.

FIG. 11 illustrates a side view of a dual lumen venous drainage cannula 1199 of the present invention configured for introduction through the patient's inferior vena cava via the femoral vein or other suitable venous access point in the lower extremities. Alternatively, the dual lumen venous drainage cannula 1199 may be configured for introduction though the patient's superior vena cava via the jugular vein or other suitable venous access point in the neck or upper extremities. The elongated tubular shaft 1198 may be fabricated separately by known extrusion methods and joined together end-to-end, for example by heat welding or by adhesive bonding. Alternatively, the elongated tubular shaft 1198 may be fabricated by dipping or by composite construction techniques and joined together or the entire tubular shaft 1198 may be fabricated integrally. Suitable materials for the elongated tubular shaft 1198 include, but are not limited to, polyvinylchloride, polyurethane, polyethylene, polypropylene, polyamides (nylons), polyesters, silicone, latex, and alloys or copolymers thereof, as well as braided, coiled or counterwound wire or filament reinforced composites.

FIG. 12 is a magnified lateral cross section of the venous drainage cannula 1199 taken along line 12—12 of FIG. 11. FIG. 13 is a magnified lateral cross section of the venous drainage cannula 1199 taken along line 13—13 of FIG. 11. Collectively FIGS. 11 through 13 illustrate the multi-lumen arrangement of the dual-lumen venous drainage cannula 1199 having an elongated tubular shaft 1198 which includes a first venous drainage,lumen 1188; a second venous drainage lumen 1189; a first balloon inflation lumen 1191,. and a second balloon inflation lumen 1194. Alternatively, the dual-lumen venous drainage cannula 1199 may have a common balloon inflation lumen capable of simultaneously inflating both occlusion balloons. The tubular shaft 1198 preferably has a length of approximately 15 cm to 90 cm and a diameter of approximately 10 to 32 French (3.3 mm to 10.7 mm diameter).

The dual-lumen venous drainage cannula 1199 includes a first occlusion balloon 1197 or other expandable occlusion member mounted on the tubular shaft 1198, which is positioned within the patient's superior vena cava when in,the operative position, and a second occlusion balloon 1196 or other expandable occlusion member, mounted on the tubular shaft 1198, which is positioned within the patient's inferior vena cava when in the operative position. Suitable materials for the first occlusion member 1197 and the second occlusion member 1196 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof The occlusion balloons 1196 and 1197 preferably have an expanded diameter of approximately 5 mm to 40 mm. When the dual-lumen venous drainage cannula 1199 is configured for femoral artery introduction, the first occlusion balloon 1197 is mounted near the distal end 1195 of the tubular shaft 1198 and the second occlusion balloon 1196 is mounted somewhat proximal to the first balloon 1197, as shown. Alternatiyely, for jugular vein introduction, these positions are reversed.

A first balloon inflation lumen 1191 is connected to a stopcock 1190 that extends through the tubular shaft 1198 to a balloon inflation port 1192 within the first occlusion balloon 1197. The second balloon inflation lumen 1194, is connected to a stopcock 1193, that extends through the tubular shaft 1198 to a balloon inflation port 1123 within the second occlusion balloon 1196. Alternatively, a common balloon inflation lumen may be implemented and a superior vena cava monitoring lumen may be implemented to monitor pressure, temperature and chemical composition in the superior vena cava.

The first venous drainage lumen 1188 extends from a venous drainage fitting 1187 through the tubular shaft 1198, to one or more superior vena cava drainage ports 1195 on the tubular shaft 1198 distal to the first occlusion balloon 1197. In addition, venous drainage ports 1182 which are distal to the second occlusion balloon 1196 are also in fluid communication with the first venous drainage lumen 1188. Alternatively, the venous drainage ports 1182 may be in fluid communication with the second venous drainage lumen 1189. The second venous drainage lumen 1189 extends from a venous drainage fitting 1181 through the tubular shaft 1198, to one or more inferior vena cava drainage ports 1173 on the tubular shaft 1198 proximal to the second occlusion balloon 1196. Preferably, the distal portion of the tubular shaft 1198 is smoothly tapered or rounded for easy introduction and to avoid trauma or injury to the vena cava during insertion or withdrawal of the venous cannula 1199.

Preferably, the venous cannula includes one or more markers, which may include radiopaque markers and/or sonoreflective markers, to enhance imaging of the venous cannula 1199 using fluoroscopy or ultrasound, such as transesophageal echocardiography (TEE). In this illustrative embodiment, the venous drainage cannula 1199 includes a distal radiopaque marker 1178 positioned near the distal end 1195 of the tubular shaft 1198, an intermediate radiopaque marker 1177 positioned near the drainage ports 1182, and a proximal radiopaque marker 1176 positioned near the distal edge of the second occlusion member 1196. Each of the radiopaque markers 1178, 1177, 1176 may be made of a ring of dense radiopaque metal, such as gold, platinum, tantalum, tungsten or alloys thereof, or a ring of a polymer or adhesive material heavily loaded with a radiopaque filler material.

The proximal end 1183 of the venous drainage cannula 1199 is connected to a manifold 1125 with fittings for each of the catheter lumens. The first venous drainage lumen 1188 is coupled to a three-way fitting 1187 that has a barb connector 1186 for connection to an external CPB machine, a luer connector 1185 capable of monitoring superior vena cava pressure, temperature and chemical compositions and a guide wire port 1184 with a Touhy-Borst adapter or other hemostasis valve on the proximal end of the cannula 1183. The second venous drainage lumen 1189 is coupled to a Y-fitting 1181 having a barb connector 1180, or other suitable fitting capable of being coupled to a CPB machine and a luer fitting 1179 capable of monitoring inferior vena cava pressure, temperature and chemical compositions. A first inflation lumen 1191 is coupled to a stopcock 1190, or other suitable fitting capable of being attached to an inflation mechanism and a second inflation lumen 1194 is coupled to a stopcock 1193, or other suitable fitting capable of being attached to an inflation mechanism. In addition, each inflation lumen may have an individual pressure-monitoring device proximal or distal to the stopcock to provide visible and tactile feedback concerning the balloon inflation pressures. Alternatively, a common inflation lumen may be implemented.

Figure 14:
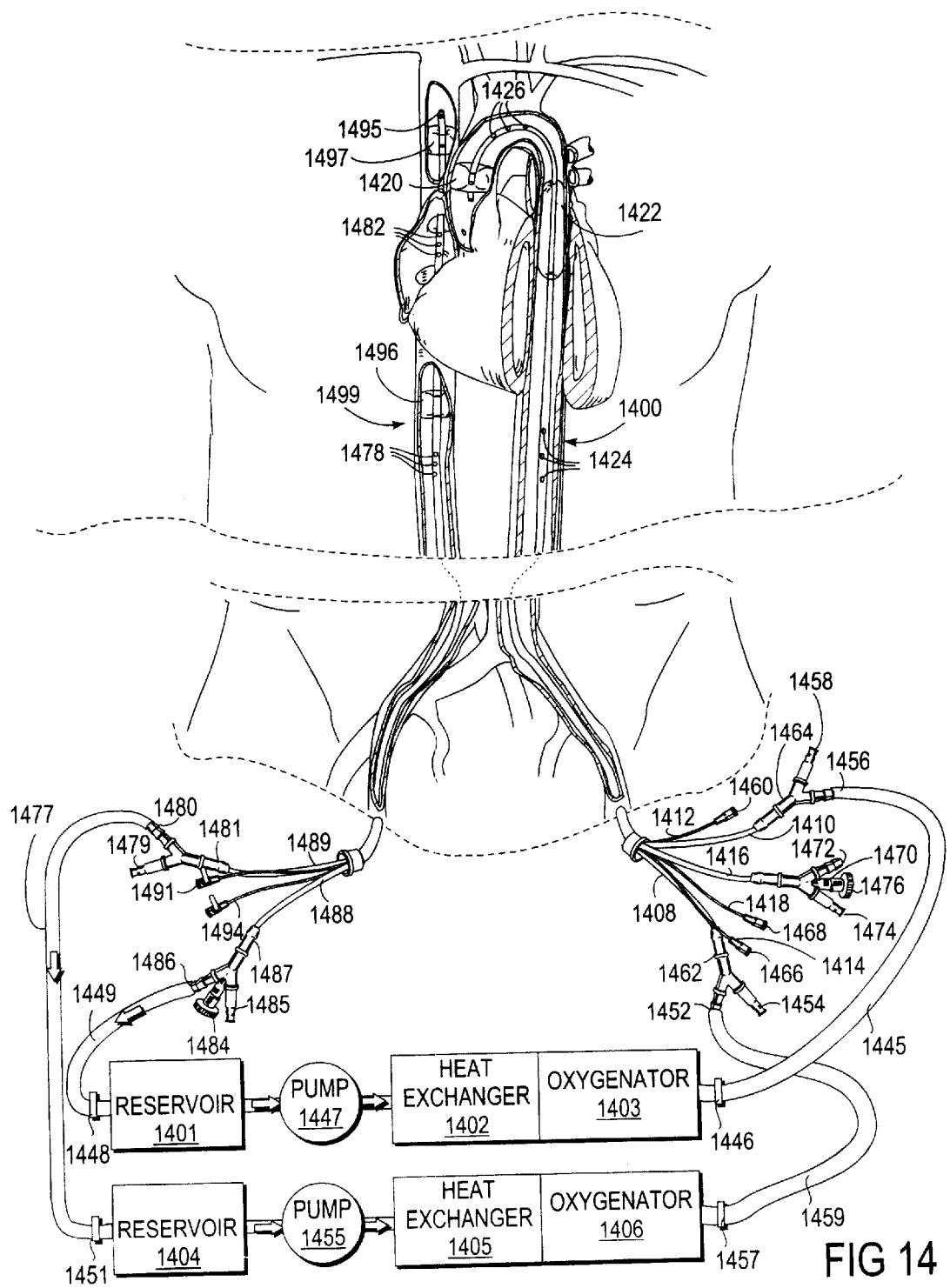
FIG. 14 is a schematic illustration depicting a second embodiment of the present invention configured for selective, isolated, dual-loop perfusion of a patient's circulatory system.
Figure 15:
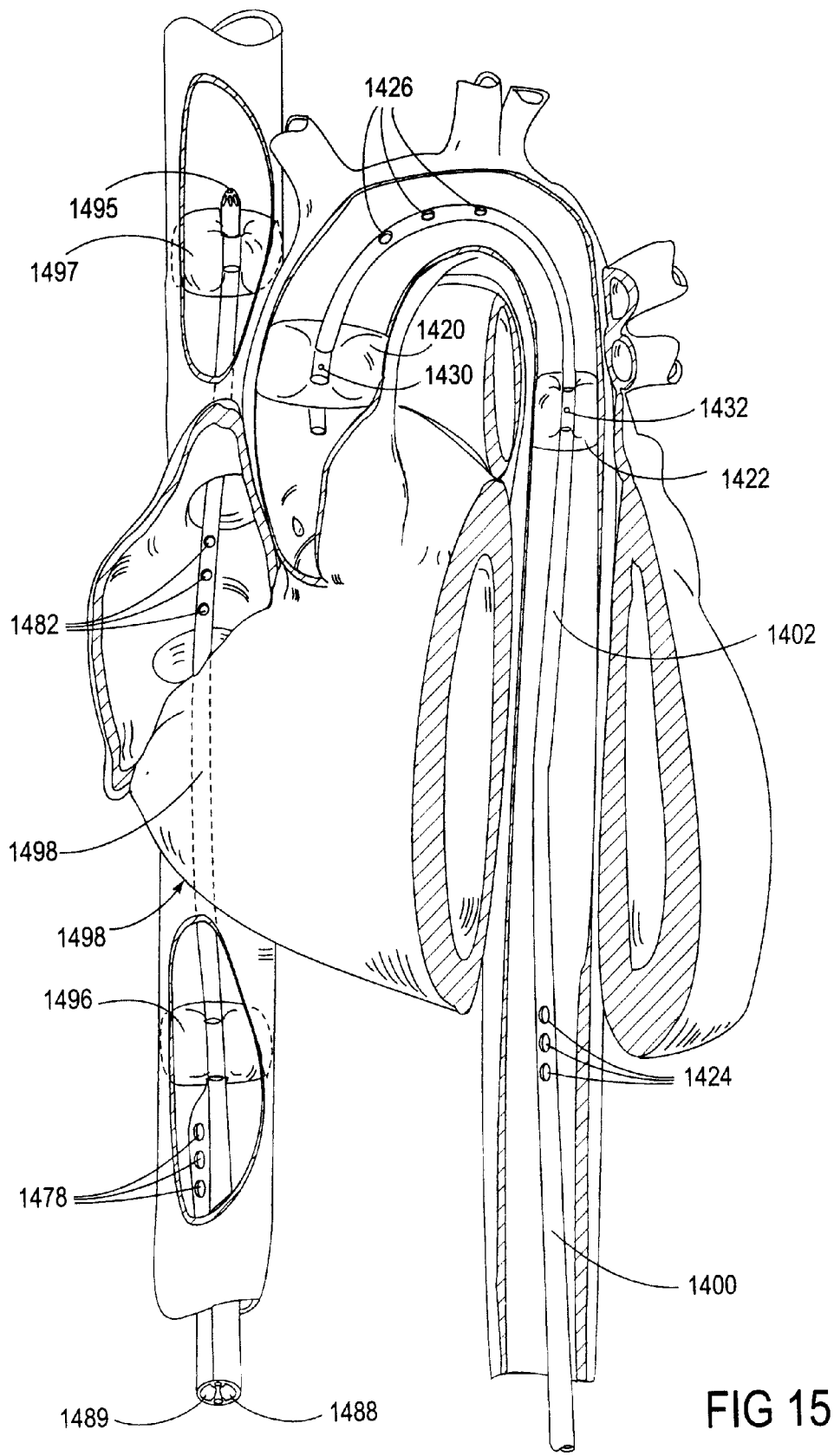
FIG. 15 is a cutaway close-up view of the cannula placement as shown in FIG. 14 with a portion of the patient's heart cut away to better show the descending aorta.

FIG. 14 illustrates the second embodiment of the closed loop circulatory system of the present invention. FIG. 15 is a cutaway close-up view of the cannula placement as shown in FIG. 14 with a portion of the patient's heart cut away to better show the descending aorta. The cerebral loop of the circulatory support system is created by having venous drainage ports 1495 and 1482 in fluid communication with the superior vena cava drainage lumen 1488. Coupled to the superior vena cava drainage lumen 1488 is a fitting 1487 having a barb connector 1486 coupled to tubing 1449 in fluid communication with an inflow port 1448 of a first blood circulation pump 1447. The blood is conditioned and pumped through the outflow port 1446 of the first blood circulation pump 1447 to the arch perfusion lumen 1410 of the arterial cannula 1400. The first blood circulation pump 1447 may be a peristaltic roller pump, a centrifugal blood pump or other suitable blood circulation pump. Preferably, the cerebral loop of the circulatory support system will also include a venous blood reservoir 1401, a blood oxygenator 1403 and heat exchanger 1402 in series with the first blood circulation pump 1447. Optionally, vacuum assist may be used to enhance venous drainage through the first venous drainage lumen 1488 of the dual-lumen venous drainage cannula 1499. Venous blood from the head and upper extremities enters the patient's superior vena cava and is drained out through the first venous drainage lumen 1488 of the dual-lumen venous drainage cannula 1499 as the first occlusion balloon 1497 prevents blood from traveling into the right atrium from the superior vena cava. The blood is oxygenated, cooled and recirculated by the first blood circulation pump 1447 to the head and upper extremities through the arch perfusion lumen 1410 of the arterial cannula 1400.

The corporeal loop of the circulatory support system is created by having a venous drainage port 1478 in fluid communication with inferior vena cava drainage lumen 1489. A second Coupled to the second venous drainage lumen 1489 is a fitting 1481 having a barb connector 1480 coupled to tubing 1477 in fluid communication with an inflow port 1451 of a second blood circulation pump 1455. After the blood is conditioned it is pumped through outflow port 1457 in fluid communication with tubing 1459 which is coupled to a barb connector 1452 in fluid communication the corporeal lumen 1408 of the aortic catheter 1400. The second blood circulation pump may be a peristaltic roller pump, a centrifugal blood pump or other suitable blood circulation pump. Preferably, the corporeal loop of the circulatory support system will also include a venous blood reservoir 1404, a blood oxygenator 1406 and heat exchangerl4o5 in series with the second blood circulation pump 1455. Optionally, vacuum assist may be used to enhance venous drainage through the second venous drainage lumen of the dual-lumen venous drainage cannula 1400. Venous blood from the viscera and lower extremities enters the patient's inferior vena cava and is drained out through the second venous drainage lumen 1489 of the dual-lumen venous drainage cannula 1499. The blood is oxygenated, cooled and recirculated by the second blood circulation pump 1455 to the viscera and lower extremities through the corporeal perfusion lumen 1408 of the arterial catheter 1400.

Optionally, the dual-lumen venous drainage cannula 1499 may be made without either the first occlusion balloon or the second occlusion balloon or one of the balloons may be partially deflated or completely deflated when operating in this mode since isolation of the patient's right atrium and the coronary sinus is unnecessary. Alternatively, the dual-lumen venous drainage cannula 1499 may be provided with a third venous drainage lumen within the tubular shaft connected to the drainage ports 1482 between the first and second balloons for draining the patient's right atrium and the coronary sinus. A separate coronary perfusion loop can be created by connecting the third venous drainage lumen to the inflow of a third blood circulation pump and connecting the outflow of the pump to the cardioplegia lumen of the arterial cannula 1400. The third blood circulation pump may be a peristaltic roller pump, a centrifugal blood pump or other suitable blood circulation pump. Preferably, the coronary loop also includes a venous blood reservoir, a blood oxygenator and heat exchanger in series with the third blood circulation pump.

As another alternative, the coronary circulation can be isolated by inserting a coronary sinus catheter via the jugular vein to isolate the coronary circulation on the venous side and for antegrade or retrograde flow of blood, cardioplegia or other fluids into the patient's coronary arteries. The first occlusion balloon 1495 could be eliminated from the dual-lumen venous drainage cannula 1499 or left uninflated so that the patient's right atrium will be drained as part of the cerebral loop.

FIGS. 16 through 23 collectively illustrate a third embodiment of the circulatory support system of the present invention, which is also configured for selective, isolated, dual-loop perfusion of a patient's circulatory system. The circulatory support system has a cerebral loop for perfusion of the patient's cerebral circulation and upper extremities and a separate corporeal loop for perfusion of the patient's viscera and lower extremities. As in the previously described embodiment, the patient's coronary circulation may optionally be included in the cerebral loop or the corporeal loop or a third, isolated coronary loop may be created through the use of a separate coronary sinus catheter or through a separate pump. In this third embodiment of the circulatory support system, arterial cannulation is provided by a coaxial dual-balloon, selective arterial perfusion cannula 1600 and venous cannulation is provided by a coaxial dual-lumen venous drainage cannula 1799.

FIG. 16 illustrates a side view of the aortic catheter 1600 according to the present invention with a coaxial catheter shaft 1602 configured for retrograde deployment via femoral artery access. Alternatively, a separate contralateral or colateral arterial cannula may be provided to provide perfusion to the corporeal body through separate cannulation of the a second peripheral artery. In order to facilitate placement of the aortic catheter 1600 and to improve the stability of the catheter 1600 in the proper position in the patient's aorta, a distal region 1644 of the catheter shaft 1602 may be pre-shaped with a curve to match the internal curvature of the patient's aortic arch. The curved distal region 1644 represents a J-shaped curve of approximately 180 degrees of arc with a radius of curvature of approximately 2 to 4 cm to match the typical curvature of the aortic arch in an adult human patient. In addition, the distal end 1606 of the catheter may be skewed slightly up out of the plane of the curve to accommodate the forward angulation of the patient's ascending aorta. Additionally, the catheter shaft 1602 may be reinforced, particularly in the curved distal region 1644, for example with braided or coiled wire, to further improve the stability of the catheter 900 in the proper position in the patient's aorta.

Illustrated in FIG. 17, is a magnified lateral cross section of the aortic catheter 1600 of FIG. 16 taken along line 17—17 showing the multi-lumen coaxial arrangement of the catheter shaft 1602. The catheter shaft 1602 has six lumens: a corporeal perfusion lumen 1608; an arch perfusion lumen 1610; a common balloon inflation lumen 1612; an arch monitoring lumen 1614; a guide wire and cardioplegia lumen 1616 and a root pressure lumen 1618.

FIG. 18 is a magnified lateral cross-section of the aortic catheter 1600 of FIG. 16 taken along line 18—18 showing the multi-lumen arrangement of the catheter shaft 1602. Shown in FIG. 18, five of the six lumens continue distally through the catheter shaft 1602: the arch perfusion lumen 1610; the common balloon inflation lumen 1612; the arch monitoring lumen 1614; the guide wire and cardioplegia lumen 1616 and the root pressure lumen 1618. The corporeal perfusion lumen terminates at a position distal to the corporeal perfusion ports 1624.

Referring to FIGS. 16 through 18 the elongated catheter is comprised of an inner tubular shaft and an outer tubular shaft configured in a coaxial relationship such that an annular space is created therebetween. The annular space between the tubular shafts 1603 and 1606 defines the corporeal lumen 1608. The tubular shafts 1603 and 1606 are preferably formed of a flexible thermoplastic material, a thermoplastic elastomer or a thermoset elastomer. The coaxial catheter shaft 1602 may be fabricated separately by known extrusion methods and joined together end-to-end, for example by heat welding or by adhesive bonding. Alternatively, the coaxial catheter shaft 1602 may be fabricated by dipping or by composite construction techniques and joined together or the entire catheter shaft 1602 may be fabricated integrally. Suitable materials for the elongated catheter shaft 1602 include, but are not limited to, polyvinylchloride, polyurethane, polyethylene, polypropylene, polyamides (nylons), polyesters, silicone, latex, and alloys or copolymers thereof, as well as braided, coiled or counterwound wire or filament reinforced composites.

An upstream occlusion member 1620 is mounted on the inner tubular shaft 1603 near the distal end 1606 of the catheter 1600. The upstream occlusion member 1620 in this embodiment is in the form of an expandable, inflatable balloon bonded to the catheter shaft 1602 by heat welding or with an adhesive. Suitable materials for the upstream occlusion member 1620 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof In addition, the outer surface of the upstream occlusion member 1620 may include a friction increasing coating or texture to increase friction with the aortic wall when deployed. The upstream occlusion member 1620 has a deflated state, in which the diameter of the occlusion member 1620 is preferably not much larger than the diameter of the catheter shaft 1602, and an inflated state, in which the occlusion member 1620 expands to a diameter sufficient to occlude blood flow in the ascending aorta of the patient. For use in adult human patients, the inflatable balloon upstream occlusion member 1620 preferably has an inflated outer diameter of approximately 1.5 cm to 5.0 cm. Preferably, the inflatable occlusion member 1620 has an inflated length that is not significantly longer than its inflated diameter, or, more preferably, is shorter than its inflated diameter. This shortened inflated profile allows the upstream occlusion member 1620 to be easily placed within the ascending aorta between the coronary arteries and the brachiocephalic artery without any danger of inadvertently occluding either.

A downstream occlusion member 1622 is mounted on the catheter shaft 1602 at a position proximal to and spaced apart from the upstream occlusion member 1620. The distance between the upstream occlusion member 1620 and the downstream occlusion member 1622 is preferably between 3 and 20 cm, more preferably between 8 and 15 cm, and is chosen so that when the aortic catheter 1600 is deployed and the upstream occlusion member 1620 is positioned within the ascending aorta between the coronary arteries and the brachiocephalic artery, the downstream anchoring member 1622 will be positioned in the descending aorta downstream of the left subclavian artery. The downstream occlusion member 1622 in this embodiment is in the form of an expandable, inflatable balloon bonded to the catheter shaft 1602 by heat welding or with an adhesive. Suitable materials for the inflatable balloon downstream anchoring member 1622 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof In addition, the outer surface of the downstream anchoring member 1622 may include a friction increasing coating or texture to increase friction with the aortic wall when deployed.

The inflatable downstream occlusion member 1622 has a deflated state, in which the diameter of the occlusion member 1622 is preferably not much larger than the diameter of the catheter shaft 1602, and an inflated state, in which the occlusion member 1622 expands to a diameter capable of regulating blood flow in the descending aorta of the patient. Therefore, to gain desired results the downstream occlusion member may be completely inflated, or partially inflated. For use in adult human patients, the downstream occlusion member 1622 preferably has an inflated outer diameter of approximately 1.0 cm to 5.0 cm and a length of approximately 1.0 cm to 7.5 cm.

The corporeal perfision lumen 1608 extends through the catheter shaft 1602 from the proximal end 1604 to one or more corporeal perfusion ports 1624 on the exterior of the catheter shaft 1602 proximal of the downstream occlusion member 1622. The arch perfusion lumen 1610 extends through the catheter shaft 1602 from the proximal end 1604 to one or more arch perfusion ports 1626 on the exterior of the catheter shaft 1602 between the upstream occlusion member 1620 and the downstream occlusion member 1622. A common balloon inflation lumen 1612 extends through the catheter shaft 1602 from the proximal end 1604 to balloon inflation ports 1632 and 1630 which reside in the interior of downstream occlusion balloon 1622 and the upstream occlusion balloon 1620 respectively. Alternatively, separate inflation lumens can be implemented to separately inflate the downstream occlusion member 1622 and the upstream occlusion member 1620.

The arch monitoring lumen 1614 extends through the catheter shaft 1602 from the proximal end 1604 to an arch monitoring port 1634 proximal to the upstream occlusion member 1620 to monitor pressure in the aortic arch though the lumen 1614 or by providing a separate sensor slidably disposed in the lumen 1614. The root pressure lumen 1618 extends through the catheter shaft 1602 from the proximal end 1604 to a root pressure port 1628 near the distal end 1606 of the catheter shaft 1602 to monitor pressure in the aortic root through the lumen 1618 or through a separate sensor slidably disposed in the lumen 1618. The guide wire and cardioplegia lumen 1616 extends from the proximal end 904 of the catheter shaft 1602 to a guide wire/cardioplegia port 1636 at the distal end 1606 of the catheter shaft 1602, distal to the upstream occlusion member 1620. Preferably, the distal end 1606 of the catheter shaft 1602 is smoothly tapered or rounded for easy introduction and to avoid trauma or injury to the aortic wall during insertion or withdrawal of the aortic catheter 1600.

Preferably, the aortic catheter 1600 includes one or more markers, which may include radiopaque markers and/or sonoreflective markers, to enhance imaging of the aortic catheter 900 using fluoroscopy or ultrasound, such as transesophageal echocardiography (TEE). In this illustrative embodiment, the aortic catheter 1600 includes a distal radiopaque marker 1638 positioned near the distal end 1606 of the catheter shaft 1602, an intermediate radiopaque marker 1640 positioned near the proximal edge of the upstream occlusion member 1620, and a proximal radiopaque marker 1642 positioned near the distal edge of the downstream anchoring member 1622. Each of the radiopaque markers 1638, 1640, 1642 may be made of a ring of dense radiopaque metal, such as gold, platinum, tantalum, tungsten or alloys thereof, or a ring of a polymer or adhesive material heavily loaded with a radiopaque filler material.

The proximal end 1604 of the catheter shaft 1602 is connected to a manifold 1650 with fittings for each of the catheter lumens. The corporeal perfusion lumen 1608 is connected to a Y-fitting 1662 that has a barb connector 1652 for connection to a perfusion pump or the like and a luer connector 1654, which may be used for monitoring perfusion pressure, temperature, chemical compositions and for withdrawing fluid samples or for injecting medications or other fluids. Likewise, the arch perfusion lumen 1610 is connected to a Y-fitting 1664 that has a barb connector 1656 for connection to a perfusion pump and a luer connector 1658 which may be used for monitoring arch perfusion pressure, temperature, chemical compositions and for withdrawing fluid samples or for injecting medications or other fluids. The common balloon inflation lumen 1612 is connected to a stopcock or luer connector 1660 or other fitting suitable for connection to a syringe or balloon inflation device. In addition the inflation lumen may have a pressure monitoring balloon proximal or distal to the stopcock or luer fitting to give visible and tactile feedback concerning the balloon inflation pressure. The guide wire and cardioplegia lumen 1616 is connected to a three-way Y-fitting 1670 that has a barb connector 1672 for connection to a cardioplegia infusion pump, a luer connector 1674 capable of monitoring root perfusion pressure, temperature and chemical compositions and a guide wire port 1676 with a Touhy-Borst adapter or other hemostasis valve. The root pressure lumen 1618 is connected to a luer connector 1668 or other fitting suitable capable of monitoring arch perfusion pressure, temperature and chemical compositions or for withdrawing fluid samples. The arch monitoring lumen 1614 is connected to a luer connector 1666 or other fitting suitable capable of monitoring arch perfusion pressure, temperature, chemical compositions or for withdrawing fluid samples.

FIG. 19 illustrates a side view of a coaxial dual lumen venous drainage cannula 1999 of the present invention configured for introduction through the patient's inferior vena cava via the femoral vein or other suitable venous access point in the lower extremities. Alternatively, the coaxial dual lumen venous drainage cannula 1999 may be configured for introduction though the patient's superior vena cava via the jugular vein or other suitable venous access point in the neck or upper extremities. The elongated coaxial tubular shaft 1998 may be fabricated separately by known extrusion methods and joined together end-to-end, for example by heat welding or by adhesive bonding. Alternatively, the elongated coaxial tubular shaft 1998 may be fabricated by dipping or by composite construction techniques and joined together or the entire elongated coaxial tubular shaft 1998 may be fabricated integrally. Suitable materials for the elongated coaxial tubular shaft 1998 include, but are not limited to, polyvinylchloride, polyurethane, polyethylene, polypropylene, polyamides (nylons), polyesters, silicone, latex, and alloys or copolymers thereof, as well as braided, coiled or counterwound wire or filament reinforced composites.

FIG. 20 is a magnified lateral cross section of the coaxial dual lumen venous drainage cannula 1999 taken along line 20—20 of FIG. 19. FIG. 21 is a magnified lateral cross section of the coaxial dual lumen venous drainage cannula 1999 taken along line 21—21 of FIG. 19. Collectively FIGS. 19 through 21 illustrate the multi-lumen arrangement wherein the inner tubular shaft 1915 and an outer tubular shaft 1917 are configured in a coaxial relationship such that an annular space is created therebetween, which defines the corporeal venous drainage lumen 1989. The venous coaxial multi-lumen drainage cannula 1900 is further comprised of a cerebral drainage lumen 1988, which is defined by the internal diameter of the inner tubular shaft 1915, a first balloon inflation lumen 1991, and a second balloon inflation lumen 1994. The tubular shaft 1998 preferably has a length of approximately 15 cm to 90 cm and a diameter of approximately 10 to 32 French (3.3 mm to 10.7 mm diameter).

The dual-lumen venous drainage cannula 1999 includes a first occlusion balloon 1997 or other expandable occlusion member, mounted on the tubular shaft 1998, which is positioned within the patient's superior vena cava when in the operative position, and a second occlusion balloon 1996 or other expandable occlusion member, mounted on the tubular shaft 1998, which is positioned within the patient's inferior vena cava when in the operative position to create a segmentation of venous blood flow in the superior and inferior vena cava. Suitable materials for the first occlusion member 1997 and the second occlusion member 1996 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. The occlusion balloons 1996 and 1997 preferably have an expanded diameter of approximately 5 mm to 40 mm. When the coaxial dual-lumen venous drainage cannula 1999 is configured for femoral artery introduction, the first occlusion balloon 1997 is mounted near the distal end 1995 of the inner tubular shaft 1915 and the second occlusion balloon 1996 is mounted somewhat proximal to the first balloon 1997, on the outer tubular shaft 1917. Alternatively, for jugular vein introduction, the positions of the occlusion balloons are reversed.

A first balloon inflation lumen 1991 is connected to a stopcock 1990 that extends through the tubular shaft 1998 to a balloon inflation port 1992 within the first occlusion balloon 1997. The second balloon inflation lumen 1994, is connected to a stopcock 1993, that extends through the tubular shaft 1998 to a balloon inflation port 1923 within the second occlusion balloon 1996.

The cerebral venous drainage lumen 1988 extends from a proximal venous drainage fitting 1987 in fluid communication with an external CPB machine through the tubular shaft 1998, to one or more superior vena cava drainage ports 1995 on the tubular shaft 1998 distal to the first occlusion balloon 1997. In addition, venous drainage ports 1982 which are proximal to the first occlusion balloon 1997 are also in fluid communication with the first venous drainage lumen 1988. Alternatively, the venous drainage ports 1982 may be in fluid communication with the corporeal venous drainage lumen 1989. Alternatively, a separate lumen may be provided to completely isolate the myocardial circulation. The corporeal venous drainage lumen 1989 extends from a proximal venous drainage fitting 1981 in fluid communication with an external CPB machine through the tubular shaft 1998, to one or more inferior vena cava drainage ports 1978 on the tubular shaft 1998 proximal to the second occlusion balloon 1996. Preferably, the distal portion of the tubular shaft 1998 is smoothly tapered or rounded for easy introduction and to avoid trauma or injury to vena cava during insertion or withdrawal of the coaxial multi-lumen venous cannula 1999.

Preferably, the coaxial multi-lumen venous cannula 1999 includes one or more markers, which may include radiopaque markers and/or sonoreflective markers, to enhance imaging of the venous cannula 1999 using fluoroscopy or ultrasound, such as transesophageal echocardiography (TEE). In this illustrative embodiment, the multilumen coaxial venous drainage cannula 1999 includes a distal radiopaque marker 1908 positioned. near the distal end of the tubular shaft 1998, an intermediate radiopaque marker 1977 positioned near the drainage ports 1982, and a proximal radiopaque marker 1976 positioned near the distal edge of the second occlusion member 1996. Each of the radiopaque markers 1908, 1977, 1976 may be made of a ring of dense radiopaque metal, such as gold, platinum, tantalum, tungsten or alloys thereof, or a ring of a polymer or adhesive material heavily loaded with a radiopaque filler material.

The proximal end 1983 of the coaxial multi-lumen venous drainage cannula 1999 is capable of receiving the inner tubular member and creating a fluid tight seal through the Touhy-Borst adapter 1931 or other suitable hemostasis valve capable of receiving a second catheter instrument. The cerebral venous drainage lumen 1988 is coupled to a Y-fitting 1987 that has a barb connector 1986 for connection to an external CPB machine, a luer connector 1985 capable of monitoring superior vena cava pressure, temperature and chemical compositions. The corporeal venous drainage lumen 1989 is coupled to a three-way fitting 1981 having a barb connector 1980, or other suitable fitting capable of being coupled to a CPB machine, a luer fitting 1979 capable of monitoring inferior vena cava pressure, temperature and chemical compositions and a guide wire port 1984 with a Touhy-Borst adapter 1931 or other hemostasis valve. A first inflation lumen 1991 is coupled to a stopcock 1990, or other suitable fitting capable of being attached to an inflation mechanism and a second inflation lumen 1994 is coupled to a stopcock 1993, or other suitable fitting capable of being attached to an inflation mechanism. In addition, each inflation lumen may have an individual pressure-monitoring device proximal or distal to the stopcock to provide visible and tactile feedback concerning the balloon inflation pressures.

Figure 22:
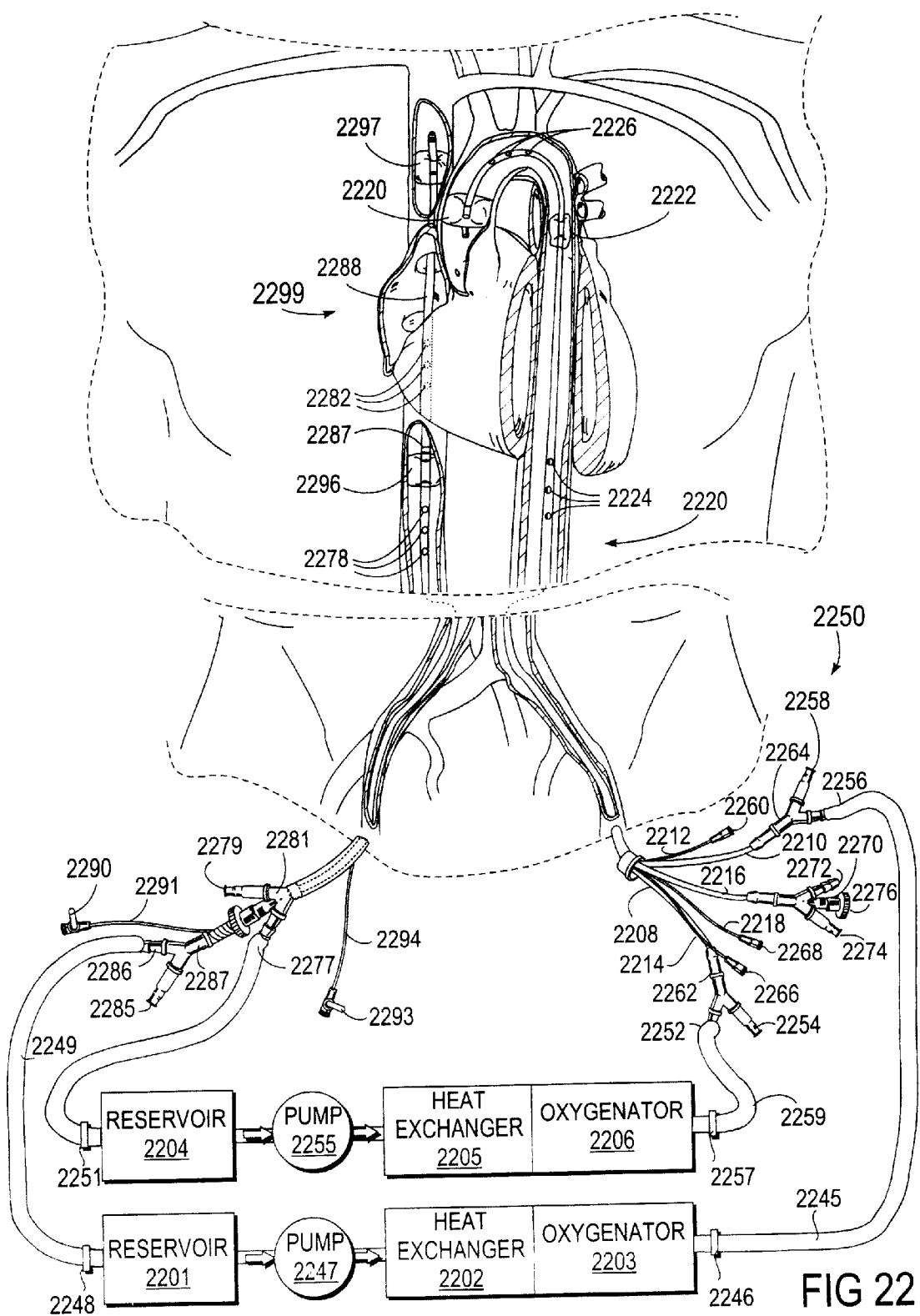
FIG. 22 illustrates a third embodiment of the support system of the present invention configured for selective, isolated, dual-loop perfusion of a patient's circulatory system.
Figure 23:
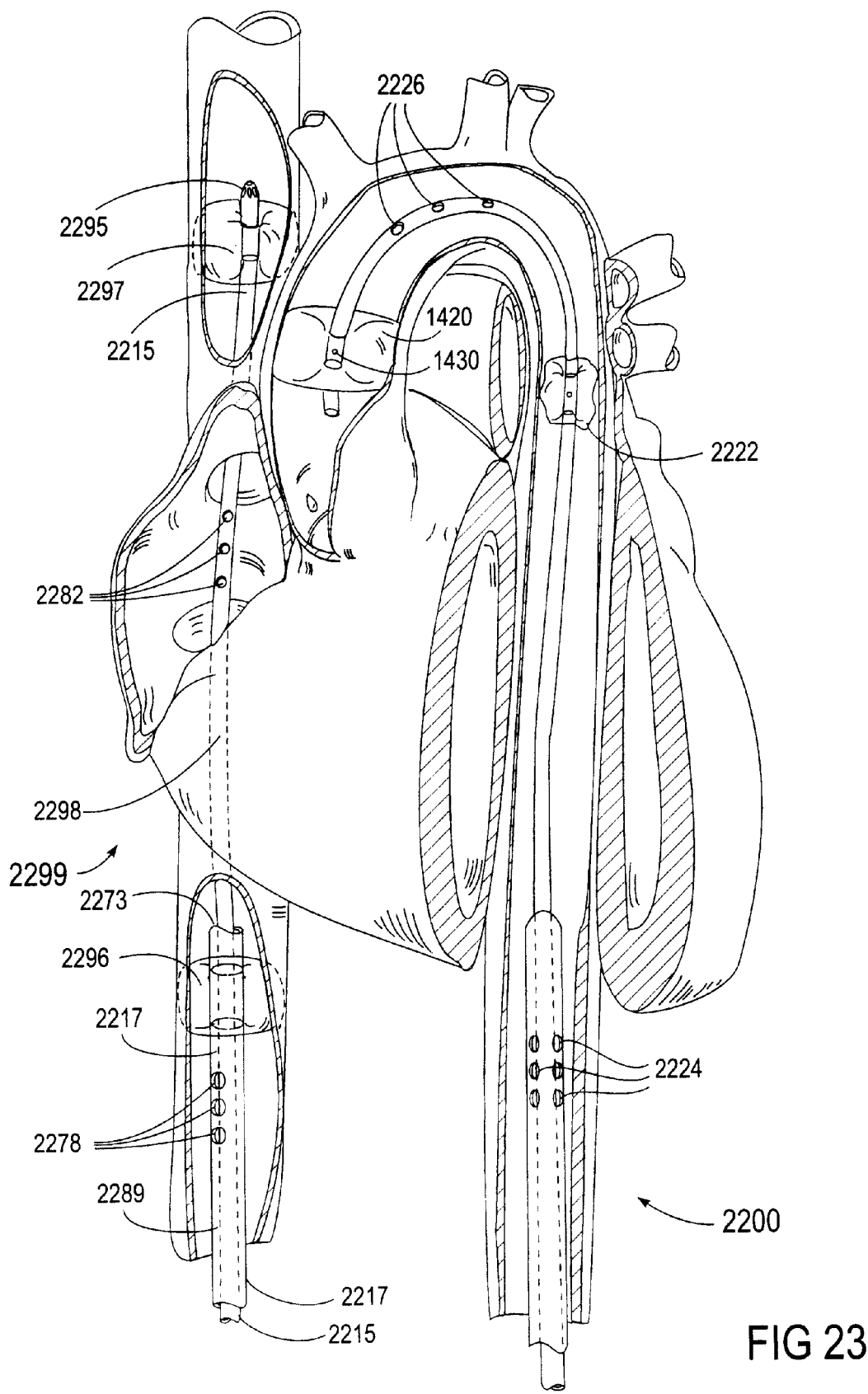
FIG. 23 is a cutaway close-up view of the cannula placement of FIG. 22 with a portion of the patient's heart cut away to better show the descending aorta.

FIG. 22 illustrates a third embodiment of the support system of the present invention configured for selective, isolated, dual-loop perfusion of a patient's circulatory system. The circulatory support system has a cerebral loop for perfusion of the patient's cerebral circulation and upper extremities and a separate corporeal loop for perfusion of the patient's viscera and lower extremities. As in the previously described embodiments, the patient's coronary circulation may optionally be included in the cerebral loop or the corporeal loop or a third, isolated coronary loop may be created. In this embodiment of the circulatory support system, arterial cannulation is provided by a dual-balloon, coaxial selective arterial perfusion cannula 2200 and venous cannulation is provided by a dual-lumen, coaxial venous drainage cannula 2299. A cutaway close-up view of the cannula placement is shown in FIG. 23 with a portion of the patient's heart cut away to better show the descending aorta.

The dual-lumen, coaxial venous drainage cannula 2299 may be configured for introduction though the patient's inferior vena cava via the femoral vein or other suitable venous access point in the lower extremities, as shown, or, alternatively, it may configured for introduction through the patient's superior vena cava via the jugular vein or other suitable venous access point in the neck or upper extremities. The dual-lumen coaxial venous drainage cannula 2299 has an inner tubular shaft 2215 that includes a first venous drainage lumen 2288 for draining venous blood from the patient's superior vena cava and an outer, coaxial tubular shaft 2217 that includes a second, coaxial venous drainage lumen 2289 for draining venous blood from the patient's inferior vena cava. In addition, the inner tubular shaft 2215 includes a first balloon inflation lumen 2291 and the outer tubular shaft 2217 includes a second balloon inflation lumen 2294 for inflating the balloons to enable the segmentation of the vena cava to isolate the cerebra, corporeal and myocardial circulation. The inner and outer tubular shafts 2215 and 2217 preferably have a length of approximately 15 cm to 90 cm and the outer tubular shaft 2217 preferably has a diameter of approximately 10 to 32 French (3.3 mm to 10.7 mm diameter). A first occlusion balloon 2297 or other expandable occlusion member mounted near the distal end of the inner tubular shaft 2215 and a second occlusion balloon 2296 or other expandable occlusion member is mounted near the distal end of the outer tubular shaft 2217. The occlusion balloons 2297 and 2296 or other expandable occlusion members preferably have an expanded diameter of approximately 5 mm to 40 mm. The inner tubular shaft 2215 is slidable within a hemostasis seal 2231 at the proximal end of the outer tubular shaft 2217. This allows adjustment of the distance between the first occlusion balloon 2297 and second occlusion balloon 2296 so that the first occlusion balloon 2297 can be positioned within the patient's superior vena cava, and the second occlusion balloon 2296 can be positioned within the patient's inferior vena cava. Preferably, the hemostasis seal includes a Touhy-Borst fitting or other compression seal that allows the user to selectively lock the relative position of the inner 2215 and outer 2217 tubular shafts. Optionally, a sliding hemostasis seal may be used at the distal end of the outer tubular shaft to seal the annular space between the inner and outer tubular shafts.

The superior vena cava drainage lumen 2288 extends through the inner tubular shaft 2215 from a first venous drainage fitting 2287 on the proximal end of the inner tubular shaft 2215 to one or more superior vena cava drainage ports 2295 on the inner tubular shaft 2215 distal to the first occlusion balloon 2297. The superior vena cava drainage lumen 2288 may also connect to a distal guidewire port on the end of the inner tubular shaft 2215 distal to the first occlusion balloon 2297. The second venous drainage lumen 2289 extends through the tubular shaft 2298 within the annular space from a second venous drainage fitting 2281 on the proximal end of the outer tubular shaft 2217 to one or more inferior vena cava drainage ports 2278 on the outer tubular shaft proximal to the second occlusion balloon 2296. In addition, extra drainage can also be accomplished through an annular opening 2273, and extra venous drainage ports 2282 distal to the second occlusion balloon 2296.

The cerebral loop of the circulatory support system is created by connecting the superior vena cava venous drainage lumen 2288 of the inner tubular shaft 2215 to the inflow 2248 of a first blood circulation pump 2247 using suitable blood flow tubing 2249, then connecting the outflow 2246 of the first blood circulation pump 2247 to the arch perfusion lumen 2210 of the arterial cannula 2200. The first blood circulation pump 2247 may be a peristaltic roller pump, a centrifugal blood pump or other suitable blood circulation pump. Preferably, the cerebral loop of the circulatory support system will also include a venous blood reservoir 2201, a blood oxygenator 2203 and heat exchanger 2202 in series with the first blood circulation pump 2247. Optionally, vacuum assist may be used to enhance venous drainage through the first venous drainage lumen 2288 of the inner tubular shaft 2215. Venous blood from the head and upper extremities is partitioned into the superior vena cava lumen 2288 by the first occlusion balloon 2297 and is drained out through the superior vena cava venous drainage lumen 2288 of the inner tubular shaft 2215. The blood is oxygenated, cooled and recirculated by the first blood circulation pump 2247 to the head and upper extremities through the arch perfusion lumen 2210 of the arterial cannula 2200.

The corporeal loop of the circulatory support system is created by connecting the inferior vena cava venous drainage lumen 2289 of the outer tubular shaft 2217 to the inflow 2251 of a second blood circulation pump 2255 using suitable blood flow tubing 2277, then connecting the outflow of the second blood circulation pump 2255 to the corporeal perfusion lumen 2208 of the arterial cannula 2200. The second blood circulation pump 2255 may be a peristaltic roller pump, a centrifugal blood pump or other suitable blood circulation pump. Preferably, the corporeal loop of the circulatory support system will also include a venous blood reservoir 2204, a blood oxygenator 2206 and heat exchanger 2205 in series with the second blood circulation pump 2255. Optionally, vacuum assist may be used to enhance venous drainage through the inferior vena cava venous drainage lumen 2289 of the tubular shaft 2298. Venous blood from the viscera and lower extremities enters the patient's inferior vena cava and is partitioned into the inferior vena cava venous drainage lumen 2289 by the second occlusion balloon 2296 and is drained out through the inferior vena cava venous drainage lumen 2289. The blood is oxygenated, cooled and recirculated by the second blood circulation pump 2255 to the viscera and lower extremities through the corporeal perfusion lumen 2208 of the arterial cannula 2200.

The dual-lumen, coaxial venous drainage cannula 2299 also includes one or more drainage ports 2282 connected with the first venous drainage lumen 2288 on the inner tubular shaft 2215 between the first and second balloons 2297 and 2296 for draining the patient's right atrium and the coronary sinus as part of the cerebral loop. Alternatively, the patient's right atrium and the coronary sinus may be drained into the inferior vena cava venous drainage lumen 2289 through the annular space 2273 between the inner 2215 and outer 2217 tubular shafts as part of the corporeal loop. Optionally, the dual-lumen, coaxial venous drainage cannula 2299 may be made without either the first occlusion balloon 2297 or the second occlusion balloon 2296 or one of the balloons may be deflated when isolation of the patient's right atrium and the coronary sinus is not needed. Alternatively, the dual-lumen, coaxial venous drainage cannula 2299 may be provided with a third venous drainage lumen within the inner or outer tubular shaft connected to drainage ports between the first 2297 and second 2296 balloons for draining the patient's right atrium and the coronary sinus. A separate coronary perfusion loop can be created by connecting the third venous drainage lumen to the inflow of a third blood circulation pump and connecting the outflow of the pump to the cardioplegia lumen 2216 of the arterial cannula 2200. The third blood circulation pump may be a peristaltic roller pump, a centrifugal blood pump or other suitable blood circulation pump. Preferably, the coronary loop also includes a venous blood reservoir, a blood oxygenator and heat exchanger in series with the third blood circulation pump.

FIGS. 24 though 29 collectively illustrate a fourth embodiment of the circulatory support system of the present invention configured for selective, isolated, dual-loop perfusion of a patient's circulatory system. The circulatory support system has a cerebral loop for perfusion of the patient's cerebral circulation and upper extremities and a separate corporeal loop for perfusion of the patient's viscera and lower extremities. Optionally, the patient's coronary circulation may be included in the cerebral loop or the corporeal loop or a third, isolated coronary loop may be created. In this illustrative embodiment, arterial cannulation is provided by a low profile peripheral arterial cannulation subsystem that includes an aortic arch perfusion cannula 2400 and a separate corporeal perfusion cannula 2401. Venous cannulation may be provided by any of previously described venous cannulae, for illustrative purposes, a superior vena cava cannula 399 as described in FIGS. 3 and 4 is used in conjunction with a separate inferior vena cava cannula 589 which was also fully described in FIGS. 5 and 6, there descriptions are incorporated by reference herein. The use of a low profile peripheral arterial cannulation subsystem with separate superior and inferior vena cava cannulae allows easier cannulation of patients with smaller peripheral arteries, such as pediatric patients and smaller adults, particularly women. The low profile peripheral arterial cannulation subsystem also allows percutaneous cannulation, without an arterial cutdown, in adult patients with normal sized peripheral arteries.

FIG. 24 illustrates an aortic arch perfusion cannula of the present invention configured for introduction into the aortic arch through peripheral arterial access in one of the upper extremities, such as the left or right subclavian artery, axillary artery or brachial artery. Alternatively, a two catheter arterial system may also be accomplished by cannulating both femoral arteries in a contralateral approach, or by cannulating the same femoral artery with the second arterial cannula in a collateral approach. The aortic arch perfusion cannula 2400 has a tubular shaft 2402 preferably having a length of approximately 15 cm to 90 cm and a diameter of approximately 10 to 32 French (3.3 mm to 10.7 mm diameter). In order to facilitate placement of the aortic arch catheter 2400 and to improve the stability of the catheter 2400 in the proper position in the patient's aorta, a distal region 2444 of the catheter shaft 2402 may be preshaped with a curve to match the internal curvature of the patient's aortic arch. The curved distal region 2444 represents an S-shaped curve to match the typical curvature of the aortic arch in an adult human patient. In addition, the distal end 2406 of the catheter may be skewed slightly up out of the plane of the curve to accommodate the forward angulation of the patient's ascending aorta. Additionally, the catheter shaft 2402 may be reinforced, particularly in the curved distal region 2444, for example with braided or coiled wire, to further improve the stability of the catheter 2400 in the proper position in the patient's aorta.

Illustrated in FIG. 25, is a magnified lateral cross section of the aortic arch perfusion cannula 2400 of FIG. 24 taken along line 25—25 of FIG. 24 showing the multi-lumen arrangement of the catheter shaft 2402. The cannula shaft 2402 has four lumens including, an arch perfusion lumen 2410, a balloon inflation lumen 2412, a cardioplegia lumen 2416 and, a root pressure lumen 2418.

Referring collectively to FIGS. 24 and 25, an occlusion balloon 2420 or other expandable occlusion member is mounted near the distal end 2406 of the tubular shaft 2402 so that it will be positioned in the ascending aorta between the coronary arteries and the right brachiocephalic artery, when the balloon 2420 is deployed. The arch perfusion lumen 2410 extends through the tubular shaft 2402 from an arch perfusion fitting 2464 on the proximal end of the cannula 2400 to one or more arch perfusion ports 2426 on the tubular shaft 2402 proximal to the occlusion balloon 2420. The cardioplegia lumen 2416 extends through the tubular shaft 2402 from a cardioplegia fitting 2470 on the proximal end of the cannula 2400 to one or more cardioplegia ports 2436 on the tubular shaft 2402 distal to the occlusion balloon 2420. The cardioplegia lumen 2416 may also serve as a guide wire lumen. In these alternative embodiments a Touhy-Borst fitting 2476 is in fluid communication with the cardioplegia lumen 2416 and is sized and dimensioned for receiving a guide wire to aid in the insertion and placement of the cannula 2400. A root pressure lumen 2418 extends through the tubular shaft 2402 from a root pressure fitting 2468 on the proximal end of the catheter 2402 to one or more pressure ports 2428 on the tubular shaft 2402 distal to the occlusion balloon 2420. The balloon inflation lumen 2412 extends through the tubular shaft 2402 from a balloon inflation fitting 2460 on the proximal end of the cannula 2400 to a balloon inflation port 2430 within the occlusion balloon 2420. In addition, a separate arch monitoring lumen may be incorporated to allow the monitoring of pressure in the aortic arch proximal to the occlusion balloon 2420. Alternatively, the arch monitoring lumen may be sized and configured to slidably receive an arch monitoring sensor to be inserted therethrough to take measurements in the arch.

Preferably, the aortic arch catheter 2400 includes one or more markers, which may include radiopaque markers and/or sonoreflective markers, to enhance imaging of the aortic arch catheter 2400 using fluoroscopy or ultrasound, such as transesophageal echocardiography (TEE). In this illustrative embodiment, the aortic arch catheter 2400 includes a distal radiopaque marker 2438 positioned near the distal end 2406 of the catheter shaft 2402, an intermediate radiopaque marker 2440 positioned near the proximal edge of the occlusion member 2420. Each of the radiopaque markers 2438 and 2440 may be made of a ring of dense radiopaque metal, such as gold, platinum, tantalum, tungsten or alloys thereof, or a ring of a polymer or adhesive material heavily loaded with a radiopaque filler material.

The proximal end 2404 of the aortic arch catheter shaft 2402 is connected to a manifold 2450 with fittings for each of the catheter lumens. The arch perfusion lumen 2410 is connected to a Y-fitting 2464 that has a barb connector 2456 for connection to a perfusion pump and a luer connector 2458. The balloon inflation lumen 2412 is connected to a stopcock 2460 or other fittings suitable for connection to a syringe or balloon inflation device. The guide wire and cardioplegia lumen 2416 is connected to a three-way Y-fitting 2470 that has a barb connector 2472 for connection to a cardioplegia infusion pump, a luer connector 2474 and a guide wire port 2476 with a Touhy-Borst adapter or other hemostasis valve. The root pressure lumen 2418 is connected to a luer connector 2468 or other fitting suitable for connection to a pressure monitor.

Figures 26, 27:
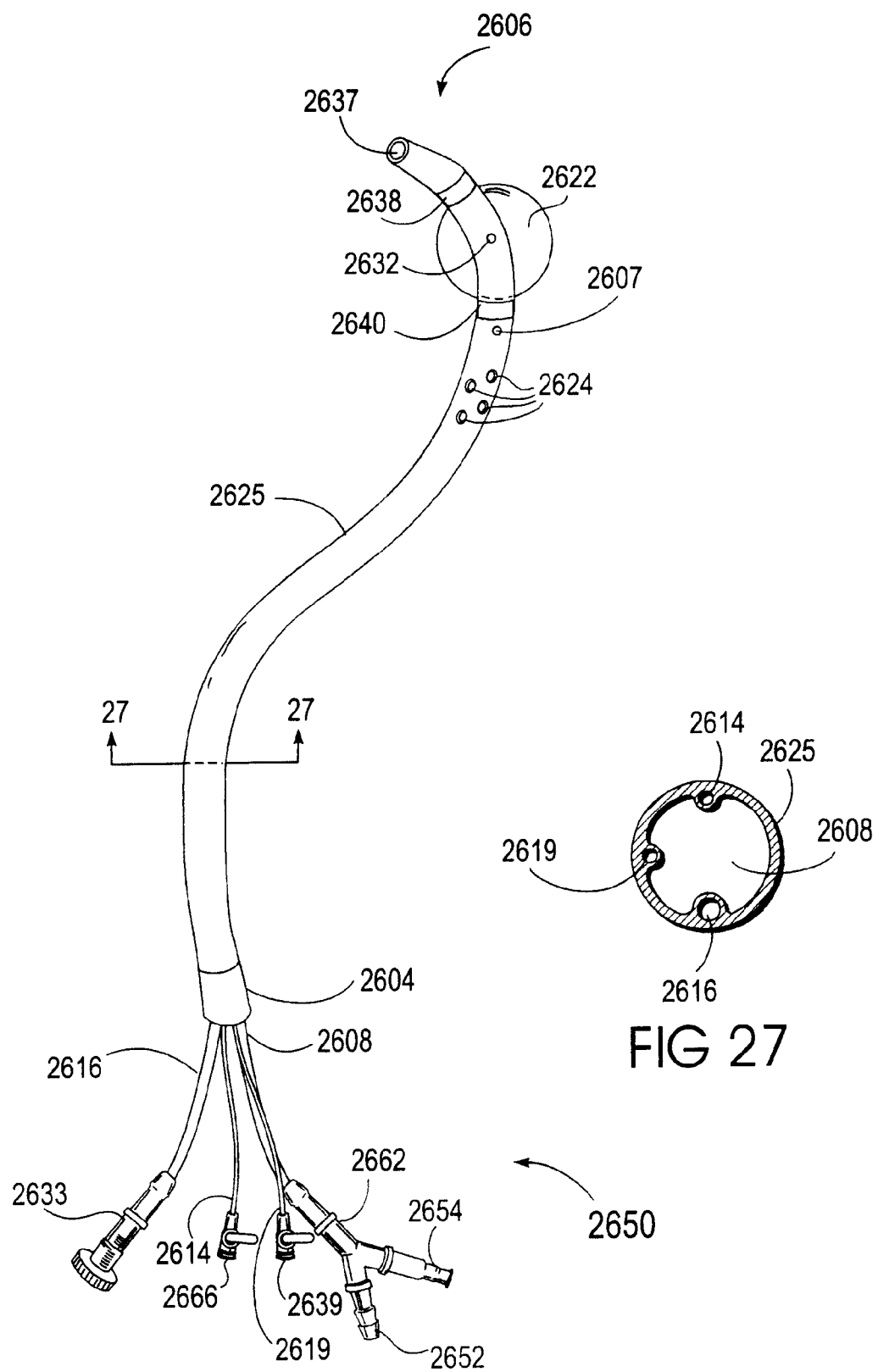
FIG. 26 illustrates a corporeal perfusion cannula of the present invention configured for introduction into the descending aorta through a peripheral arterial access in one of the lower extremities, such as the femoral artery.
FIG. 27 is a magnified lateral cross section of the corporeal perfusion cannula taken along line 27—27 of FIG. 26 showing the multi-lumen arrangement of the catheter shaft.

FIG. 26 illustrates a corporeal perfusion cannula of the present invention configured for introduction into the descending aorta through a peripheral arterial access in one of the lower extremities, such as the femoral artery. The corporeal perfusion cannula 2601 has a tubular shaft 2625 preferably having a length of approximately 15 cm to 90 cm and a diameter of approximately 10 to 32 French (3.3 mm to 10.7 mm diameter). The catheter shaft 2602 may be reinforced, for example with braided or coiled wire, to further improve the stability of the catheter 2600 in the proper position in the patient's aorta.

Illustrated in FIG. 27 is a magnified lateral cross section of the corporeal perfusion cannula 2601 taken along line 27—27 of FIG. 26 showing the multi-lumen arrangement of the catheter shaft 2689. The tubular shaft 2625 has four lumens including; a corporeal perfusion lumen 2608, a balloon inflation lumen 2614, a guide wire lumen 2616 and an arch monitoring lumen 2619.

Referring collectively to FIGS. 26 and 27, an occlusion balloon 2622 or other expandable occlusion member is mounted near the distal end of the tubular shaft 2625. The corporeal perfusion lumen 2608 extends through the tubular shaft 2625 from a corporeal perfusion fitting 2662 on the proximal end of the cannula 2604 to one or more corporeal perfusion ports 2624 on the tubular shaft 2625 proximal to the occlusion balloon 2622. The guide wire lumen 2616 extends through the tubular shaft 2625 from a guide wire fitting 2633 on the proximal end 2604 of the cannula 2600 to a guide wire port 2637 on the tubular shaft 2625 distal to the occlusion balloon 2622. The balloon inflation lumen 2614 extends through the tubular shaft 2625 from a balloon inflation fitting 2666 on the proximal end 2604 of the cannula 2600 to a balloon inflation port 2632 within the occlusion balloon 2622. A corporeal pressure monitoring lumen 2619 extends through the tubular shaft 2625 from a pressure monitoring fitting 2639 on the proximal end 2604 of the cannula 2600 to a corporeal pressure port 2607 on the tubular shaft 2625 proximal to the occlusion balloon 2622.

Preferably, the corporeal catheter 2601 includes one or more markers, which may include radiopaque markers and/or sonoreflective markers, to enhance imaging of the aortic catheter 100 using fluoroscopy or ultrasound, such as transesophageal echocardiography (TEE). In this illustrative embodiment, the corporeal catheter 2601 includes a distal radiopaque marker 2638 positioned near the distal end 2606 of the catheter shaft 2625, an intermediate radiopaque marker 2640 positioned near the proximal edge of the occlusion member 2622, and a proximal radiopaque marker 2640 positioned near the distal edge of the anchoring member 2622. Each of the radiopaque markers 2638 and 2640 may be made of a ring of dense radiopaque metal, such as gold, platinum, tantalum, tungsten or alloys thereof, or a ring of a polymer or adhesive material heavily loaded with a radiopaque filler material.

The proximal end 2604 of the catheter shaft 2625 is connected to a manifold 2650 with fittings for each of the catheter lumens. The corporeal perfusion lumen 2608 is connected to a Y-fitting 2662 that has a barb connector 2652 for connection to a perfusion pump or the like and a luer connector 2654, which may be used for monitoring perfusion pressure, for withdrawing fluid samples or for injecting medications or other fluids. The balloon inflation lumen 2614 is connected to a stopcock connector 2666 or other fitting suitable for connection to a syringe or balloon inflation device. The guide wire lumen 2616 is connected to a Touhy-Borst adapter 2633 or other hemostasis valve. The corporeal pressure lumen 2619 is connected to a luer connector 2639 or other fitting suitable for connection to a pressure monitor.

Figure 28:
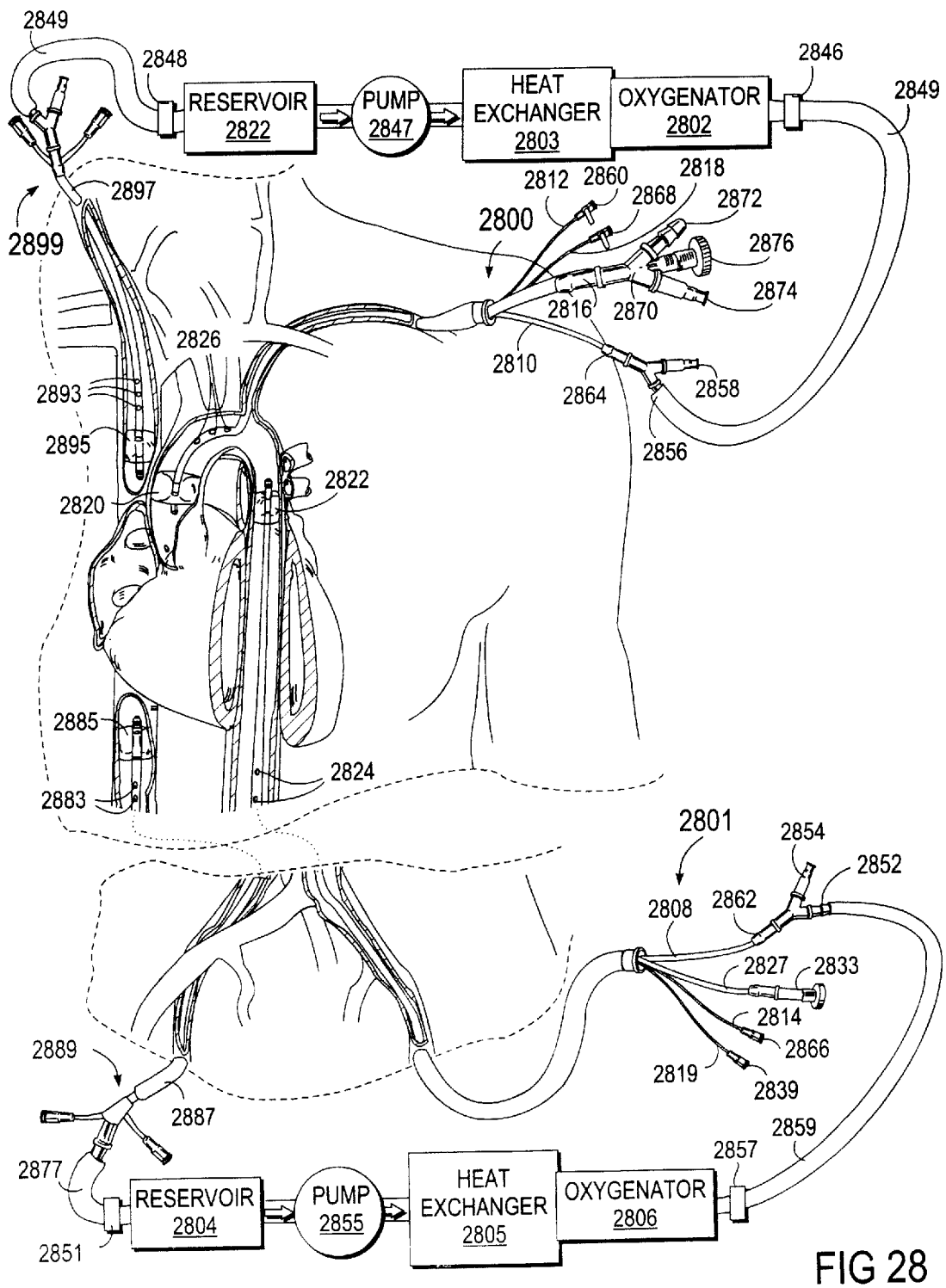
FIG. 28 illustrates a fourth embodiment of the support system of the present invention configured for selective, isolated, dual-loop perfusion of a patient's circulatory system.

FIG. 28 illustrates the circulatory support system of the present invention configured for selective, isolated, dual-loop perfusion of a patient's circulatory system. The cerebral loop of the circulatory support system is created by connecting the venous drainage lumen 2897 of the superior vena cava cannula 2899 to the inflow 2848 of a first blood circulation pump 2847 using suitable blood flow tubing 2849, then connecting the outflow 2846 of the first blood circulation pump 2847 to the arch perfusion lumen 2810 of the arch perfusion cannula 2800. The first blood circulation pump 2847 may be a peristaltic roller pump, a centrifugal blood pump or other suitable blood circulation pump. Preferably, the cerebral loop of the circulatory support system will also include a venous blood reservoir 2822, a blood oxygenator 2802 and heat exchanger 2803 in series with the first blood circulation pump. Optionally, vacuum assist may be used to enhance venous drainage through the superior vena cava cannula 2899. Venous blood from the head and upper extremities enters the patient's superior vena cava and is drained out through the venous drainage lumen 2897 of the superior vena cava cannula 2899. The blood is oxygenated, cooled and recirculated by the first blood circulation pump 2847 to the head and upper extremities through the arch perfusion lumen 2810 of the arch perfusion cannula 2800.

The corporeal loop of the circulatory support system is created by connecting the venous drainage lumen 2887 of the inferior vena cava cannula 2889 to the inflow 2851 of a second blood circulation pump 2855 using suitable blood flow tubing 2877, then connecting the outflow 2857 of the second blood circulation pump 2855 to the corporeal perfusion lumen 2808 of the corporeal perfusion cannula 2801. The second blood circulation pump 2855 may be a peristaltic roller pump, a centrifugal blood pump or other suitable blood circulation pump. Preferably, the corporeal loop of the circulatory support system will also include a venous blood reservoir 2804, a blood oxygenator 2806 and heat exchanger 2805 in series with the second blood circulation pump. Optionally, vacuum assist may be used to enhance venous drainage through the inferior vena cava cannula 2889. Venous blood from the viscera and lower extremities enters the patient's inferior vena cava and is drained out through the venous drainage lumen 2887 of the inferior vena cava cannula 2889. The blood is oxygenated, cooled or warmed and recirculated by the second blood circulation pump 2855 to the viscera and lower extremities through the corporeal perfusion lumen 2808 of the corporeal perfusion cannula 2801.

FIGS. 29 through 35 collectively illustrate a fifth embodiment of the circulatory support system of the present invention configured for selective, isolated, dual-loop perfusion of a patient's circulatory system. This embodiment of the circulatory support system is configured for central venous and central arterial cannulation using open-chest:,or minimally-invasive surgical techniques, for example by insertion through a minithoracotomy, partial sternotomy, median sternotomy or thorocotomy. The circulatory support system has a cerebral loop for perfusion of the patient's cerebral circulation and upper extremities and a separate corporeal loop for perfusion of the patient's viscera and lower extremities. Optionally, the patient's coronary circulation may be included in the cerebral loop or the corporeal loop or a third, isolated coronary loop may be created. In this embodiment of the circulatory support system, arterial cannulation is provided by a dual-balloon, selective, central arterial perfusion cannula 2900, and venous cannulation is provided by a central superior vena cava cannula 3199 and a separate central inferior vena cava cannula 3189.

FIG. 29 illustrates a side view of the dual-balloon, selective, central arterial perfusion cannula 2900 is configured for antegrade introduction into the patient's aortic arch via a direct puncture or incision in. the ascending aorta. Because the aortic catheter 2900. is introduced directly into the ascending aorta, the elongated catheter shaft 2902 has an overall length of approximately 20 to 60 cm. In order to facilitate placement of the aortic catheter 2900 and to improve the stability of the catheter 2900 in the proper position in the patient's aorta, a distal region 2944 of the catheter shaft 2902 may be preshaped with a curve to match the internal curvature of the patient's aortic arch. The curved distal region 2944 represents an S-shaped curve with a primary curve 2946 of approximately 180 degrees of arc with a radius of curvature of approximately 2 to 4 cm to match the typical curvature of the aortic arch in an adult human patient and a secondary curve 2948 that is a bend of approximately 90 degrees or more where the catheter shaft 2902 will pass through the aortic wall. Additionally, the catheter shaft 2902 may be reinforced, particularly in the curved distal region 2944, for example with braided or coiled wire, to further improve the stability of the catheter 2900 in the proper position in the patient's aorta.

Illustrated in FIG. 30 is a magnified lateral cross section of the aortic catheter 2900 of FIG. 29 taken along line 30—30 in FIG. 29 illustrating the multi-lumen arrangement of the aortic catheter 2900. The catheter shaft 2902 has six lumens: a guide wire and corporeal perfusion lumen 2908, an arch perfusion lumen 2910, an arch monitoring lumen 2912, a balloon inflation lumen 2914, a cardioplegia lumen 2916 and a root pressure lumen 2918. The elongated catheter shaft 2902 has an outer diameter which is preferably from approximately 9 to 30 French (3.0–10.0 mm diameter), more preferably from approximately 12 to 18 French (4.0–6.0 mm diameter) for adult human patients. Additionally, the aortic catheter 2900 includes a distal radiopaque marker 2938 positioned near the distal end 2906 of the catheter shaft 2902, an intermediate radiopaque marker 2940 positioned near the proximal edge of the downstream anchoring member 2922, and a proximal radiopaque marker 2942 positioned near the distal edge of the upstream occlusion member 2920.

A downstream occlusion member 2922, in the form of an inflatable balloon, is mounted on the catheter shaft 2902 near the distal end 2906 of the catheter shaft 2902. When placed in the operative position, the downstream occlusion member 2922 may be partially inflated or completely inflated to a diameter sufficient to regulate blood flow in the descending aorta. For use in adult human patients, the downstream occlusion member 2922 preferably has an inflated outer diameter of approximately 0.5 cm to 4.0 cm and a length of approximately 1.0 cm to 7.5 cm. An upstream occlusion member 2920, in the form of an expandable, inflatable balloon, is mounted on the catheter shaft 2902 at a position proximal to and spaced apart from the downstream anchoring member 2922 so that it is positioned in the ascending aorta when deployed. The distance between the upstream occlusion member 2920 and the downstream occlusion member 2922 is preferably between 3 and 20 cm, more preferably between 8 and 15 cm, and is chosen so that, when the aortic catheter 2900 is deployed and the upstream occlusion member 2920 is positioned within the ascending aorta between the coronary arteries and the brachiocephalic artery, the downstream occlusion member 2922 will be positioned in the descending aorta downstream of the left subclavian artery. When inflated, the upstream occlusion member 2920 expands to a diameter sufficient to occlude blood flow in the ascending aorta. For use in adult human patients, the inflatable balloon upstream occlusion member 2920 preferably has an inflated outer diameter of approximately 1.5 cm to 4.0 cm. Preferably, the inflatable balloon upstream occlusion member 2920 has an inflated length that is not significantly longer than its inflated diameter, or, more preferably, is shorter than its inflated diameter to allow the upstream occlusion member 2920 to be easily placed within the ascending aorta between the coronary arteries and the brachiocephalic artery without any danger of inadvertently occluding either.

The arch perfusion lumen 2910 extends through the catheter shaft 2902 from the proximal end 2904 to one or more arch perfusion ports 2926 on the exterior of the catheter shaft 2902 between the upstream occlusion member 2920 and the downstream anchoring member 2922. The arch monitoring lumen 2912 extends through the catheter shaft 2902 from the proximal end to an arch monitoring port 2928 located between the upstream occlusion member 2920 and the downstream anchoring member 2922 to monitor pressure in the aortic arch. The root pressure lumen 2918 extends through the catheter shaft 2902 from the proximal end 2904 to a root pressure port 2921 located distal to the downstream anchoring member 2922 to monitor pressure in the aortic root. The common balloon inflation lumen 2914 extends through the catheter shaft 2902 from the proximal end 2904 to balloon inflation ports 2930, 2932 within the upstream occlusion member 2920 and the downstream anchoring member 2922, respectively. Alternatively, separate inflation lumens may be provided for independently inflating the upstream occlusion member 2920 and the downstream anchoring member 2922. The guide wire and corporeal perfusion lumen 2908 extends from the proximal end 2904 of the catheter shaft 2902 to one or more corporeal perfusion ports 2924 and a guide wire port 2936 at the distal end 2906, distal to the downstream anchoring member 2922. The cardioplegia lumen 2916 extends from the proximal end 2904 of the catheter shaft 2902 to a cardioplegia port 2966 proximal to the upstream occlusion member 2920. Alternatively, when a cardioplegia lumen 2926 is not included a separate cardioplegia needle or catheter may be used to infuse cardioplegia fluid into the aortic root upstream of the upstream of the occlusion member 2920.

The proximal end 2904 of the catheter shaft 2902 is connected to a manifold 2950 with fittings for each of the catheter lumens. The arch perfusion lumen 2910 is connected to a Y-fitting 2964 that has a barb connector 2956 for connection to a perfusion pump or the like and a luer connector 2958, which may be used for monitoring perfusion pressure, for withdrawing fluid samples or for injecting medications or other fluids.

The arch monitoring lumen 2912 is connected to a luer connector 2960 or other fitting suitable for connection to a pressure monitor. The balloon inflation lumen 2914 is connected to a luer connector 2966 or other fitting suitable for connection to a syringe or balloon inflation device. The guide wire and corporeal perfusion lumen 2908 is connected to a three-way Y-fitting 2970 that has a barb connector 2972 for connection to a perfusion pump, a luer connector 2974 and a guide wire port 2976 with a Touhy-Borst adapter or other hemostasis valve. The cardioplegia lumen 2916 is connected to a Y-fitting 2971 having a barb connector 2973 for connection to a cardioplegia source, and a luer connector 2977.

FIG. 31 illustrates a side view of the central superior vena cava cannula 3199 of the present invention configured for introduction into the patient's superior vena cava via an incision in the right atrium. FIG. 32 is a magnified lateral cross-section of the central superior vena cava cannula 3199 taken along line 32—32 of FIG. 31. The central superior vena cava cannula 3199 has a tubular shaft 3198 that includes a venous drainage lumen 3197 and a balloon inflation lumen 3196. The tubular shaft preferably has a length of approximately 15 cm to 90 cm and a diameter of approximately 10 to 32 French (3.3 mm to 10.7 mm diameter). Suitable materials for the elongated tubular shaft 3198 include, but are not limited to, polyvinylchloride, polyurethane, polyethylene, polypropylene, polyamides (nylons), polyesters, silicone, latex, and alloys or copolymers thereof, as well as braided, coiled or counterwound wire or filament reinforced composites. In addition, the tubular shaft 3198 may be preformed to better facilitate ease of entry into the superior vena cava from a right atrium entry site.

An occlusion balloon 3195 or other expandable occlusion member is mounted on the tubular shaft 3198 near the distal end 3179 of the cannula 3199. The occlusion balloon 3195 or other expandable occlusion member preferably has an expanded diameter of approximately 5 mm to 40 mm. The venous drainage lumen 3197 extends through the tubular shaft 3198 from a venous drainage fitting 3194 on the proximal end of the cannula 3199 to one or more venous drainage ports 3193 on the tubular shaft 3198 distal to the occlusion balloon 3195. The venous drainage lumen 3197 may also serve as a guide wire lumen having a proximal Touhy-Borst fitting 3192, or other hemostasis valve capable of creating a fluid tight seal around a guide wire and guiding catheter, to a guide wire port 3179 on the distal end 3176 of the tubular shaft 3198 distal to the occlusion balloon 3195. In addition, the proximal venous drainage fitting 3194 has a barb connector 3178 or other suitable fitting capable of being coupled to a CPB machine and a luer fitting 3175 capable of withdrawing fluid samples in the superior vena cava. The balloon inflation lumen 3196 extends through the tubular shaft 3198 from a balloon inflation fitting 3191 on the proximal end of the catheter 3199 to one or more balloon inflation ports 3190 within the occlusion balloon.

FIG. 33 illustrates a side view of the central inferior vena cava cannula 3389 of the present invention configured for introduction into the patient's inferior vena cava through the same or another incision in the right atrium. FIG. 34 is a magnified lateral cross-section of the central superior vena cava cannula 3389 taken along line 33—33 of FIG. 33. The central inferior vena cava cannula 3389 has a tubular shaft 3188 that includes a venous drainage lumen 3387 and a balloon inflation lumen 3386. The tubular shaft preferably has a length of approximately 15 cm to 90 cm and a diameter of approximately 10 to 32 French (3.3 mm to 10.7 mm diameter). Suitable materials for the elongated tubular shaft 3188 include, but are not limited to, polyvinylchloride, polyurethane, polyethylene, polypropylene, polyamides (nylons), polyesters, silicone, latex, and alloys or copolymers thereof, as well as braided, coiled or counterwound wire or filament reinforced composites. In addition, the tubular shaft 3388 may be preformed to better facilitate ease of entry into the inferior vena cava from a right atrium entry site.

An occlusion balloon 3385 or other expandable occlusion member is mounted on the tubular shaft 3388 near the distal end 3366 of the cannula 3389. The occlusion balloon 3385 or other expandable occlusion member preferably has an expanded diameter of approximately 5 mm to 40 mm. The venous drainage lumen 3387 extends through the tubular shaft 3388 from a venous drainage fitting 3384 on the proximal end of the cannula 3389 to one or more venous drainage ports 3383 on the tubular shaft 3388 distal to the occlusion balloon 3385. The venous drainage lumen 3387 may also serve as a guide wire lumen having a proximal Touhy-Borst fitting 3382, or other hemostasis valve capable of creating a fluid tight seal around a guide wire and guiding catheter, to a guide wire port 3369 on the distal end 3366 of the tubular shaft 3388 distal to the occlusion balloon 3385. In addition, the proximal venous drainage fitting 3384 has a barb connector 3365 or other suitable fitting capable of being coupled to a CPB machine and a luer fitting 3367 capable of withdrawing fluid samples in the inferior vena cava. The balloon inflation lumen 3386 extends through the tubular shaft 3388 from a balloon inflation fitting 3381 on the proximal end of the catheter 3389 to one or more balloon inflation ports 3380 within the occlusion balloon.

Figure 35:
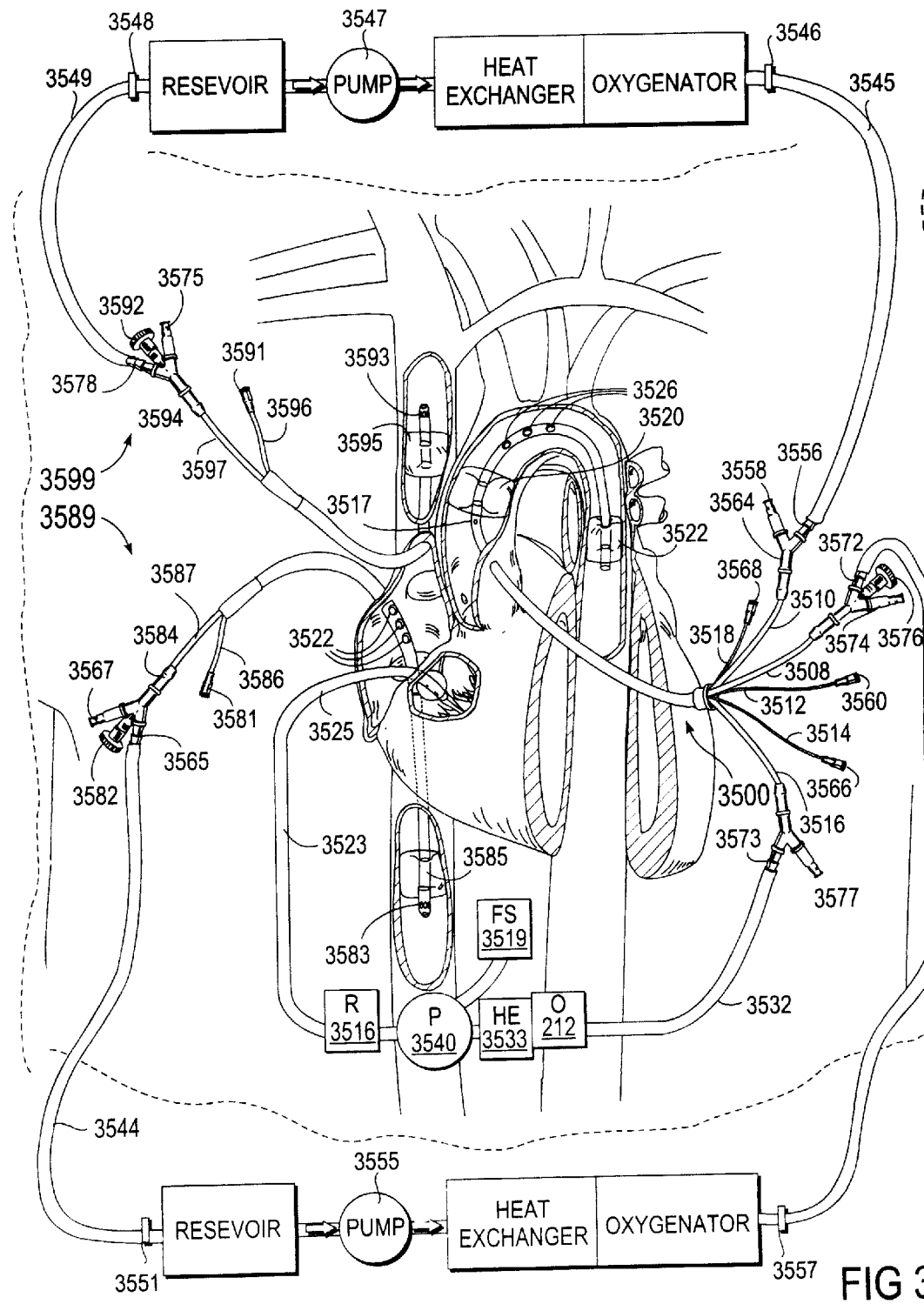
FIG. 35 is a schematic diagram of a fifth embodiment of the circulatory support system of the present invention configured for selective, isolated, dual loop perfusion of a patient's circulatory system.

FIG. 35 is a schematic diagram of a fifth embodiment of the circulatory support system of the present invention configured for selective, isolated, dual loop perfusion of a patient's circulatory system. The cerebral loop is created by connecting the venous drainage lumen 3597 of the central superior vena cava cannula 3599 to the inflow 3548 of a first blood circulation pump 3547 using suitable blood flow tubing 3549, then connecting the outflow 3546 of the first blood circulation pump 3547 to the arch perfusion lumen 3510 of the central arterial perfusion cannula 3500. The first blood circulation pump 3547 may be a peristaltic roller pump, a centrifugal blood pump or other suitable blood circulation pump. Preferably, the cerebral loop of the circulatory support system will also include a venous blood reservoir, a blood oxygenator and heat exchanger in series with the first blood circulation pump. Optionally, vacuum assist may be used to enhance venous drainage through the central superior vena cava cannula 3599. Venous blood from the head and upper extremities enters the patient's superior vena cava and is drained out through the venous drainage lumen 3597 of the central superior vena cava cannula 3599. The blood is oxygenated, cooled and recirculated by the first blood circulation pump 3547 to the head and upper extremities through the arch perfusion lumen 3510 of the central arterial perfusion cannula 3599. The corporeal circulation is prevented from mixing with the cerebral circulation on the venous side by the occlusion balloons 3595 on the superior vena cava cannula 3599 and 3585 on the inferior vena cava cannula 3589. Mixing is prevented in the arterial circulation by upstream occlusion member 3520 and downstream occlusion member 3522.

The corporeal loop of the circulatory support system is created by connecting the venous drainage lumen 3587 of the central inferior vena cava cannula 3589 to the inflow 3551 of a second blood circulation pump 3555 using suitable blood flow tubing 3544, then connecting the outflow 3557 of the second blood circulation pump 3555 to the corporeal perfusion lumen 3508 of the central arterial perfusion cannula 3500. The second blood circulation pump 3555 may be a peristaltic roller pump, a centrifugal blood pump or other suitable blood circulation pump. Preferably, the corporeal loop of the circulatory support system will also include a venous blood reservoir, a blood oxygenator and heat exchanger in series with the second blood circulation pump 3555. Optionally, vacuum assist may be used to enhance venous drainage through the central inferior vena cava cannula 540. Venous blood from the viscera and lower extremities enters the patient's inferior vena cava and is drained out through the venous drainage lumen 3587 of the central inferior vena cava cannula 3589. The blood is oxygenated, cooled and recirculated by the second blood circulation pump 3555 to the viscera and lower extremities through the corporeal perfusion lumen 3508 of the central arterial perfusion cannula 3500.

Optionally, the patient's right atrium and the coronary sinus may be drained through one or more drainage ports 3522 on the central inferior vena cava cannula 3589 or on the tubular shaft of the central superior vena cava cannula 3599 proximal to the cannula's occlusion balloon 3595. Alternatively, the patient's right atrium and the coronary sinus may be drained into a cardiotomy reservoir using a separate suction cannula. As another alternative, the coronary circulation can be isolated by inserting a coronary sinus catheter 3525 through the same or another incision in the right atrium to isolate the coronary circulation on the venous side and for antegrade or retrograde flow of blood, cardioplegia or other fluids into the patient's coronary arteries. The coronary sinus catheter 3525 will have a an occlusion balloon to seal the coronary sinus. Fluid may be perfused in the antegrade direction or fluid may be vacuumed through the coronary sinus catheter in the retrograde direction. The proximal end of the coronary sinus catheter 3525 is coupled to tubing 3523 in fluid communication with a separate pump system including a reservoir 3516 a pump 3540 a cardioplegia, or drug delivery source 3519, a heat exchanger 3533 and an oxygenator 212. The blood, cardioplegia, or drug delivery fluid is conditioned and pumped through tubing 3532 coupled to barb connector 3573 in fluid communication with cardioplegia lumen 3516 and distal fluid port 3517. The system creates a retrograde delivery subcirculation or antegrade subcirculation depending upon the rotation of the pump 3540. Alternatively a perfusion pump may be used if total isolation of the coronary circulation is not necessary which would allow mixing of fluid in the venous system.

In another aspect of the present invention, the circulatory support system can be configured for selective, closed-loop perfusion of an isolated organ system within the patient's body while the beating heart supplies the remainder of the circulatory system. In effect, this creates an isolated, dual-loop perfusion system with the patient's heart performing the function of the second blood circulation pump. A perfusion shunt device is used to allow the patient's heart to continue beating, while isolating a selected organ system within the body. Suitable perfusion shunt devices for this application are described in detail in commonly owned, copending patent application U.S. Ser. No. 09/212,5880, filed Dec. 14, 1998 by Macoviak et al., which is hereby incorporated by reference in its entirety.

Figure 36:
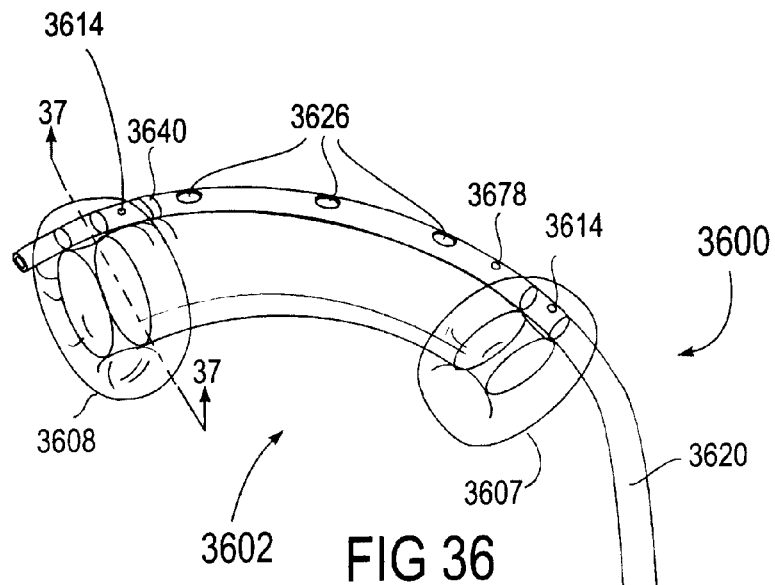
FIG. 36 is a side view of an aortic perfusion shunt apparatus configured for insertion into a patient's aorta via a peripheral artery such as the femoral artery.
Figure 37:
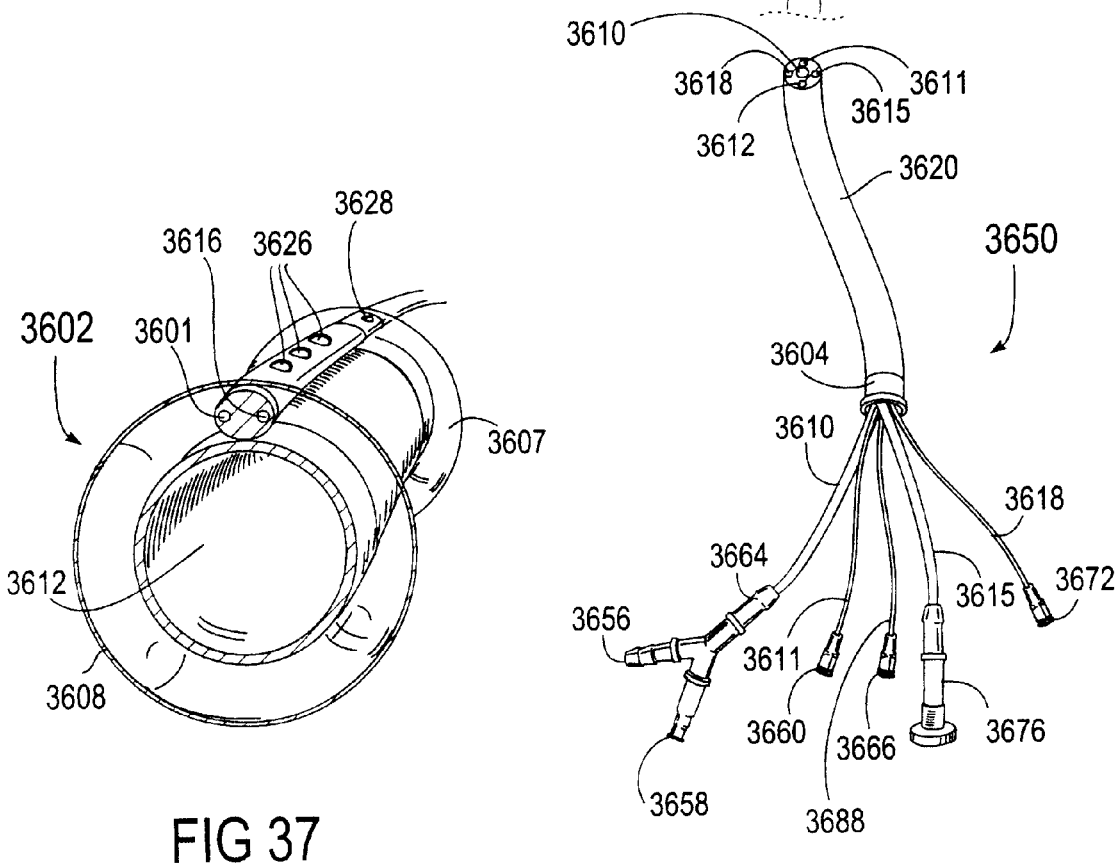
FIG. 37 is a distal end view of the expandable shunt conduit of the aortic perfusion shunt apparatus of FIG. 36 taken along line 37—37.
Figure 38:
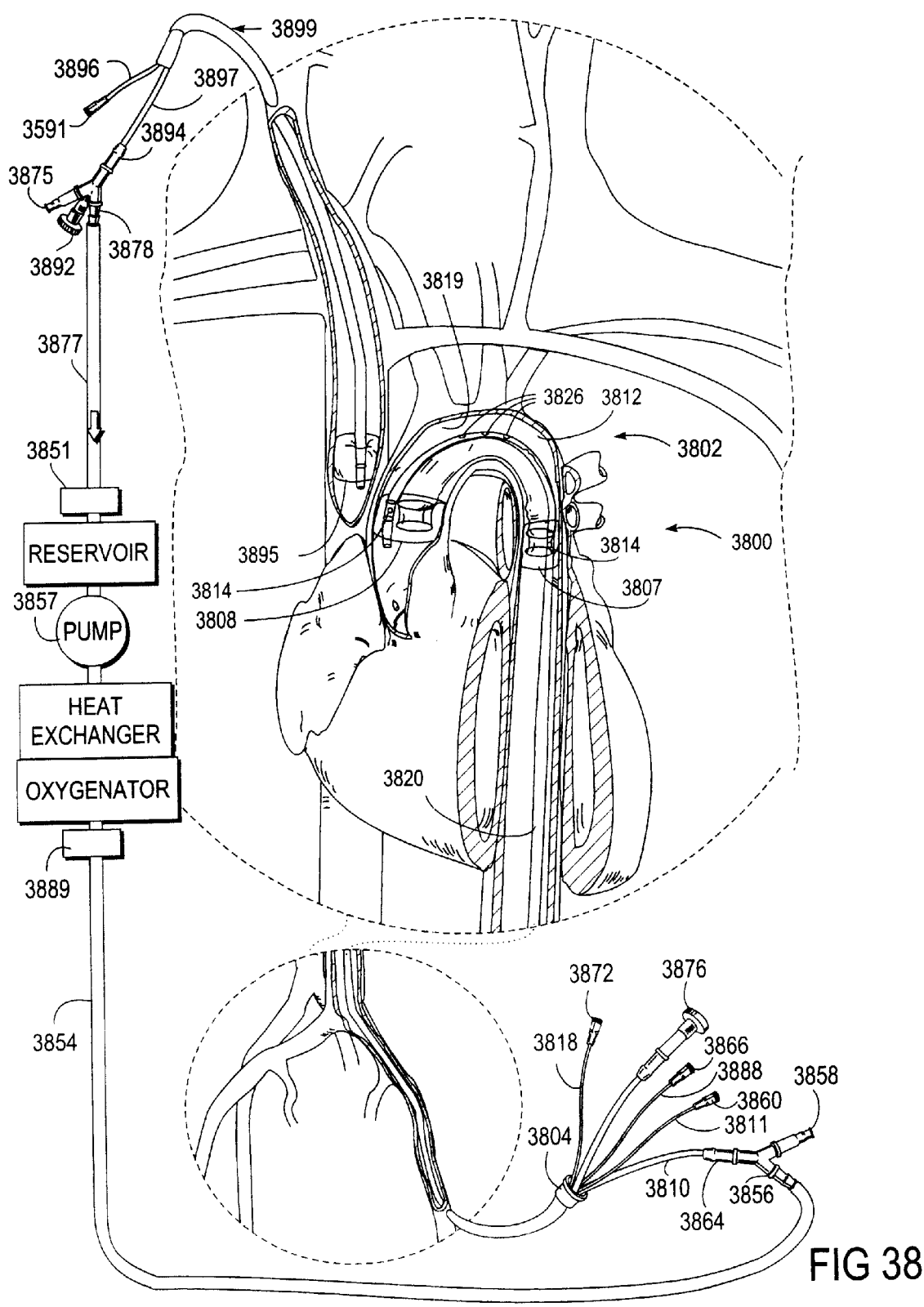
FIG. 38 shows a schematic diagram of a sixth embodiment of the circulatory support system of the present invention configured for selective, closed-loop perfusion of a patient's cerebral circulation and upper extremities, while the beating heart supplies the viscera and lower extremities with blood.

FIGS. 36 through 38 show a sixth embodiment of the circulatory support system configured for selective, closed-loop perfusion of an isolated organ system within the patient's body while the beating heart supplies the remainder of the circulatory system. FIG. 36 is a side view of the aortic perfusion shunt apparatus 3600 configured for insertion into a patient's aorta via a peripheral artery such as the femoral artery. FIG. 37 is a distal end view of the expanded shunt device 3602 illustrating a shunt conduit 3612 of the aortic perfusion shunt apparatus 3600 of FIG. 36 taken along line 37—37.

Referring now to FIG. 36, the expandable shunt device 3602 is mounted on an elongated catheter shaft 3620 for introduction into the patient's circulatory system. In this exemplary embodiment of the perfusion shunt apparatus 3600 the elongated catheter shaft 3620 is configured for retrograde deployment of the expandable shunt conduit 3602 in a patient's aortic arch via a peripheral arterial access point, such as the femoral artery. Alternatively, it may be adapted for antegrade deployment via direct aortic insertion. The elongated catheter shaft 3620 should have a length sufficient to reach from the arterial access point where it is inserted into the patient to the aortic arch. For femoral artery deployment, the elongated catheter shaft 3620 preferably has a length from approximately 60 to 120 cm, more preferably 70 to 90 cm. The elongated catheter shaft 3620 is preferably extruded of a flexible thermoplastic material or a thermoplastic elastomer. Suitable materials for the elongated catheter shaft 3620 include, but are not limited to, polyvinylchloride, polyurethane, polyethylene, polypropylene, polyamides (nylons), polyesters, and alloys or copolymers thereof, as well as braided, coiled or counterwound wire or filament reinforced composites. Optionally, the distal end of the catheter shaft 3620 may be preshaped with a curve to match the internal curvature of the patient's aortic arch.

Referring now to FIGS. 36 and 37, the elongated catheter shaft 3620 has an arch perfusion lumen 3610, a common inflation lumen 3688, an arch monitoring lumen 3611, a guide wire lumen 3615 and a root pressure lumen 3618. The arch perfusion lumen 3610 extends through the catheter shaft 3620 from the proximal end 3604 to one or more arch perfusion ports 3626 on the exterior of the catheter shaft 3620 between the upstream sealing member 3608 and the downstream sealing member 3607. The arch monitoring lumen 3611 extends through the catheter shaft 3620 from the proximal end 3604 to an arch monitoring port 3628 located between the upstream sealing mechanism 3608 and the downstream sealing mechanism 3607 to monitor pressure in the aortic arch. The root pressure lumen 3618 extends through the catheter shaft 3620 from the proximal end 3604 to a root pressure port 3601 located distal to the downstream sealing mechanism 3608 to monitor pressure in the aortic root. The common balloon inflation lumen 3688 extends through the catheter shaft 3620 from the proximal end 3604 to balloon inflation ports 3614 within the upstream sealing mechanism 3608 and the downstream sealing mechanism 3607, respectively. Alternatively, separate inflation lumens may be provided for independently inflating the upstream sealing mechanism 3608 and the downstream sealing mechanism 3607. The guide wire lumen 3615 extends from the proximal end 3604 of the catheter shaft 3620 to a guide wire port 3616 at the distal end 3606, of the catheter shaft 3620.

The proximal end 3604 of the catheter shaft 3620 is connected to a manifold 3650 with fittings for each of the catheter lumens. The arch perfusion lumen 3610 is connected to a Y-fitting 3664 that has a barb connector 3656 for connection to a perfusion pump or the like and a luer connector 3658, which may be used for monitoring perfusion pressure, for withdrawing fluid samples or for injecting medications or other fluids. The arch monitoring lumen 3611 is connected to a luer connector 3660 or other fitting suitable for connection to a pressure monitor. The balloon inflation lumen 3688 is connected to a luer connector 3666 or other fitting suitable for connection to a syringe or balloon inflation device. The guide wire lumen 3615 is connected to a guide wire port 3676 with a Touhy-Borst adapter or other hemostasis valve. The root pressure lumen 3618 is connected to a luer fitting 3672 or other suitable pressure fitting capable of being coupled to a pressure monitoring device.

Preferably, the perfusion shunt apparatus 3600 includes one or more markers, which may include radiopaque markers and/or sonoreflective markers, to enhance imaging of the perfusion shunt apparatus 3600 using fluoroscopy or ultrasound, such as transesophageal echocardiography (TEE). An upstream radiopaque and/or sonoreflective marker ring 3640 on the catheter shaft 3620 just proximal to the upstream sealing member 3608 and a second, downstream radiopaque and/or sonoreflective marker ring 3642 on the catheter shaft 2620 just distal to the downstream sealing member 3607. Alternatively or additionally, radiopaque markers and/or sonoreflective markers may be placed on the sealing members 3607, 3608 and/or the shunt conduit 3602 to show the position and/or the deployment state of the perfusion shunt apparatus 3600.

FIG. 38 shows a schematic diagram of a sixth embodiment of the circulatory support system of the present invention configured for selective, closed-loop perfusion of a patient's cerebral circulation and upper extremities, while the beating heart supplies the viscera and lower extremities with blood. In this embodiment of the circulatory support system, the aortic arch vessels are isolated using perfusion shunt apparatus 3800 and venous cannulation is provided by a superior vena cava cannula 3899 similar to the one previously described in connection with FIGS. 3 and 4, although any of the previously described venous cannula systems may be implemented.

Referring to FIG. 38, the arch perfusion shunt apparatus 3800 has an expandable shunt device 3802 mounted on an elongated catheter shaft 3820. The expandable shunt device 3802 has an expandable shunt conduit 3812 an upstream sealing member 3808 at the upstream end of the device 3802 and a downstream sealing member 3807 at the downstream end of the device 3802. The upstream and downstream sealing members 3808, 3807 may be inflatable, toroidal balloons, as illustrated, or external flow control valves may be used. A common inflation lumen 3888 or alternatively, separate inflation lumens (not shown) extend through the catheter shaft 3820 from one or more inflation fittings 3866 on the proximal end 3804 of the catheter shaft 3820 to inflation ports 3814 within the upstream occlusion member 3808 and the downstream occlusion member 3807. The expandable shunt conduit 3802 is inserted into the patient's aorta in a collapsed state and is expanded within the aortic arch when the inflated upstream sealing member 3808 is positioned between the aortic valve and the brachiocephalic artery and the inflated downstream sealing member 3807 positioned downstream of the left subclavian artery creating a fluid channel shunt conduit 3812. An arch perfusion lumen 3810, within the catheter shaft 3820, extends from a perfusion fitting 3864 at the proximal end 3804 of the catheter shaft 3820 to one or more arch perfusion ports 3826 within the annular chamber 3819 surrounding the shunt conduit 3802.

The cerebral loop of the circulatory support system is created by connecting the venous drainage lumen 3897 of the superior vena cava cannula 3899 to the inflow 3851 of a first blood circulation pump 3857 using suitable blood flow tubing 3877, then connecting the outflow 3853 of the first blood circulation pump 3857 to the arch perfusion lumen 3810 of the arch perfusion shunt apparatus 3800. The first blood circulation pump 3857 may be a peristaltic roller pump, a centrifugal blood pump or other suitable blood circulation pump. Preferably, the cerebral loop of the circulatory support system will also include a venous blood reservoir, a blood oxygenator and heat exchanger in series with the first blood circulation pump 3857. Optionally, vacuum assist may be used to enhance venous drainage through the superior vena cava cannula 3899. Venous blood from the head and upper extremities enters the patient's superior vena cava and is drained out through the venous drainage lumen 3897 of the superior vena cava cannula 3899. The blood is oxygenated, cooled and recirculated by the first blood circulation pump 3857 to the head and upper extremities through the arch perfusion lumen 3810 of the arch perfusion shunt apparatus 3800.

In this embodiment of the invention, the corporeal loop of the circulatory system is supplied by the patient's beating heart. Oxygenated blood from the heart passes through the expandable shunt conduit 3812 of the shunt device 3802, thus bypassing the aortic arch vessels. From there, the blood flows through the descending aorta to the viscera and the lower extremities in the usual manner, returning to the heart via the inferior vena cava. The corporeal circulation is prevented from mixing with the cerebral circulation on the venous side by the occlusion balloon 3895 on the superior vena cava cannula 3899.

Perfusion shunt devices can also be used to isolate other organ systems within a patient's body, such as the renal system or hepatic system. A selective, closed-loop perfusion system can be created for these organ systems by using an arterial perfusion shunt apparatus and a venous perfusion shunt apparatus connected to a blood circulation pump.

Figure 39:
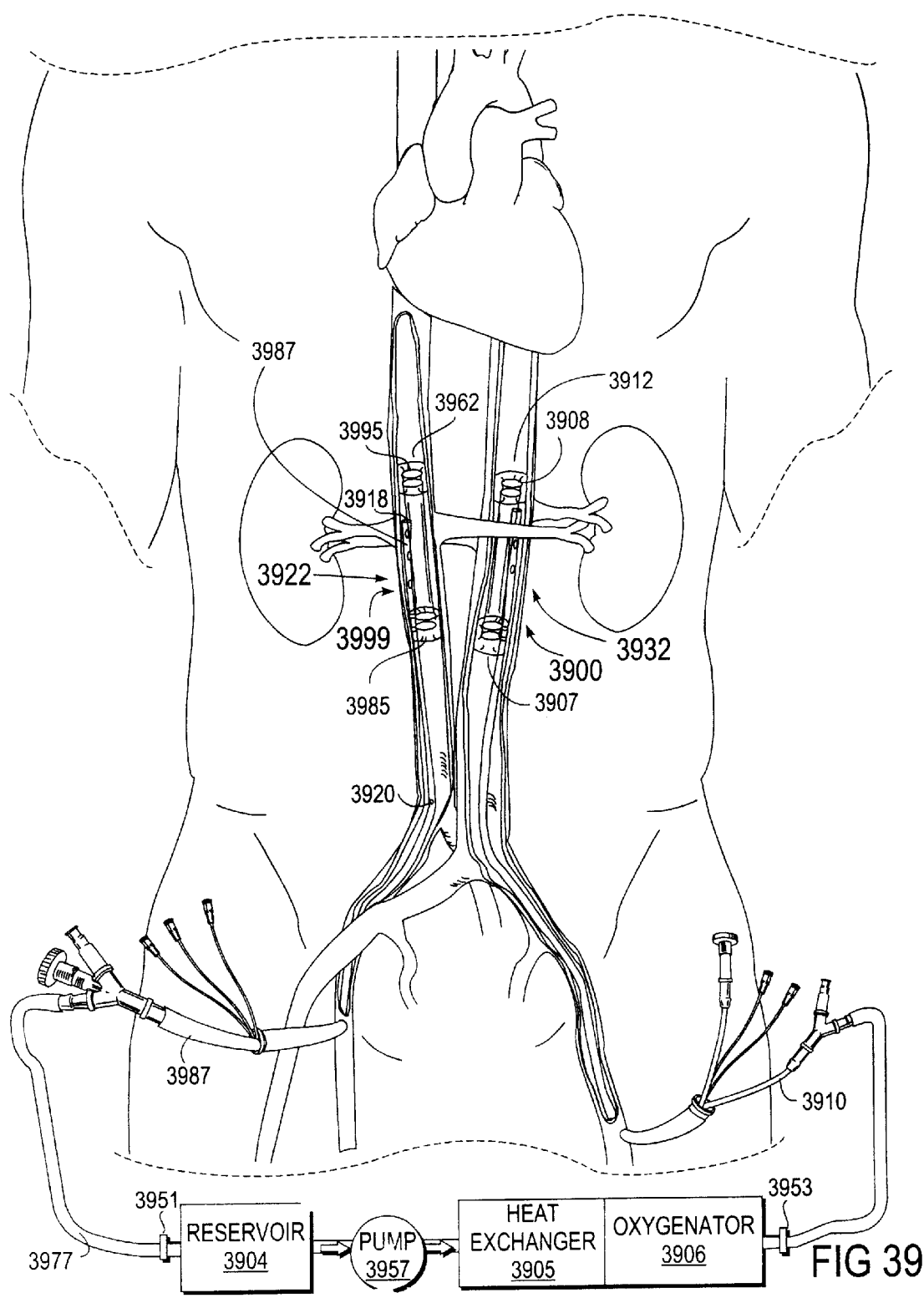
FIG. 39 shows a schematic diagram of a seventh embodiment of the circulatory support system of the present invention configured for selective, closed-loop perfusion of a patient's renal system, while the beating heart supplies the remainder of the circulatory system with blood.

FIG. 39 shows a schematic diagram of a seventh embodiment of the circulatory support system of the present invention configured for selective, closed-loop perfusion of a patient's renal system, while the beating heart supplies the remainder of the circulatory system with blood. An arterial perfusion shunt apparatus 3900 is placed in the descending aorta via the femoral artery so that the upstream sealing member 3908 and the downstream sealing member 3907 isolate the ostia of the renal arteries from the aortic lumen. A venous perfusion shunt device 3999 is placed in the inferior vena cava via the femoral vein so that the upstream sealing member 3995 and the downstream sealing member 3985 isolate the ostia of the renal veins from the lumen of the inferior vena cava.

A renal circulation loop is created within the circulatory support system by connecting the perfusion lumen 3987 of the venous perfusion shunt device 3999 to the inflow 3951 of a first blood circulation pump 3957 using suitable blood flow tubing 3977, then connecting the outflow 3953 of the first blood circulation pump 3957 to the perfusion lumen 3910 of the arterial perfusion shunt device 3900. The first blood circulation pump 3957 may be a peristaltic roller pump, a centrifugal blood pump or other suitable blood circulation pump. Preferably, the renal circulation loop of the circulatory support system will also include a venous blood reservoir 3904, a blood oxygenator 3906 and heat exchanger 3905 in series with the first blood circulation pump 3957. Optionally, vacuum assist may be used to enhance venous drainage through the venous perfusion shunt device 3999. Venous blood from the renal arteries enters the annular chamber 3918 surrounding the shunt device 3922 and is drained out through the perfusion lumen 3987 in the catheter shaft 3920. The blood is oxygenated, cooled and otherwise conditioned and recirculated by the first blood circulation pump 3957 to the renal arteries through the perfusion lumen 4010 of the arterial perfusion shunt device 3900. Alternatively, the renal circulation loop or other isolated circulatory loop may be perfused in the retrograde direction.

The remainder of the circulatory system is supplied by the patient's beating heart. Oxygenated blood from the heart flowing through the descending aorta passes through the shunt conduit 3912 of the example shunt device 3932 of the arterial perfusion shunt apparatus 3900, thus bypassing the renal arteries. From there, the blood flows through the abdominal descending aorta to the rest of the viscera and the lower extremities in the usual manner, returning to the heart via the inferior vena cava. Blood returning through the inferior vena cava passes through the lumen 3962 of the expandable shunt device 3922 of the venous prefusion shunt apparatus 3999, and bypasses the isolated renal circulation.

While the present invention has been described herein with respect to the exemplary embodiments and the best mode for practicing the invention, it will be apparent to one of ordinary skill in the art that many modification, improvements and subcombinations of the various embodiments, adaptations and variations can be made to the invention without departing from the spirit and scope thereof. In addition, it can be easily understood by one of ordinary skill in the art that any combination of the venous cannulae and arterial cannulae as well as any insertion position can be used in combination to create the desired system for a surgical intervention, the invention being defined by the claims.

What is claimed is:

1. A circulator support system comprising:
   an arterial cannulation subsystem including a first arterial perfusion lumen adapted to be inserted in a first arterial location and a second arterial perfusion lumen adapted to be inserted in a second arterial location;
   a venous cannulation subsystem including a first venous drainage lumen adapted to be inserted in a first venous location and a second venous drainage lumen adapted to be inserted in a second venous location;
   a first circulation pump connected the first arterial prefusion lumen of the arterial cannulation subsystem and the first venous drainage lumen of the venous cannulation subsystem; and
   a second circulation pump connected between the second arterial perfusion lumen of the arterial cannulation subsystem and the second venous drainage lumen of the venous cannulation subsystem.

2. The circulatory support system of claim 1, wherein:
   the arterial cannulation subsystem comprises an arterial cannula having an elongated tubular body with the first arterial perfusion lumen and the second arterial perfusion lumen extending therethrough; and
   the venous cannulation subsystem comprises a venous cannula having an elongated tubular body with the first venous drainage lumen and the second venous drainage lumen extending therethrough.

3. The circulatory support system of claim 1, wherein the arterial cannulation subsystem comprises an arterial cannula having an elongated tubular body with the first arterial perfusion lumen and the second arterial perfusion lumen extending therethrough, wherein the first arterial perfusion lumen connects to a first perfusion port and the second arterial perfusion lumen connects to a second perfusion port, and wherein the first perfusion port and the second perfusion port are spaced apart longitudinally along the elongated tubular body of the arterial cannula.

4. The circulatory support system of claim 3, wherein the arterial cannula further comprises a first arterial occlusion member mounted on an exterior of the elongated tubular body between the first perfusion port and the second perfusion port.

5. The circulatory support system of claim 4, wherein the arterial cannula further comprises a second arterial occlusion member mounted on an exterior of the elongated tubular body distal to the first perfusion port and the second perfusion port.

6. The circulatory support system of claim 1, wherein the venous cannulation subsystem comprises a venous cannula having an elongated tubular body with the first venous drainage lumen and the second venous drainage lumen extending therethrough, wherein the first venous drainage lumen connects to a first drainage port and the second venous drainage lumen connects to a second drainage port, and wherein the first drainage port and the second drainage port are spaced apart longitudinally along the elongated tubular body of the venous cannula.

7. The circulatory support system of claim 6, wherein the venous cannula further comprises a first venous occlusion member mounted on an exterior of the elongated tubular body between the first drainage port and the second drainage port.

8. The circulatory support system of claim 7, wherein the venous cannula further comprises a second venous occlusion member mounted on an exterior of the elongated tubular body distal to the first drainage port and the second drainage port.

9. The circulatory support system of claim 1, wherein the arterial cannulation subsystem comprises at least one arterial cannula having at least one occlusion balloon mounted on an exterior thereof.

10. The circulatory support system of claim 1, wherein the arterial cannulation subsystem comprises at least one arterial cannula having at,least one external catheter valve mounted on an exterior thereof.

11. The circulatory support system of claim 1, wherein the venous cannulation subsystem comprises at least one venous cannula having at least one occlusion balloon mounted on an exterior thereof.

12. The circulatory support system of claim 1, wherein the venous cannulation subsystem comprises at least one venous cannula having at least one external catheter valve mounted on an exterior thereof.

13. The circulatory support system of claim 1, further comprising a first heat exchanger connected in series with the first circulation pump.

14. The circulatory support system of claim 13, further comprising a second heat exchanger connected in series with the second circulation pump.

15. The circulatory support system of claim 1, further comprising a first blood oxygenator connected in series with the first circulation pump.

16. The circulatory support system of claim 15, further comprising a second blood oxygenator connected in series with the second circulation pump.

17. The circulatory support system of claim 1, wherein the venous cannulation subsystem further comprises a first venous sensor for sensing a condition of a first portion of a patient's blood drained by the first venous drainage lumen and a second venous sensor for sensing a condition of a second portion of the patient's blood drained by the second venous drainage lumen.

18. The circulatory support system of claim 1, wherein the arterial cannulation subsystem further comprises a first arterial sensor for sensing condition of a first portion of a patient's blood perfused through the first arterial perfusion lumen and a second arterial sensor for sensing a condition of a second portion of the patient's blood perfused through the second arterial perfusion lumen.

19. The circulatory support system of claim 1, wherein:
the arterial cannulation subsystem is configured so that, when deployed in a patient's circulatory system, the first arterial perfusion lumen communicates with the patient's aortic arch and arch vessels and the second arterial perfusion lumen communicates with the patient's descending aorta and branch vessels; and
the venous cannulation subsystem is configured so that, when deployed in the patient's circulatory system, the first venous drainage lumen communicates with the patient's superior vena cava and the second venous drainage lumen communicates with the patient's inferior vena cava.

20. The circulatory support system of claim 19, wherein:
the arterial cannulation subsystem further comprises a third arterial perfusion lumen that communicates with the patient's coronary arteries.

21. The circulatory support system of claim 19, wherein:
the venous cannulation subsystem further comprises a third venous lumen that communicates with the patient's coronary sinus.

22. A method of circulatory support of a patient comprising simultaneously:
draining a first portion of the patient's blood from a first venous location in a first segment of the patient's circulatory system;
draining a second portion of the patient's blood from a second venous location in a second segment of the patient's circulatory system;
returning the first portion of the patient's blood to a first arterial location within the first segment of the patient's circulatory system; and
returning the second portion of the patient's blood to a second arterial location within the second segment of the patient's circulatory system.

23. The method of claim 22, further comprising:
conditioning the first portion of the patient's blood before returning the first portion to the first segment of the patient's circulatory system.

24. The method of claim 23, further comprising:
conditioning the second portion of the patient's blood before returning the second portion to the second segment of the patient's circulatory system.

25. The method of claim 22, further comprising:
cooling the first portion of the patient's blood before returning the first portion to the first segment of the patient's circulatory system.

26. The method of claim 25, further comprising:
cooling the second portion of the patient's blood before returning the second portion to the second segment of the patient'is circulatory system.

27. The method of claim 22, further comprising:
oxygenating the first portion of the patient's blood before returning the first portion to the first segment of the patient's circulatory system.

28. The method of claim 27, further comprising:
oxygenating the second portion of the patient's blood before returning the second portion to the second segment of the patient's circulatory system.

29. The method of claim 22, further comprising:
adding protective or therapeutic agents to the first portion of the patient's blood before returning the first portion to the first segment of the patient's circulatory system.

30. The method of claim 29, further comprising:
adding protective or therapeutic agents to the second portion of the patient's blood before returning the second portion to the second segment of the patient's circulatory system.

31. The method of claim 22, further comprising:
isolating the first segment of the patient's circulatory system from the second segment of the patient's circulatory system on the arterial side of the patient's circulatory system.

32. The method of claim 31, further comprising:
isolating the first segment of the patient's circulatory system from the second segment of the patient's circulatory system on the venous side of the patient's circulatory system.

33. The method of claim 22, further comprising inflating an occlusion balloon on the arterial side of the patient's circulatory system to isolate the first segment of the patient's circulatory system from the second segment of the patient's circulatory system.

34. The method of claim 22, further comprising expanding an external catheter valve on the arterial side of the patient's circulatory system to isolate the first segment of the patient's circulatory system from the second segment of the patient's circulatory system.

35. The method of claim 22, further comprising:
isolating the first segment of the patient's circulatory system from the second segment of the patient's circulatory system on the venous side of the patient's circulatory system.

36. The method of claim 22, further comprising inflating an occlusion balloon on the venous side of the patient's circulatory system to isolate the first segment of the patient's circulatory system from the second segment of the patient's circulatory system.

37. The method of claim 22, further comprising expanding an external catheter valve on the venous side of the patient's circulatory system to isolate the first segment of the patient's circulatory system from the second segment of the patient's circulatory system.

38. The method of claim 22, wherein:

the first venous location comprises the patient's superior vena cava;

the second venous location comprises the patient's inferior vena cava;

the first arterial location comprises the patient's aortic arch and arch vessels; and the second arterial location comprises the patient's descending aorta and branch vessels.

39. The method of claim 38, further comprising draining a third portion of the patient's blood and returning the third portion of the patient's blood to the patient's coronary arteries.

40. The method of claim 39, further comprising draining the third portion of the patient's blood from the patient's coronary sinus.

41. The method of claim 38, further comprising:

conditioning the first portion of the patient's blood to a temperature of approximately 32° C. or lower; and conditioning the second portion of the patient's blood to a temperature of approximately 32 to 37° C.

42. The method of claim 38, further comprising:

adding neuroprotective agents to the first portion of the patient's blood.

43. The method of claim 38, further comprising:

infusing a cardioplegic/agent into the patient's coronary arteries.

44. The method of claim 38, further comprising:

infusing a cardioplegic agent into the patient's coronary sinus.

45. The method of claim 22, further comprising:

sensing a condition of the first portion of the patient's blood from the first venous location in the first segment of the patient's circulatory system; and sensing a condition of the second portion of the patient's blood from the second venous location in the second segment of the patient's circulatory system.

46. The method of claim 45, further comprising:

sensing a condition of the first portion of the patient's blood returned to the first arterial location in the first segment of the patient's circulatory system; and sensing a condition of the second portion of the patient's blood returned to the second arterial location in the second segment of the patient's circulatory system.

* * * * *